United States Patent
Hu et al.

(10) Patent No.: US 9,738,652 B2
(45) Date of Patent: Aug. 22, 2017

(54) SPIRO UREA COMPOUNDS AS RSV ANTIVIRAL COMPOUNDS

(71) Applicant: Janssen Sciences Ireland UC, Little Island, Co Cork (IE)

(72) Inventors: Lili Hu, Mechelen (BE); Samuël Dominique Demin, Antwerp (BE); Sandrine Marie Helene Vendeville, Woluwe-Saint-Pierre (BE); Abdellah Tahri, Anderlecht (BE); Pierre Jean-Marie Bernard Raboisson, Rosieres (BE)

(73) Assignee: JANSSEN SCIENCES IRELAND UC, Little Island, County Cork (IE)

( * ) Notice: Subject to any disclaimer, the term of this patent is extended or adjusted under 35 U.S.C. 154(b) by 0 days.

(21) Appl. No.: 15/303,989

(22) PCT Filed: Apr. 13, 2015

(86) PCT No.: PCT/EP2015/057949
§ 371 (c)(1),
(2) Date: Oct. 13, 2016

(87) PCT Pub. No.: WO2015/158653
PCT Pub. Date: Oct. 22, 2015

(65) Prior Publication Data
US 2017/0044172 A1    Feb. 16, 2017

(30) Foreign Application Priority Data

Apr. 14, 2014 (EP) .................... 14164596

(51) Int. Cl.
*C07D 487/10* (2006.01)
*C07D 471/20* (2006.01)
*C07D 519/00* (2006.01)

(52) U.S. Cl.
CPC ......... *C07D 487/10* (2013.01); *C07D 471/20* (2013.01); *C07D 519/00* (2013.01)

(58) Field of Classification Search
None
See application file for complete search history.

(56) References Cited

U.S. PATENT DOCUMENTS

2014/0308282 A1   10/2014   Cockerill et al.
2015/0259367 A1    9/2015   Tahri et al.

FOREIGN PATENT DOCUMENTS

| CN | 102516263 | * | 6/2012 |
|----|-----------|---|--------|
| WO | 2004069256 A1 | | 8/2004 |
| WO | 2004076455 A1 | | 9/2004 |
| WO | 2005058870 A1 | | 6/2005 |
| WO | 2012080446 A1 | | 6/2012 |
| WO | 2012080447 A1 | | 6/2012 |
| WO | 2012080449 A1 | | 6/2012 |
| WO | 2012080450 A1 | | 6/2012 |
| WO | 2012080451 A1 | | 6/2012 |
| WO | 2013068769 A1 | | 5/2013 |
| WO | 2014060411 A1 | | 4/2014 |

OTHER PUBLICATIONS

Cockerill, et al., "Preparation of substituted benzimidazoles as RSV inhibitors", CAPLUS Accession 2013:763544, (2013).
Combrink et al., "Respiratory syncytial virus fusion inhibitors. Part 6: An examination of the effect of structural variation of the benzimidazol-2-one heterocycle moiety", Bioorganic & Medicinal Chemistry Letters, vol. 17, pp. 4784-4790 (2007).
Hallak et al., "Glycosaminoglycan sulfation requirements for respiratory syncytial virus infection", Journal of Virology vol. 74(22), pp. 10508-10513 (Nov. 2000).
Iqbal, et al., "Synthesis and Am

(56) References Cited

OTHER PUBLICATIONS

Wang et al., "Respiratory syncytial virus fusion inhibitors. Part 5 : Optimization of benzimidazole substitution patterns towards derivatives with improved activity", Bioorganic & Medicinal Chemistry Letters, vol. 17, pp. 4592-4598 (2007).
Extended European search report dated Jan. 18, 2013, for corresponding European application 12188694.9.
Extended European search report dated Jan. 17, 2013, for corresponding European application 13159431.9.
International search report dated Dec. 13, 2013, for corresponding international application PCT/EP2013/071525.
Wide et al. "CL387626 exhibit marked and unusual antiviral activity against respiratory syncytial virus in tissue culture and cotton rats", Antiviral Research, vol. 38; pp. 31-42 (1998).

* cited by examiner

SPIRO UREA COMPOUNDS AS RSV ANTIVIRAL COMPOUNDS

CROSS-REFERENCE TO RELATED APPLICATIONS

This application is a national phase entry of International Application No. PCT/EP2015/057949, filed on Apr. 13, 2015, which claims priority to EP Patent Application No. 14164596.0, filed on Apr. 14, 2014, each of which is incorporated herein in its entirety.

FIELD OF THE INVENTION

The invention concerns novel substituted Spiro urea azetidinyl or piperidinyl compounds having antiviral activity, in particular, having an inhibitory activity on the replication of the respiratory syncytial virus (RSV). The invention further concerns the preparation of such novel compounds, compositions comprising these compounds, and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue that provides an aerosol treatment for serious RSV infection in hospitalized children. The aerosol route of administration, the toxicity (risk of teratogenicity), the cost and the highly variable efficacy limit its use. The other two drugs, RespiGam® (RSV-IG) and Synagis® (palivizumab), polyclonal and monoclonal antibody immunostimulants, are intended to be used in a preventive way. Both are very expensive, and require parenteral administration.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication. It would be particularly preferred to provide drugs against RSV replication that could be administered perorally.

Compounds that exhibit RSV inhibitory activity are disclosed in WO-2012/080446, WO-2012/080447, WO-2012/080449, WO-2012/080450, WO-2012/080451, WO-2013/068769, and WO-2014/060411.

WO-2004/069256 discloses 2-cyanopyrrolopyrimidines and WO-2004/076455 discloses spiro-substituted 2-cyano-pyrrolopyrimidines as capthepsin K or S inhibitors useful in the treatment of various pain disorders. Teno N. et al. in Bioorganic & Medicinal Chemistry Letters, vol. 17, 6096-6100 (2007) and Teno N. et al. in J. Med. Chem., vol. 51, 5459-5462 (2008) disclose 2-cyanopyrrolopyrimidines as cathepsin K inhibitors.

SUMMARY OF THE INVENTION

The present invention relates to a compound of formula (I),

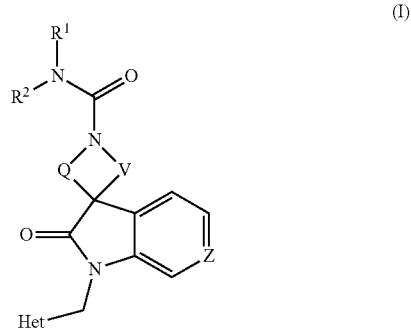

including any stereochemically isomeric form thereof, wherein

Het is a heterocyclic moiety of either of the following formula (a), (b) or (c):

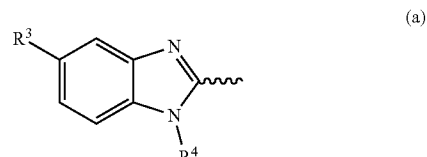

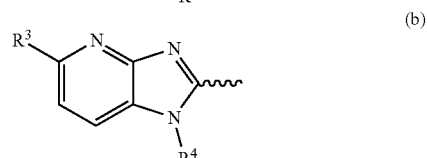

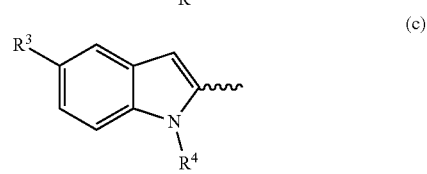

Q is $CH_2$ or $CH_2CH_2$;
V is $CH_2$ or $CH_2CH_2$;
Z is CH or N;
$R^1$ is $C_{1-6}$alkyl; $C_{3-6}$cycloalkyl; $C_{3-6}$cycloalkyl substituted with hydroxy; $Het^1$; or $C_{1-6}$alkyl substituted with one substituent selected from halo, hydroxy, polyhalo$C_{1-4}$alkyl, $NR^5R^6$, $Het^2$, $C_{3-6}$cycloalkyl, or $C_{3-6}$cycloalkyl substituted with hydroxy;
  wherein $R^5$ is hydrogen or $C_{1-4}$alkyl; and $R^6$ is hydrogen or $C_{1-4}$alkyl;

$R^2$ is hydrogen or $C_{1-6}$alkyl;
$R^3$ is halo;
$R^4$ is —$(CH_2)_m$—$R^7$;
m is an integer from 2 to 4;
$R^7$ is halogen, CN, $CF_3$, or $SO_2CH_3$; and
$Het^1$ is azetidinyl, pyrrolidinyl, piperidinyl, or tetrahydropyranyl; wherein $Het^1$ is optionally substituted with $C_{1-4}$alkyl, polyhalo$C_{1-4}$alkyl or $C_{1-4}$alkyloxycarbonyl;
$Het^2$ is azetidinyl, pyrrolidinyl, piperidinyl, piperazinyl, morpholinyl or tetrahydropyranyl; wherein $Het^2$ is optionally substituted with $C_{1-4}$alkyl or polyhalo$C_{1-4}$alkyl;
or a pharmaceutically acceptable acid addition salt thereof.

As used in the foregoing definitions:
halo is generic to fluoro, chloro, bromo and iodo;
$C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like;
$C_{1-6}$alkyl is meant to include $C_{1-4}$alkyl and the higher homologues thereof having 5 or 6 carbon atoms, such as, for example, 2-methylbutyl, pentyl, hexyl and the like;
$C_{3-6}$cycloalkyl is generic to cyclopropyl, cyclobutyl, cyclopentyl, and cyclohexyl;
polyhalo$C_{1-4}$alkyl is defined as polyhalosubstituted $C_{1-4}$alkyl, in particular $C_{1-4}$alkyl (as hereinabove defined) substituted with 2 to 6 halogen atoms such as difluoromethyl, trifluoromethyl, trifluoroethyl, and the like.

The term "compounds of the invention" as used herein, is meant to include the compounds of formula (I), and the pharmaceutically acceptable salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the terms "compound of formula (I)" and "intermediates of synthesis of formula (I)" are meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light. When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Some of the compounds according to formula (I) may also exist in their tautomeric form. Such forms in so far as they may exist, although not explicitly indicated in the above formula (I) are intended to be included within the scope of the present invention.

It follows that a single compound may exist in both stereoisomeric and tautomeric form.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

Interesting compounds of formula (I) are those compounds of formula (I) wherein one or more of the following restrictions apply:
a) Het is of formula (a); or
b) Het is of formula (b); or
c) Het is of formula (c); or
d) Q is $CH_2$ and V is $CH_2$; or
e) Q is $CH_2CH_2$ and V is $CH_2CH_2$; or
f) $R^3$ is chloro; or
g) $R^4$ is —$(CH_2)$—$R^7$ wherein m is 3 and $R^7$ is $SO_2CH_3$; or
h) $R^4$ is —$(CH_2)$—$R^7$ wherein m is 3 and $R^7$ is CN; or
i) $R^4$ is —$(CH_2)$—$R^7$ wherein m is 3 and $R^7$ is $CF_3$; or
j) $R^4$ is —$(CH_2)$—$R^7$ wherein m is 4 and $R^7$ is halo; or
k) $R^1$ is $C_{1-6}$alkyl and $R^2$ is hydrogen; or
l) $R^1$ is $Het^1$ and $R^2$ is hydrogen; or m) $R^1$ is $C_{3-6}$cycloalkyl substituted with hydroxy and $R^2$ is hydrogen.

In a first embodiment the present invention concerns compounds of formula (I)

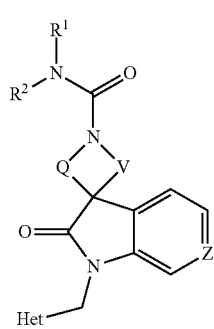

(I)

including any stereochemically isomeric form thereof, wherein

Het is a heterocyclic moiety of either of the following formula (a), (b) or (c):

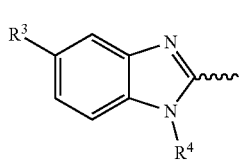

(a)

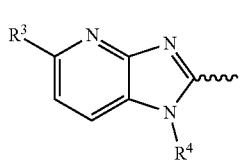

(b)

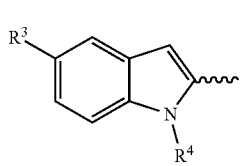

(c)

Q is $CH_2$ or $CH_2CH_2$;
V is $CH_2$ or $CH_2CH_2$;
Z is CH or N;
$R^1$ is $C_{1-6}$alkyl; $C_{3-6}$cycloalkyl substituted with hydroxy; $Het^1$; or $C_{1-6}$alkyl substituted with one substituent selected from hydroxy, polyhalo$C_{1-4}$alkyl, $NR^5R^6$, or $Het^2$;
wherein $R^5$ is $C_{1-4}$alkyl, and $R^6$ is $C_{1-4}$alkyl;
$R^2$ is hydrogen or $C_{1-4}$alkyl;
$R^3$ is chloro;
$R^4$ is —$(CH_2)_m$—$R^7$;
m is an integer from 2 to 4;
$R^7$ is halogen, CN, $CF_3$, or $SO_2CH_3$; and
$Het^1$ is piperidinyl or tetrahydropyranyl; wherein $Het^1$ is optionally substituted with $C_{1-4}$alkyl, $CF_3$ or $C_{1-4}$alkyloxycarbonyl;
$Het^2$ is morpholinyl;

or a pharmaceutically acceptable acid addition salt thereof.

A second embodiment of the present invention concerns compounds of formula (I)

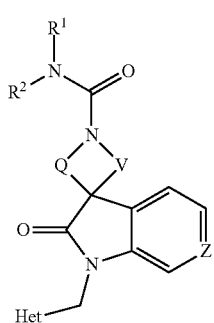

(I)

including any stereochemically isomeric form thereof, wherein

Het is a heterocyclic moiety of either of the following formula (a), (b) or (c):

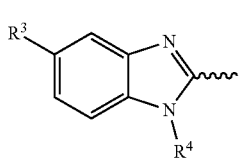

(a)

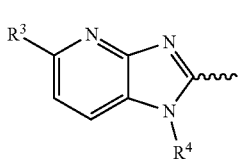

(b)

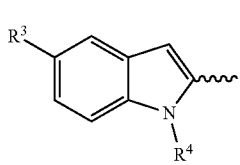

(c)

Q is $CH_2$ or $CH_2CH_2$;
V is $CH_2$ or $CH_2CH_2$;
Z is CH or N;
$R^1$ is $C_{1-6}$alkyl; $C_{3-6}$cycloalkyl substituted with hydroxy; $Het^1$; or $C_{1-6}$alkyl substituted with one substituent selected from hydroxy, polyhalo$C_{1-4}$alkyl, $NR^5R^6$, or $Het^2$;
wherein $R^5$ is $C_{1-4}$alkyl, and $R^6$ is $C_{1-4}$alkyl;
$R^2$ is hydrogen or $C_{1-4}$alkyl;
$R^3$ is chloro;
$R^4$ is —$(CH_2)_m$—$R^7$;
m is an integer from 2 to 4;
$R^7$ is halogen, CN, $CF_3$, or $SO_2CH_3$; and
$Het^1$ is piperidinyl or tetrahydropyranyl; wherein $Het^1$ is optionally substituted with $C_{1-4}$alkyl, $CF_3CH_2$ or $C_{1-4}$alkyloxycarbonyl;
$Het^2$ is morpholinyl;

or a pharmaceutically acceptable acid addition salt thereof.

A first group of compounds of formula (I) are those compounds of formula (I) wherein Q is $CH_2$, V is $CH_2$, and Z is CH.

A second group of compounds of formula (I) are those compounds of formula (I) wherein Q is $CH_2CH_2$, V is $CH_2CH_2$, and Z is CH.

A third group of compounds of formula (I) are those compounds of formula (I) wherein Q is $CH_2$, V is $CH_2$, and Z is N.

A fourth group of compounds of formula (I) are those compounds of formula (I) wherein Q is $CH_2CH_2$, V is $CH_2CH_2$, and Z is N.

A $5^{th}$ group of compounds of formula (I) are those compounds of formula (I) wherein Q is $CH_2$, V is $CH_2$, Z is CH, and Het is (a).

A $6^{th}$ group of compounds of formula (I) are those compounds of formula (I) wherein Q is $CH_2CH_2$, V is $CH_2CH_2$, Z is CH, and Het is (a).

A $7^{th}$ group of compounds of formula (I) are those compounds of formula (I) wherein Q is $CH_2$, V is $CH_2$, Z is N, and Het is (a).

An $8^{th}$ group of compounds of formula (I) are those compounds of formula (I) wherein Q is $CH_2CH_2$, V is $CH_2CH_2$, Z is N, and Het is (a).

A $9^{th}$ group of compounds of formula (I) are those compounds of formula (I) wherein Q is $CH_2$, V is $CH_2$, Z is CH, and Het is (b).

A $10^{th}$ group of compounds of formula (I) are those compounds of formula (I) wherein Q is $CH_2CH_2$, V is $CH_2CH_2$, Z is CH, and Het is (b).

A $11^{th}$ group of compounds of formula (I) are those compounds of formula (I) wherein Q is $CH_2$, V is $CH_2$, Z is N, and Het is (b).

A $12^{th}$ group of compounds of formula (I) are those compounds of formula (I) wherein Q is $CH_2CH_2$, V is $CH_2CH_2$, Z is N, and Het is (b).

A $13^{th}$ group of compounds of formula (I) are those compounds of formula (I) wherein Q is $CH_2$, V is $CH_2$, Z is CH, and Het is (c).

A $14^{th}$ group of compounds of formula (I) are those compounds of formula (I) wherein Q is $CH_2CH_2$, V is $CH_2CH_2$, Z is CH, and Het is (c).

A $15^{th}$ group of compounds of formula (I) are those compounds of formula (I) wherein Q is $CH_2$, V is $CH_2$, Z is N, and Het is (c).

A $16^{th}$ group of compounds of formula (I) are those compounds of formula (I) wherein Q is $CH_2CH_2$, V is $CH_2CH_2$, Z is N, and Het is (c).

Compounds of formula (I), or their pharmaceutically acceptable salts, can be prepared according to the reaction schemes discussed herein below using synthetic methods known in the art of organic chemistry, or modifications and derivatisations that are familiar to those skilled in the art. The starting materials used herein are commercially available or may be prepared by routine methods known in the art such as those methods disclosed in standard reference books. Preferred methods include, but are not limited to, those described below.

During any of the following synthetic sequences it may be necessary and/or desirable to protect sensitive or reactive groups on any of the molecules concerned. This can be achieved by means of conventional protecting groups well known the skilled person.

Unless otherwise indicated, the substituents in the schemes are defined as above. Isolation and purification of the products is accomplished by standard procedures, which are known to a chemist of ordinary skill.

The following schemes are exemplary of the processes for making compounds of formula (I). In the schemes below, the numerals used, including numerals from I to XXXV, are used for convenience to designate the formulae in the schemes.

The compounds of formula (I) can be synthesized for instance from intermediate (II), using a known method of urea formation. This includes, but is not limited to, the reaction of intermediate (II) with an isocyanate, or using a carbonylation agent such as triphosgene, phosgene, CDI, S,S-dimethyldithiocarbonate, followed by the addition of an amine $NHR^1R^2$, in the presence of a base if appropriate. In scheme 1, an intermediate (II) is reacted with triphosgene in the presence of a base, for example pyridine, in an organic solvent such as dichloromethane, to give the chloroimidate intermediate. Reaction of this intermediate with a mono or di-substituted amine, in the presence of a base, such as triethylamine, or Hunig's base, gives the compound (I).

Scheme 1: general synthesis of compounds of formula (I)

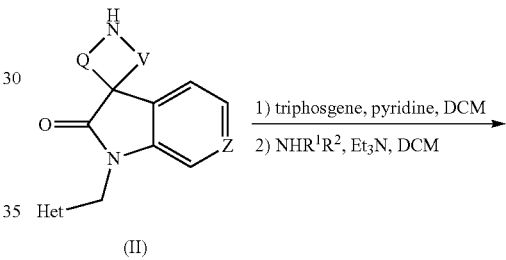

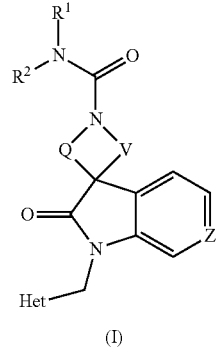

The compounds of formula (IIa) can be synthesized for instance using one of the methods shown in Scheme 2. In general, an alcohol (IIIa) or derivative (Va) is coupled with an oxindole derivative (IV) resulting in derivatives of formula (VIa), wherein the protecting group PG can be removed using art known procedures, to give compound (IIa). For instance, when PG is a tert-butyloxygroup (Boc group), it can be removed in acidic conditions, using trifluoroacetic acid in dichloromethane, or HCl in a suitable organic solvent. When PG is benzyl, it can be removed by catalytic hydrogenation for example.

Scheme 2: general synthesis of compounds of formula (IIa)

Method 1

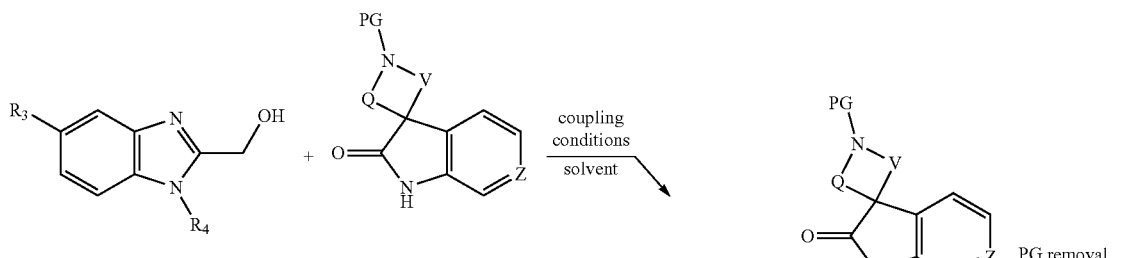

Method 2

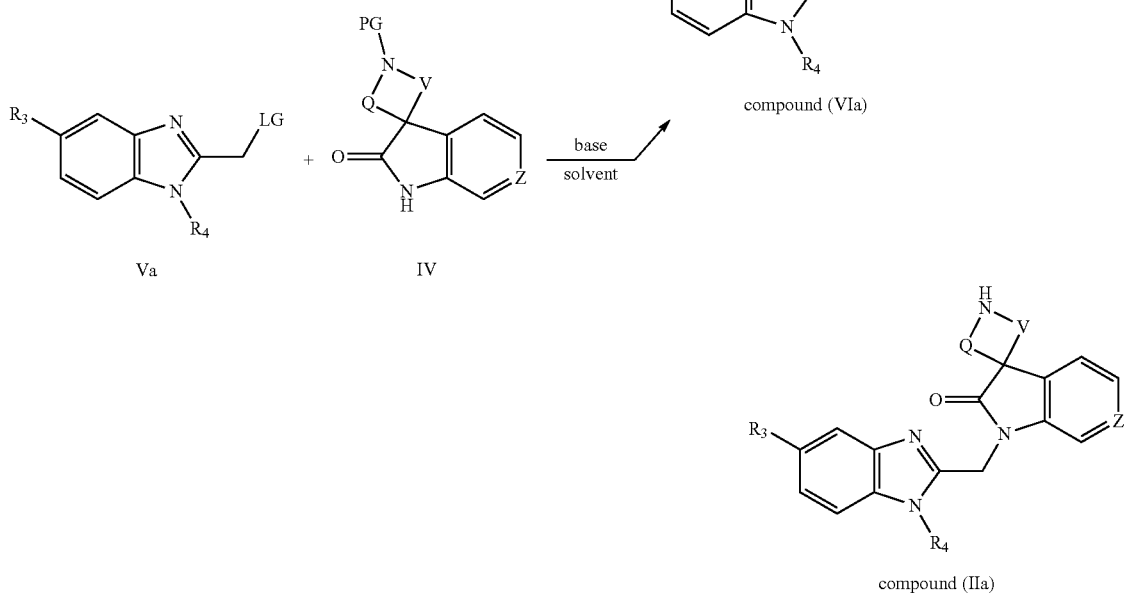

LG = Cl, Br, OTos, OMs
PG = Boc, benzyl

For method 1, an example of suitable "coupling conditions" to react (IIIa) with (IV) to form compounds of formula (VIa) is a Mitsunobu reaction, wherein PG is a suitable protecting group, such as, but not limited to e.g. Boc or benzyl. A suitable solvent for this type of reaction is THF (tetrahydrofuran).

Alternatively, a compound (Va) wherein the LG is a leaving group, such as halide, preferably chlorine, or sulfonate, can be reacted with (IV) through a base mediated coupling reaction (method 2). Possible bases to effect this reaction are $K_2CO_3$, $Cs_2CO_3$, triethylamine, sodium hydride. A suitable solvent for this type of base mediated coupling is DMF (dimethylformamide) or THF (tetrahydrofuran).

Compounds of formula (IIIa) can be generally prepared as depicted in scheme 3.

Scheme 3: general synthesis of compounds (IIIa)

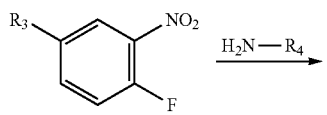

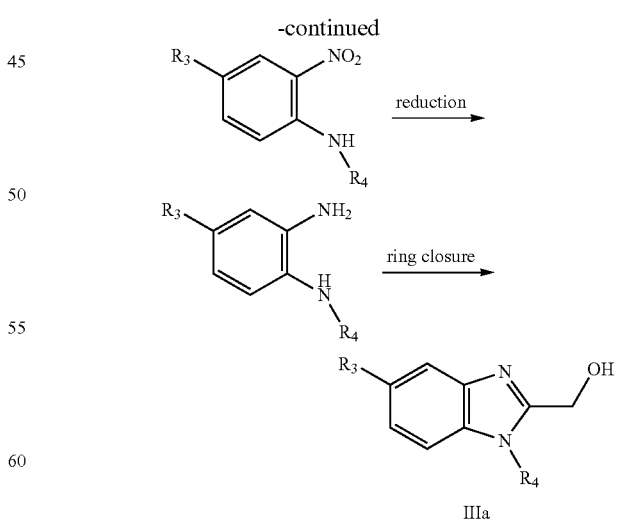

In general, compounds of formula (Va) can be prepared from compounds of formula (IIIa) using reagents like $SOCl_2$, $PBr_3$, p-TsCl, or MsCl.

Scheme 4: general synthesis of compounds (Va)

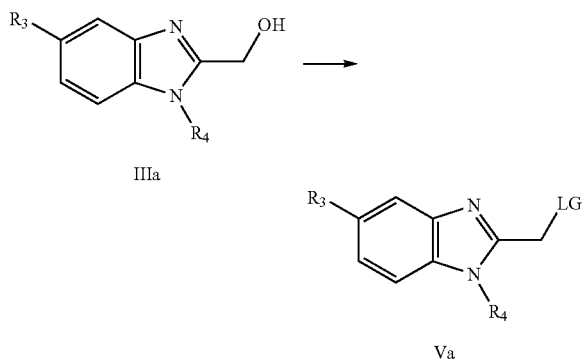

Compounds of formula (IV) can be prepared as depicted in Scheme 5.

Scheme 5: general synthesis of compounds (IV)

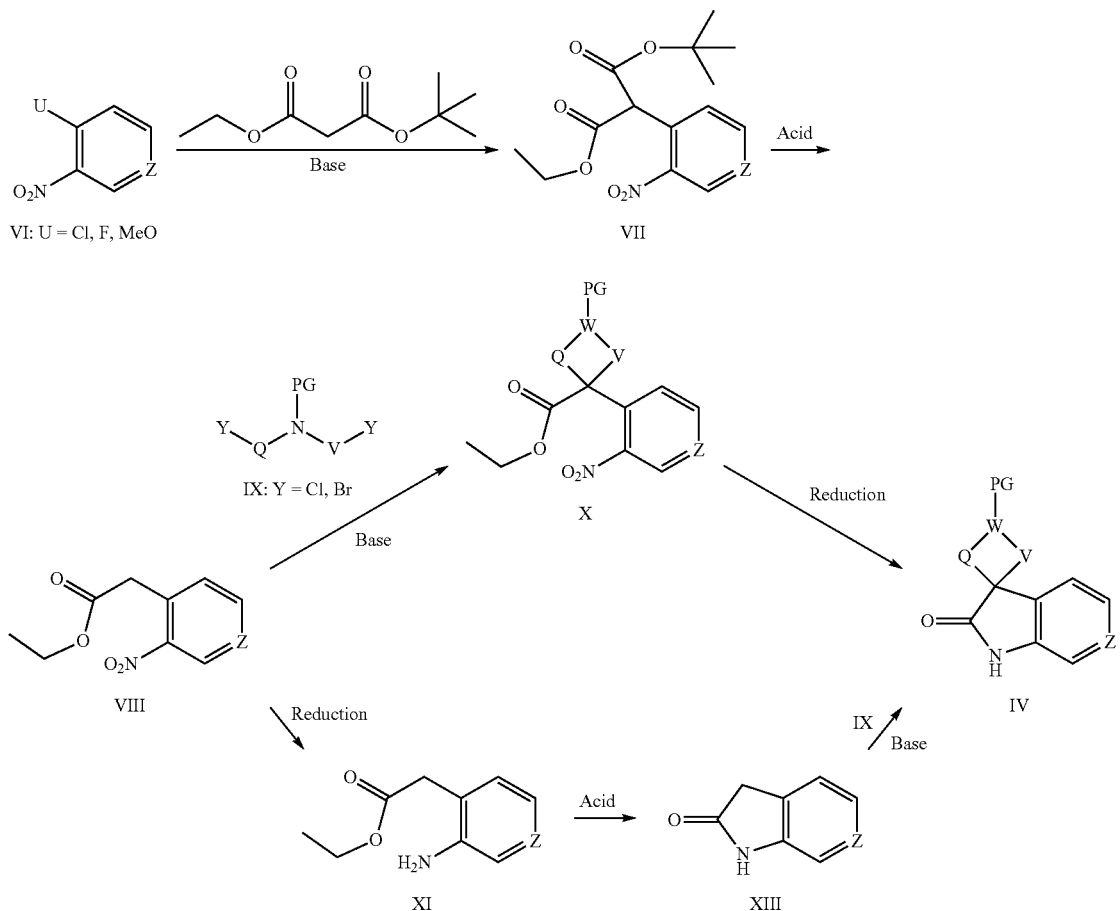

gives an compound of formula (VII). The treatment of compound (VII) with an acid such as trifluoroacetic acid or dry hydrochloric acid gives compound (VIII). The latter can be transformed to compound (X) by a condensation with a bis halo compound (IX) preferably bromo in the presence of a suitable base such as potassium carbonate, sodium carbonate, sodium hydride and the like in a suitable solvent such as DMF, THF or a like. Reduction of the nitro group of the compound (X) when it's done in a stoichiometric way using iron in the presence of ammonium chloride or tin chloride in the presence of concentrated hydrochloric acid gives directly compound (IV).

Alternatively, the compound of formula (VIII) can be reduced first in a catalytic way using hydrogen in the presence of a catalyst such as palladium or platinum, in a suitable solvent such as methanol, to give compound (XI). The latter can be transformed to compound (XII) in acidic conditions using hydrochloric acid or a like in a suitable solvents such as alcohols for example isopropanol. The The synthesis of spiro-2-oxo-indole derivatives and spiro-2-oxo-azaindole derivatives is shown in scheme 5. Displacement of (U), which is a halide, preferably fluorine, or an alkyloxy group, preferably methoxy, of the nitro pyridine or of nitro aryl of formula (VI) with tert-butyl ethyl malonate, in a suitable solvent such as THF or DMF, in the presence of a base such as sodium hydride or potassium carbonate, condensation of compound (XII) with a bis halo compound (IX), preferably chloro or bromo, is performed in the presence of a suitable inorganic base such as potassium carbonate, sodium carbonate, sodium hydride or a like in a suitable solvent such as DMF, THF or a like or using an organic base such as sodium hexamethyldisilazide (NaHMDS) or alkyl lithium bases e.g. nBuLi in a suitable solvents such THF or ether to give compound (IV).

Scheme 6: general synthesis of compounds (IV)

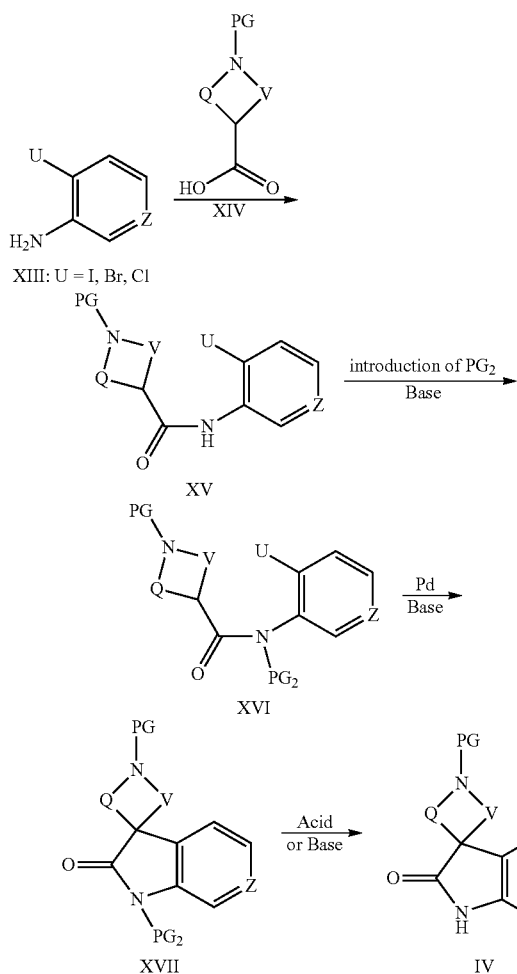

Scheme 7 illustrates a method for the preparation of compounds of formula (IIb), where $R^3$, $R^4$, Q, V, Z and PG are defined as above.

Referring to scheme 7, a compound of formula (VIb) can be synthesized by coupling 2-hydroxymethylene imidazopyridines (IIIb) with spiro oxo-indole or spiro oxo-azaindole (IV) in a known in the art method such as a Mitsunobu reaction which uses for example azadiisopropyldicarboxylate and triphenyl phosphine in a suitable solvent such as DMF or THF. Alternatively, compound of formula (VIb) may be prepared by displacement of (LG) on compound (Vb), where LG is a leaving group, which is a halide, preferably chlorine, or a sulfonate such as mesylate in the presence of a base such as sodium hydride, potassium carbonate or cesium carbonate in a suitable solvent such as DMF or THF. The removal of protecting group in compound (VIb), can be performed using art known procedures yielding compound (IIb).

Scheme 7: preparation of compound (IIb).

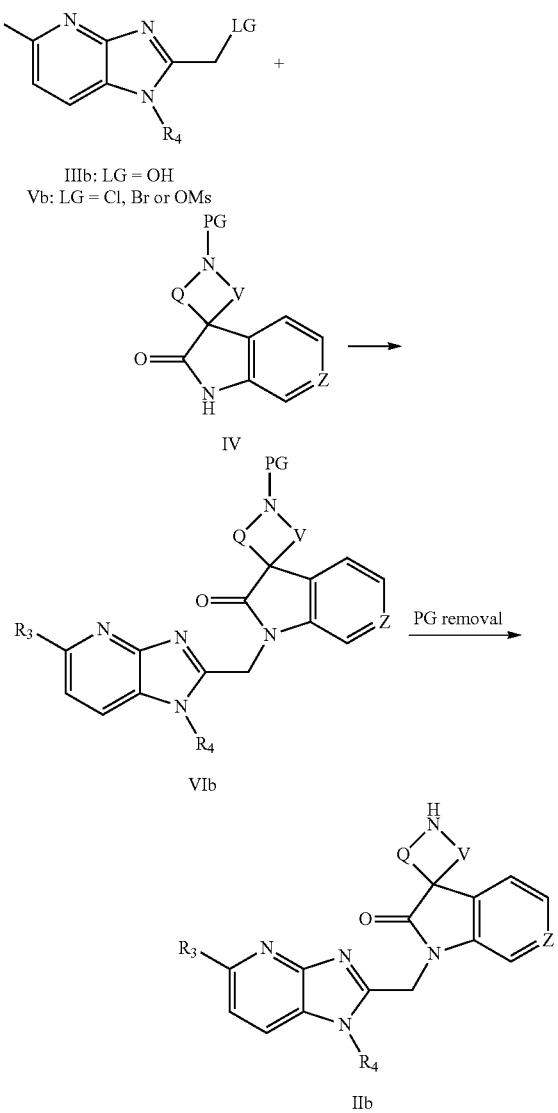

Alternatively compounds of formula (IV) can be prepared, but not limited to, by general procedures illustrated by scheme 6.

The starting material (XIII) can be commercially available or prepared using known in the art procedures. The acid (XIV) can be activated as the Weinreb amide using standard peptide coupling procedures e.g. EDCl/HOBT, HATU, DCC, etc. Once the acid is activated as the ester or Weinreb amide, the aniline (XIII) can be added to convert it to compound (XV).

The introduction of protecting group PG2 on the compound (XV), with PG2 being selected from para-methoxybenzyl, benzyl, tert-butoxycarbonyl, mesyl or tosyl, can be achieved in the presence of a suitable base such as potassium carbonate, cesium carbonate or sodium hydride in a suitable solvent such as DMF or THF and gives compound (XVI). Compound (XVII) was prepared according to the procedure reported in Lee, S. and J. F. Hartwig (2001). J. Org. Chem. 66(10): 3402-3415. The displacement of (U) which is an halo, preferably bromine, using palladium (II) acetate as catalyst in presence of a base such as potassium tert-butoxide and a ligant such as tricyclohexylphosphene in a solvent such as 1,4-dioxane gives compound (XVII). The removal of protecting group in compound (XVII), can be performed using art known procedures yielding compound (IV).

Treatment of the alcohol (Mb) with thionyl chloride provides 2-chloromethyl imidazopyridines (Vb, LG=Cl).

Alternatively, reaction of (Mb) with methane sulfonyl chloride in the presence of an organic base such as triethyl amine or diisopropyl ethyl amine in a suitable solvent such as dichloromethane gives the mesylate derivative (Vb) (LG=OMs) (scheme 8).

Scheme 8: preparation of compound Vb

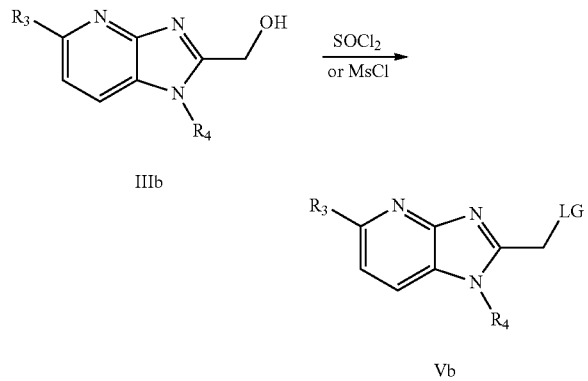

Compounds of formula (IIIa) and (IIIb) are either commercially available or can be prepared, but not limited to, by general procedures illustrated by scheme 9, wherein $R^3$ and $R^4$ are defined as above, and X is CH for the benzimidazoles compounds (IIIa) or N for the azabenzimidazoles (IIIb). Referring to scheme 9 below, haloheteroaryls or haloaryls (XVIII), where (U) is an halide preferably fluorine, can be treated with primary amines in the presence of a suitable base such as potassium carbonate and the like, in a suitable solvent such as ethanol or dichloromethane at a reaction temperature ranging from room temperature to 100° C. to give compounds of formula (XIX). Hydrogenation of the nitro group using well-precedented conditions such as Pd/C, or other catalyst, under hydrogen or Fe/EtOH/CaCl$_2$ can yield diamine of formula (XXII). Alternatively, the hydrogenation of the nitro group of compound (XX) using well-precedented conditions such as Pd/C, or another catalyst, under hydrogen atmosphere or Fe/EtOH/CaCl$_2$ yield diamine of formula (XXI). This can be treated with an aldehyde in the presence of suitable reducing agents such as NaBH(OAc)$_3$, or Na(CN)BH$_3$ in solvents such as methylene chloride, DMF or THF, at about room temperature to give compounds of formula (XXII). The imidazol ring can be formed by treating diamines (XXII) with glycolic acid or an ester like (XXVI) under strong acidic conditions, such as aqueous hydrochloric acid, at elevated temperature such as reflux to yield the alcohols of formula (III).

Alternatively, diamines (XXII) can be condensed with dialkoxyacetate of formula (XXVII), in the presence of acetic acid, in a suitable solvent such as methanol gives the acetal (XXVIII). The acetal of compounds (XXVIII) can be removed with acids such as hydrochloric acid to give the aldehydes of formula (XXIX). The resulting aldehydes of formula (XXIX) can be reduced to alcohols using a suitable reducing agent such as NaBH$_4$ or LiAlH$_4$ in a suitable solvent such as ethanol or THF to yield the desired alcohols of formula (III). In addition, diamines (XXII) can be cyclized with dialkyl oxalate of formula (XXV) in a suitable solvent such as ethanol at elevated temperature with or without microwave heating to produce imidazoles of formula (XXIV). Alternatively, compounds of formula (XXIV) may be prepared in a two steps synthesis starting from diamines (XXII). Firstly diamine (XXII) may be reacted with an alkyl trihaloacetimidate, preferably methyl 2,2,2-trichloroacetimidate, in an acidic media, preferably acetic acid, at a temperature ranging between 25 and 50° C. to yield compound of formula (XXIII). Secondly a reaction of compounds of formula (XXIII) with an inorganic carbonate, preferably sodium carbonate in a suitable solvent such as methanol, lead to compounds of formula (XXIV). Compounds (XXIV) can be subsequently reduced to the desired alcohols of formula (III) using a suitable reducing agent such as NaBH$_4$ or LiAlH$_4$ in a suitable solvent such as ethanol or THF.

Scheme 9: synthetic pathways for the synthesis of compounds of formula (III)

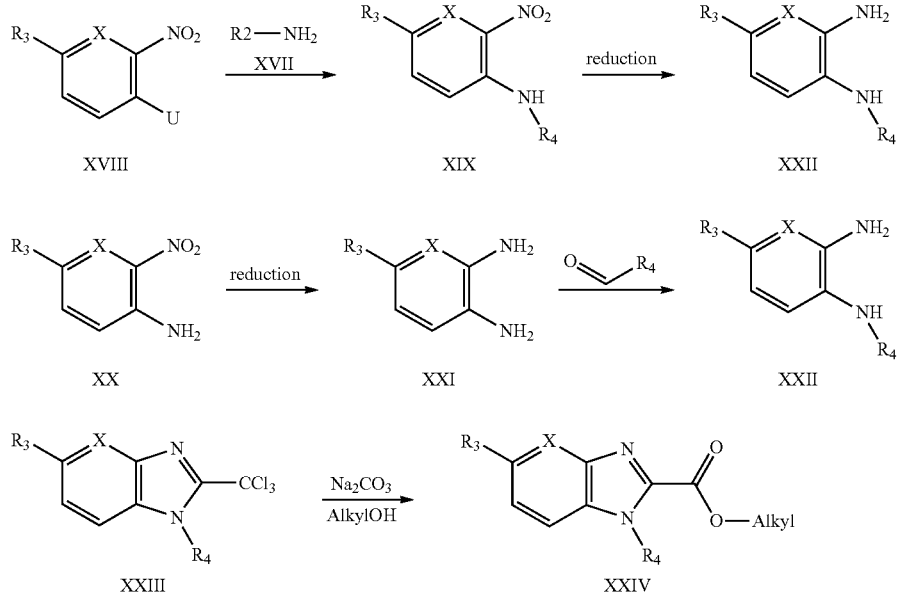

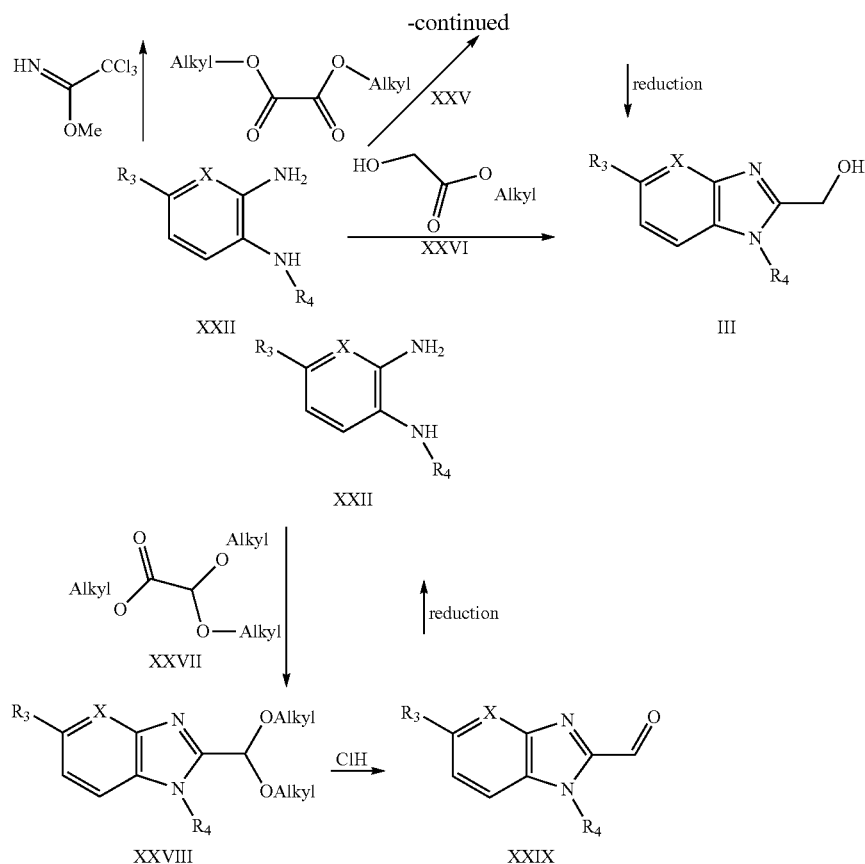

An alternative route for the preparation of compounds of type (III) is depicted in scheme 10. Diamine (XXI) may be first coupled to an alkyl glycolic acid or an ester like (XXVI) under strong acidic conditions, such as aqueous hydrochloric acid, at elevated temperature such as reflux to yield the alcohols of formula (XXX). This alcohol may be protected by a PG, where PG is a protecting group such as, but not limiting to, a trityl which consequently results in compounds (XXXI). A suitable solvent for this type of reactions can be, but not limiting to, dichloromethane. The treatment of compound (XXXI) with compound (XXXII), wherein the LG is a leaving group, such as halide, preferably bromine, or sulfonate, in the presence of a base such as sodium hydride, potassium carbonate or cesium carbonate in a suitable solvent such as DMF or THF, gives compound (XXXIII). The removal of the PG in compound (XXXIII) may be done in the presence of an acid such as hydrochloric acid in the presence of a solvent, not limited to, such as dioxane to yield compound (III).

Scheme 10: synthesis of compounds of formula (III)

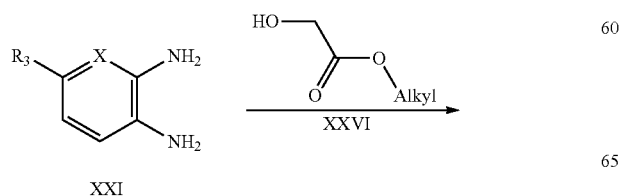

Compounds of formula (Ic), or their pharmaceutically acceptable salts, can be prepared according to the reaction schemes discussed herein below. Unless otherwise indicated, the substituents in the schemes are defined as above. Isolation and purification of the products is accomplished by standard procedures, which are known to a chemist of ordinary skill.

Referring to scheme 11, a compound of formula (IIc), where $R^3$, $R^4$, Q, V and Z are defined as above, can be synthesized by coupling 2-hydroxymethylene indole (IIIc) with (IV) with a method known in the art method such as a Mitsunobu reaction which uses azadiisopropyldicarboxylate and triphenyl phosphine in a suitable solvent such as DMF or THF to give compound (VIc), which is subsequently deprotected using methods known in the art, to give (IIc).

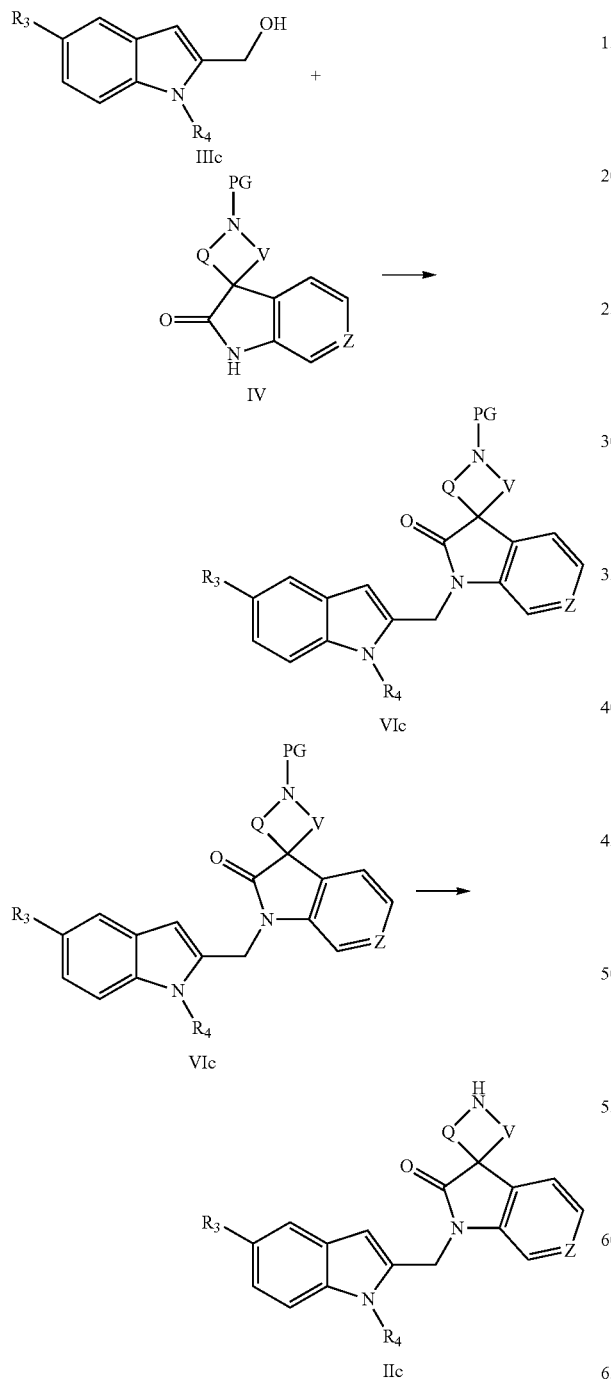

Preparation of Compound IIc

Starting materials (XXXIV) used in this invention are commercially available, or can be synthesized, but not limited to, by methods known in the art such as Reissert synthesis or Fischer synthesis. Reaction of such indoles with $R^4$-LG, where LG is a leaving group such as halide, preferably bromine, or sulfonate, in the presence of a base such as sodium hydride, potassium carbonate or cesium carbonate in a suitable solvent such as DMF or THF, gives compound (XXXV) (scheme 12). The conversion of the alkyl ester of compound (XXXV) to the alcohol (IIIc) can be carried out with metal hydride such as lithium aluminum hydride or sodium borohydride in a suitable solvent such as THF, methanol or ethanol.

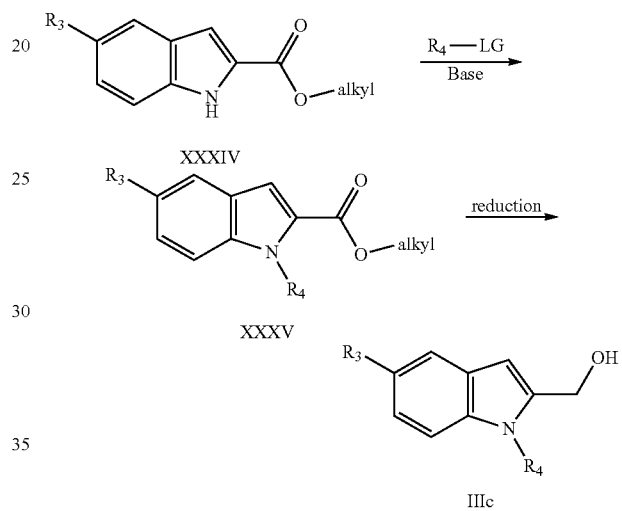

The compounds of Formula (I) may be converted to the corresponding N-oxide forms following art-known procedures for converting a trivalent nitrogen into its N-oxide form. Said N-oxidation reaction may generally be carried out by reacting the starting material of Formula (RI) with appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The compounds of formula (I) may further be prepared by converting compounds of formula (I) into each other according to art-known group transformation reactions.

The starting materials and some of the intermediates are known compounds and are commercially available or may be prepared according to conventional reaction procedures generally known in the art.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. in Antiviral Research, 38, p. 31-42(1998).

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The invention will hereinafter be illustrated with reference to the following, non-limiting examples.

EXPERIMENTAL PART

Abbreviations

| | |
|---|---|
| (ES$^+$) | electrospray ionization, positive mode |
| (M + H)$^+$ | protonated molecular ion |
| aq. | aqueous |
| Boc | tert-butyloxycarbonyl |
| br | broad |
| CDI | 1,1-carbonyl-diimidazole |
| d | doublet |
| DCC | N,N-dicyclohexylcarbodiimide |
| DCM | dichloromethane |
| DIEA | N,N-diisopropylethylamine |
| DIPE | diisopropylether |
| DMAP | 4-dimethylaminopyridine |
| DMF | dimethyl formamide |
| DMSO | dimethyl sulfoxide |
| EDCI | 1-ethyl-3-(3-dimethylaminopropyl)carbodiimide |
| Et | ethyl |
| eq. | equivalent |
| EtOAc | ethyl acetate |
| HATU | 1-[bis(dimethylamino)methylene]-1H-1,2,3-triazolo[4,5-b]pyridinium 3-oxid hexafluorophosphate |
| HOBT | 1-hydroxybenzotriazole |
| KOEt | potassium ethanolate |
| LiHMDS | lithium bis(trimethylsilyl)amide |
| m/z: | mass-to-charge ratio |
| mCPBA | meta-chloroperoxybenzoic acid |
| Me | methyl |
| MeCN | acetonitrile |
| MeOH | methanol |
| EtOH | ethanol |
| MHz | megahertz |
| min | minute(s) |
| N$_2$ | nitrogen |
| NMR | nuclear magnetic resonance (spectroscopy) |
| PCy3 | tricyclohexylphosphine |
| Pd(OAc)2 | palladium (II) acetate |
| Ph | phenyl |
| pTSA | 4-methylbenzenesulfonic acid |
| q | quartet |
| RP HPLC | reverse phase high performance liquid chromatography |
| RT | room temperature |
| s | singlet |
| sat | saturated |
| t | triplet |
| TBDMS | tert-butyldimethylsilyl |
| TFA | trifluoroacetic acid |
| THF | tetrahydrofuran |

NMR

For a number of compounds, $^1$H NMR spectra were recorded on a Bruker DPX-400 spectrometer operating at 400 MHz or on a Bruker DPX-360 operating at 360 MHz using chloroform-d (deuterated chloroform, CDCl$_3$) or DMSO-d$_6$ (deuterated DMSO, dimethyl-d6 sulfoxide) as solvent. Chemical shifts (δ) are reported in parts per million (ppm) relative to tetramethylsilane (TMS), which was used as internal standard.

Intermediate 1f: Synthesis of tert-butyl 2'-oxospiro[azetidine-3,3'-indoline]-1-carboxylate

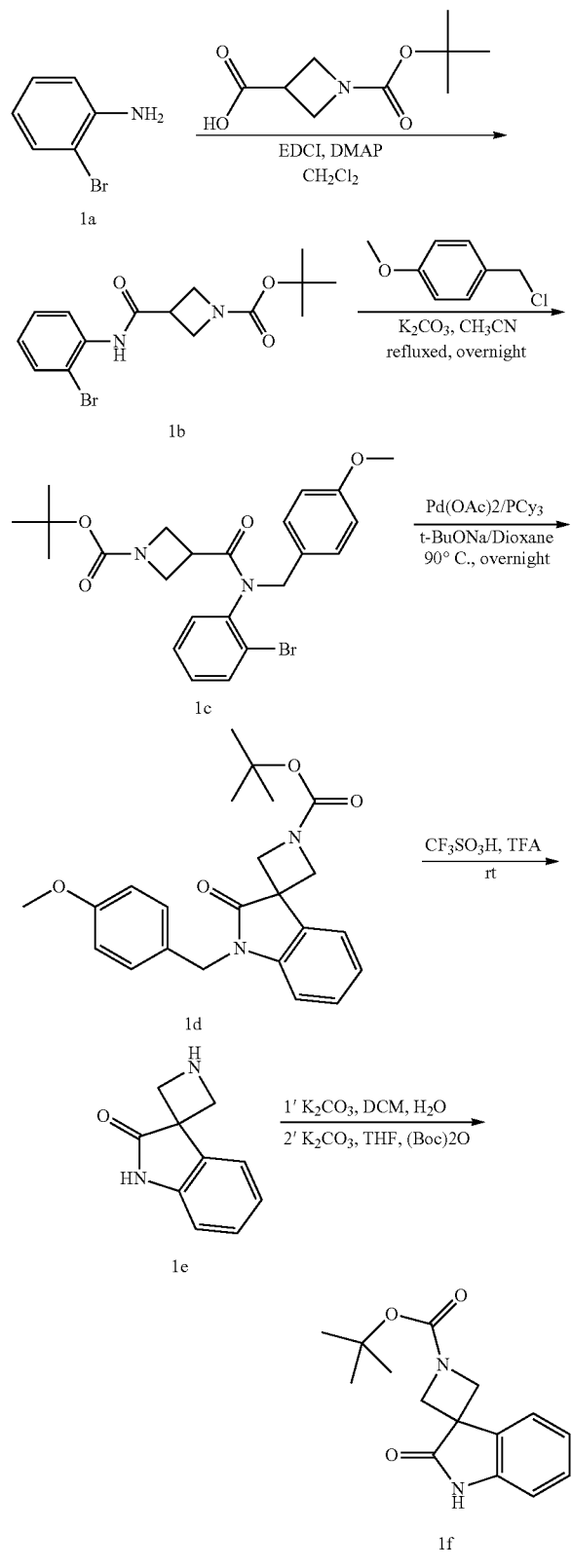

Step 1

To a stirred solution of 2-bromoaniline (150 g, 872 mmol, 1 eq.) and DMAP (138.5 g, 1133 mmol, 1.3 eq.) in $CH_2Cl_2$ (2500 ml) was added N-(tert-butoxycarbonyl)azetidine-3-carboxylic acid (872 mmoles, 1 eq) in one portion followed by the addition of EDCI (217 g, 1133 mmol, 1.3 eq.) in one portion at room temperature. The resulting mixture was stirred at room temperature overnight. It was then successively washed with 10% citric acid aqueous solution, water, saturated $Na_2CO_3$ aqueous solution, and brine, and dried over $Na_2SO_4$. After filtration, the solvent was removed under vacuum to give tert-butyl 3-((2-bromophenyl)carbamoyl) azetidine-1-carboxylate (1b) (328 g, 85% yield).

Step 2

A mixture of tert-butyl 3-((2-bromophenyl)carbamoyl) azetidine-1-carboxylate (1b) (307 g, 864 mmol, 1 eq.), 4-methoxybenzylchloride (203 g, 1296 mmol, 1.5 eq.) and $K_2CO_3$ (358 g, 2593 mmol, 3 eq.) in $CH_3CN$ (3000 ml) was refluxed overnight. The solution was then filtered, and the solid was washed with $CH_3CN$ (1000 ml). The filtrate was concentrated under vacuum and the crude product was triturated in petroleum ether/ethyl acetate (30:1) to give tert-butyl 3-((2-bromophenyl)(4-methoxybenzyl)carbamoyl)azetidine-1-carboxylate (1c) (380 g, 90% yield).

Step 3

$Pd(OAc)_2$ (2.25 g, 10 mmol, 0.025 eq.) and $PCy_3$ (2.8 g, 10 mmol, 0.025 eq.) were added to the solution of tert-butyl 3-((2-bromophenyl)(4-methoxybenzyl)carbamoyl) azetidine-1-carboxylate (1c) (190 g, 400 mmol, 1 eq.) and t-BuONa (57.6 g, 600 mmol, 1.5 eq.) in dioxane (960 ml) under $N_2$ atmosphere. The reaction was stirred at 90° C. overnight under $N_2$ atmosphere. The solution was then filtered and concentrated under vacuum. The residue was dissolved in $CH_2Cl_2$, washed with $NH_4Cl$, then brine and dried over $Na_2SO_4$. The solvent was removed under vacuum to give 158 g (quantitative yield) of tert-butyl 1'-(4-methoxybenzyl)-2'-oxospiro[azetidine-3,3'-indoline]-1-carboxylate (1d).

Step 4

$CF_3SO_3H$ (119 ml, 1350 mmol, 3 eq.) was added to a mixture of tert-butyl 1'-(4-methoxybenzyl)-2'-oxospiro[azetidine-3,3'-indoline]-1-carboxylate (1d) (178 g, 450 mmol, 1 eq. crude) in TFA (750 ml). The mixture was stirred overnight at 25° C. The solvent was then removed under vacuum and the residue (78.4 g) was used directly in the next step.

Step 5

A solution of spiro[azetidine-3,3'-indolin]-2'-one (1e) (78.4 g, 450 mmol, 1 eq. crude) in $CH_2Cl_2$ (1500 ml) was poured into a mixture of $K_2CO_3$ (186.6 g, 1350 mmol, 3 eq.) in ice water (1500 ml). The aqueous layer was separated and washed with $CH_2Cl_2$ (3×500 mL). The aqueous layer was diluted in THF (1500 ml) and $(Boc)_2O$ (98.2 g, 450 mmol, 1 eq.) was added. The solution was stirred overnight. 500 mL of a solution of ammonia in MeOH (7M) was then added dropwise to the above solution. The organic solvent was evaporated under vacuum. The aqueous solution was extracted with $CH_2Cl_2$ (800 ml×3), washed with brine, dried over $Na_2SO_4$, filtered and then concentrated under vacuum.

The resulting residue was washed with tert-butyl methyl ether to give the pure product ter t-butyl 2'-oxospiro[azetidine-3,3'-indoline]-1-carboxylate (1f) (44 g, 37% yield).

¹H-NMR (400 MHz, DMSO-d6) δ ppm 2.14 (t, J=7.5 Hz, 2H), 2.96 (s, 3H), 3.11-3.23 (m, 2H), 4.32 (t, J=7.4 Hz, 2H), 4.65 (d, J=5.3 Hz, 2H), 5.34 (t, J=5.5 Hz, 1H), 6.39 (s, 1H), 7.14 (dd, J=8.7, 1.9 Hz, 1H), 7.47-7.61 (m, 2H).

Intermediate 2g Synthesis of tert-butyl 2'-oxo-1',2'-dihydrospiro[piperidine-4,3'-pyrrolo[2,3-c]pyridine]-1-carboxylate

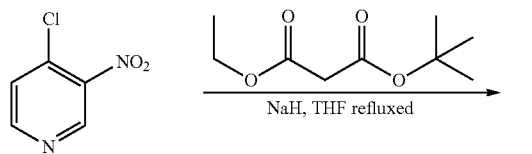

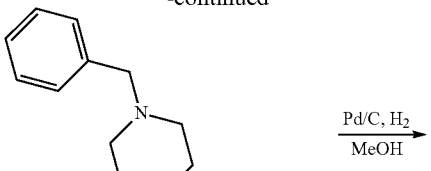

Step 1

To a solution of tert-butyl ethyl malonate (160 g, 850 mmol) in THF (1600 ml) was added NaH (80 g, 2118 mmol) portionwise at 0° C. The mixture was stirred for 1 hour at 15° C., then 4-chloro-3-nitropyridine (112 g, 706 mmol) was added portionwise at 0° C. The mixture was stirred for 1 hour at 15° C. The reaction was quenched with water and 1N HCl was added until pH=5. The mixture was extracted with ethyl acetate twice. The organic layers were washed with brine, dried and evaporated under vacuum to give 1-(tert-butyl) 3-ethyl 2-(3-nitropyridin-4-yl)malonate (2a) (250 g), which was used without further purification in the next step.

Step 2

To a solution of 1-(tert-butyl) 3-ethyl 2-(3-nitropyridin-4-yl)malonate (2a) (crude, 250 g, 706 mmol) in CH₂Cl₂ (1500 ml) was added TFA (250 mL). After 14 hours of stirring at 60° C., the mixture was evaporated. A 10% NaHCO₃ aqueous solution was then added and the mixture was extracted with ethyl acetate twice. The organic layers were washed with brine, dried and evaporated under vacuum to give ethyl 2-(3-nitropyridin-4-yl)acetate (2b) (180 g), which was used without further purification in the next step.

Step 3: Synthesis of ethyl 2-(3-aminopyridin-4-yl)acetate (intermediate 2c)

A mixture of ethyl 2-(3-nitropyridin-4-yl)acetate (2b) (65 g, 309 mmol, 90% purity, 1 eq.) in methanol (1500 ml) was hydrogenated at 20° C. (atmospheric pressure) with 10% Pd/C (6.5 g) as a catalyst for 16 h. After uptake of hydrogen (3 eq.), the catalyst was filtered off and the filtrate was evaporated under vacuum to give 50 g (yield: 90%) of ethyl 2-(3-aminopyridin-4-yl)acetate (2c), which was used without further purification in the next step.

Step 4: Synthesis of 1,3-dihydro-2H-pyrrolo[2,3-c]pyridin-2-one (intermediate 2d)

Ethyl 2-(3-aminopyridin-4-yl)acetate (2c) (34 g, 189 mmol, 1 eq.) was dissolved in 1.4 N HCl (1000 ml) and diisopropyl ether (1000 ml). The mixture was stirred at room temperature overnight. The organic layer was separated and washed with $H_2O$. The combined aqueous layers were washed with $CH_2Cl_2$ and evaporated to almost dryness. The resulting precipitate was filtered off and dried (vacuum, 60° C., 2 hours) to give 26 g (yield: 94%) of 1,3-dihydro-2H-pyrrolo[2,3-c]pyridin-2-one (2d) as a hydrochloric acid salt.

Step 5: Synthesis of 1-benzylspiro[piperidine-4,3'-pyrrolo[2,3-c]pyridin]-2'(1'H)-one (intermediate 2e)

The hydrochloric acid salt 1,3-dihydro-2H-pyrrolo[2,3-c]pyridin-2-one (2d) (160 g, 938 mmol, 1 eq.) was added to 1M LiHMDS solution in THF (3751 ml, 3751 mmol, 4 eq.) at −78° C. After warming up to 0° C., N-benzyl-2-chloro-N-(2-chloroethyl)ethan-1-amine hydrochloride (218 g, 938 mmol, 1 eq.) was added. The mixture was warmed to 20° C., then refluxed overnight. After cooling down to room temperature, the reaction mixture was successively quenched with a 10% $NH_4Cl$ solution (300 ml) and extracted with ethyl acetate (2×300 ml). The combined organic layers were washed with brine, dried ($Na_2SO_4$), filtered and the solvent was evaporated under vacuum. The residue was purified by column chromatography over silica gel (eluent: $CH_2Cl_2$: methanol from 1:0 to 10:1) to give 70 g (23% yield) of 1-benzylspiro[piperidine-4,3'-pyrrolo[2,3-c] pyridin]-2' (1'H)-one (2e).

Step 6: Synthesis of spiro[piperidine-4,3'-pyrrolo[2,3-c]pyridin]-2'(1'H)-one (intermediate 2f)

A mixture of 1-benzylspiro[piperidine-4,3'-pyrrolo[2,3-c]pyridin]-2'(1'H)-one (2e) (70 g, 238.61 mmol, 1 eq.) in methanol (1000 ml) was hydrogenated at 50° C. (50 psi) with 10% Pd/C (50 g) as a catalyst for 15 hours. The catalyst was filtered off and the solvent was evaporated under vacuum. The residue was purified by flash column chromatography over silica gel (eluent: $CH_2Cl_2$/ethyl acetate from 1/0 to 0/1) to give 50 g (93% yield) of spiro[piperidine-4,3'-pyrrolo[2,3-c]pyridin]-2'(1'H)-one (2f).

Step 7: Synthesis of tert-butyl 2'-oxo-1',2'-dihydrospiro[piperidine-4,3'-pyrrolo[2,3-c]pyridine]-1-carboxylate (intermediate 2g)

To a solution of spiro[piperidine-4,3'-pyrrolo[2,3-c]pyridin]-2'(1'H)-one (2f) (50 g, 246.05 mmol, 1 eq.) in MeOH (1000 ml) was added $Boc_2O$ (64.43 g, 295.22 mmol, 1.2 eq.). The mixture was stirred at room temperature overnight, then evaporated till dryness. The residue was purified by column chromatography over silica gel (eluent: dichloromethane:ethyl acetate from 1:0 to 0:1) to give 43.32 g (58% yield) of tert-butyl 2'-oxo-1',2'-dihydrospiro[piperidine-4,3'-pyrrolo[2,3-c]pyridine]-1-carboxylate (2g).

Intermediate 3d: Synthesis of 3-(methylsulfonyl)propan-1-amine hydrochloride

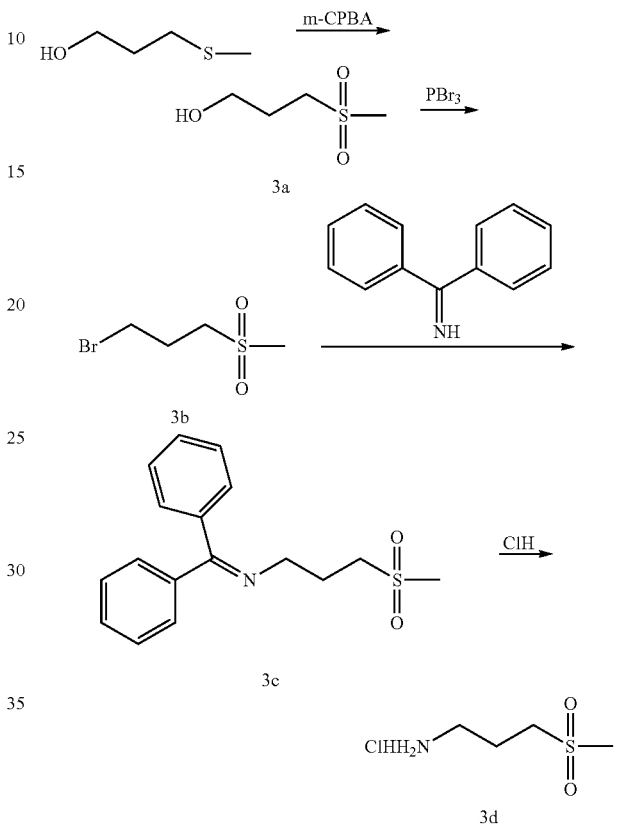

Step 1: Synthesis of 3-(methylsulfonyl)propan-1-ol (intermediate 3a)

3-(Methylthio)propan-1-ol (200 g, 1900 mmol) was dissolved in $CH_2Cl_2$ (2000 mL). The mixture was cooled to 0° C., then m-CPBA 85% in water (970 g, 5700 mmol) was added portion wise keeping the temperature between 0 and 5° C. After addition, the mixture was allowed to warm to 25° C. and stirred for 15 hours. The mixture was filtered through a celite pad and the filtrate was purified by flash column (eluent: petroleum ether:ethyl acetate=3:1 and then ethyl acetate:methanol=10:1) to yield the intermediate (3a) (75 g, 29%).

Step 2: Synthesis of 1-bromo-3-(methylsulfonyl)propane (intermediate 3b)

To a solution of the intermediate (3a) (75 g, 543 mmol) in $CH_2Cl_2$ (750 mL), at 0° C., was added dropwise phosphorus tribromide (53.6 mL, 570 mmol), keeping the temperature between 0 and 5° C. After addition, the mixture was allowed to warm to 25° C. and stirred for 15 hours. The mixture was poured into ice-water, the organic layer was then separated, washed with brine (2×500 mL), dried over $Na_2SO_4$, filtered and evaporated under vacuum to yield the title compound (3b) (77 g, 71%). $^1$H NMR (400 MHz, chloroform-d) δ ppm 2.25 2.40 (m, 2H) 2.91 (s, 3H) 3.1-3.2 (m, 2H) 3.5-3.6 (m, 2H).

Step 3: Synthesis of N-(diphenylmethylene)-3-(methylsulfonyl)propan-amines (intermediate 3c)

To a solution of the intermediate (3b) (27 g, 134 mmol) in CH$_3$CN (60 mL) were added diphenylmethanimine (27 g, 148 mmol) and DIEA (19.6 g, 152 mmol). The mixture was refluxed for 4 hours and then cooled to room temperature. The mixture was then neutralized with 50% aqueous acetic acid at 25° C. Water (80 mL) was added and the mixture was extracted with ethyl acetate (2×300 mL). The combined organic layers were washed with brine, dried over Na$_2$SO$_4$, filtered and evaporated under vacuum. The residue was washed with petroleum ether (4×100 mL). The mixture was treated with methyl tert-butyl ether. The solid was collected and washed with petroleum ether. The filtrate was dried under vacuum and the resulting residue was purified by column chromatography (eluent: CH$_2$Cl$_2$: ethyl acetate from 1:0 to 10:1) to give the title compound (3c) (34 g, 85%) as a white solid.

Step 4: Synthesis of 3-(methylsulfonyl)propan-1-amine hydrochloride (intermediate 3d)

To a solution of the intermediate 3c (34 g, 113 mmol) in dioxane (600 mL) was added a solution of 4N HCl/dioxane (120 mL, 480 mmol) dropwise at 0° C. After addition, the mixture was allowed to warm to 25° C. and stirred for 15 hours. The mixture was filtered. The solid was collected and washed with dioxane to give the title product (3d) (11.5 g, 50%) as a yellow powder.

Intermediate 4b Synthesis of (5-chloro-1-(3-(methylsulfonyl)propyl)-1H-indol-2-yl)methanol

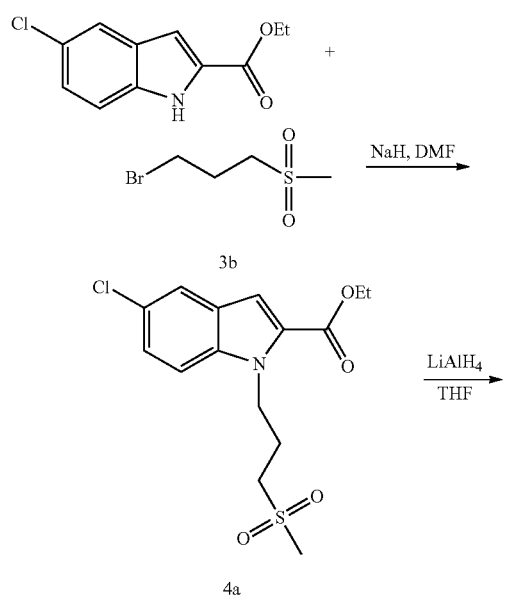

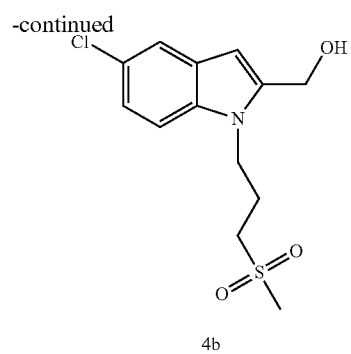

Step 1: Synthesis of ethyl 5-chloro-1-(3-(methylsulfonyl)propyl)-1H-indole-2-carboxylate (intermediate 4a)

Ethyl 5-bromo-1H-indole-2-carboxylate (2.3 g, 8.6 mmol) was dissolved in DMF (50 mL). The mixture was stirred at room temperature, then sodium hydride 60% suspension in mineral oil (0.52 g, 12.8 mmol) was added. The resulting mixture was stirred at room temperature for 1 hour, then 1-bromo-3-(methylsulfonyl)propane (3b) (2.6 g, 12.8 mmol) was added. The resulting mixture was stirred at room temperature overnight. The mixture was poured in ice/water solution and extracted with ethyl acetate. The organic layer was dried over MgSO$_4$ and concentrated to yield a brown crude oil. The crude was purified by column chromatography using dichloro-methane/methanol to yield the title compound ethyl 5-chloro-1-(3-(methylsulfonyl)propyl)-1H-indole-2-carboxylate (4a) (3.2 g, 96%) as a white solid.

m/z=344 (M+H)$^+$.

Step 2: Synthesis of (5-chloro-1-(3-(methylsulfonyl)propyl)-1H-indol-2-yl)methanol (intermediate 4b)

To a solution of intermediate (4a) (3.2 g, 8.24 mmol) in THF (100 mL) was added at room temperature lithium aluminum hydride (2 M solution in THF, 5.2 mL, 10.4 mmol). The resulting mixture was stirred at room temperature overnight. The reaction mixture was quenched by addition of ethyl acetate and ethanol. The resulting mixture was poured in ice/water solution then filtered on celite. The aqueous layer was extracted with ethyl acetate (3×50 mL). The combined organic extracts were washed with brine (100 mL), dried over MgSO$_4$, filtered and concentrated under reduced pressure. The residue was purified by column chromatography using dichloromethane/methanol as the eluent to give the desired product (5-chloro-1-(3-(methylsulfonyl) propyl)-1H-indol-2-yl)methanol (4b) (2.5 g, 88%) as a white solid.

m/z=302 (M+H)$^+$.

Intermediate 5c Synthesis of 4-(5-chloro-2-(hydroxymethyl)-1H-indol-1-yl)-butanenitrile

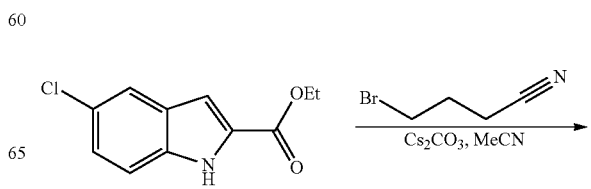

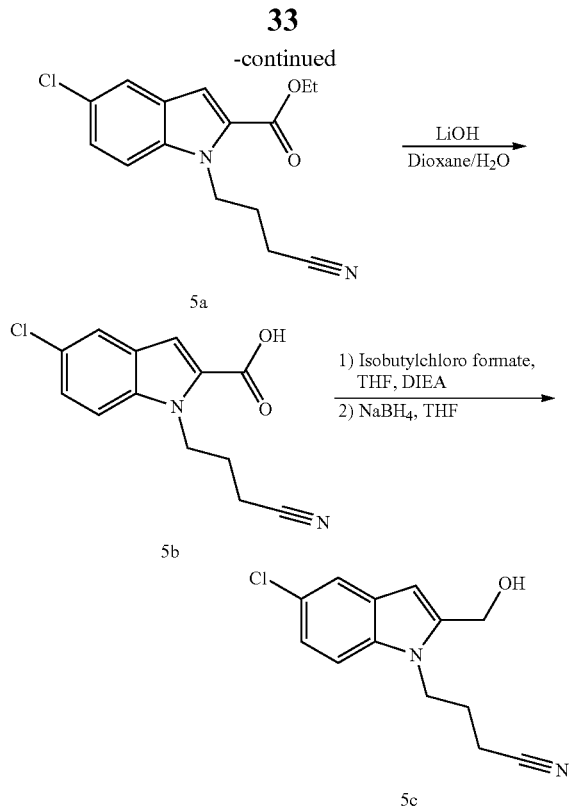

Step 1: Synthesis of ethyl 5-chloro-1-(3-cyanopropyl)-1H-indole-2-carboxylate (intermediate 5a)

Ethyl-5-chloroindol-2-carboxylate (33.55 g, 150 mmol) was dissolved in acetonitrile (600 mL) and stirred at room temperature. Then cesium carbonate (73.31 g, 225 mmol) was added and stirring was continued for 30 minutes. 4-Bromobutyronitrile (18.83 mL, 180 mmol) was added in small portions over a period of one hour and stirring was continued overnight at ambient temperature. The reaction mixture was filtered and the filtrate was evaporated to dryness. The residue was dissolved in dichloromethane and washed with water. The organic layer was dried over MgSO$_4$, filtered and evaporated to give 43.5 g (99% yield) of ethyl 5-chloro-1-(3-cyanopropyl)-1H-indole-2-carboxylate (5a), which was used as such in the next step.

m/z=290 (M+H)$^+$.

Step 2: Synthesis of 5-chloro-1-(3-cyanopropyl)-1H-indole-2-carboxylic acid (intermediate 5b)

Ethyl 5-chloro-1-(3-cyanopropyl)indol-2-carboxylate (5a) (43.61 g, 149.97 mmol) was dissolved in 1,4-dioxane (850 mL) and stirred at room temperature. Then a solution of lithium hydroxide (10.78 g, 450 mmol) in distilled water (150 mL) was added. After stirring overnight at room temperature, the reaction mixture was evaporated to dryness. The residue was dissolved in 500 mL water and neutralised with aqueous hydrochloric acid 1 N (450 mL). The white precipitate was filtered off and dried in vacuo to yield 39.8 g (quantitative yield) of 5-chloro-1-(3-cyanopropyl)-1H-indole-2-carboxylic acid (5b).

m/z=262 (M+H)$^+$.

Step 3: Synthesis of 4-(5-chloro-2-(hydroxymethyl)-1H-indol-1-yl)butanenitrile (intermediate 5c)

5-chloro-1-(3-cyanopropyl)indol-2-carboxylic acid (5b) (39.4 g, 149.98 mmol) and Hunigs base (51.69 mL, 300 mmol) were dissolved in tetrahydrofuran (550 mL) and stirred at −10° C. under a nitrogen atmosphere. Then a solution of isobutylchloroformate in tetrahydrofuran (50 ml) was added dropwise and the stirring was continued for one hour at −10° C. and one hour at ambient temperature. Then sodium borohydride (17.02 g, 450 mmol) was added portion wise at −10° C. and stirred for one hour, afterwards distilled water (200 mL) was added cautiously to the reaction mixture and stirring was continued for another hour at room temperature under a nitrogen atmosphere. The mixture was neutralised with 10% citric acid in water and then extracted with ethyl acetate. The organic layer was dried over MgSO$_4$, filtered and evaporated. The residue was purified over silica with heptane/dichloromethane/methanol 50/50/0–>0/100/0–>0/99/1 as gradient. The corresponding fractions were evaporated to yield 23.9 g (64% yield) of 4-(5-chloro-2-(hydroxymethyl)-1H-indol-1-yl)butanenitrile (5c) as a white powder.

m/z=248 (M+H)$^+$.

Intermediate 6e Synthesis of 5-chloro-2-(chloromethyl)-1-(3-(methylsulfonyl)-propyl)-1H-benzo[d]imidazole hydrochloride

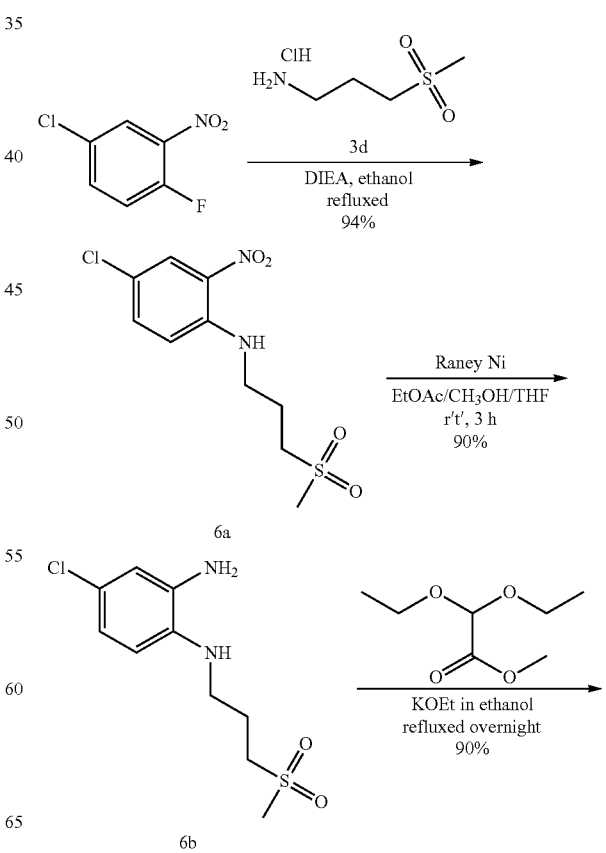

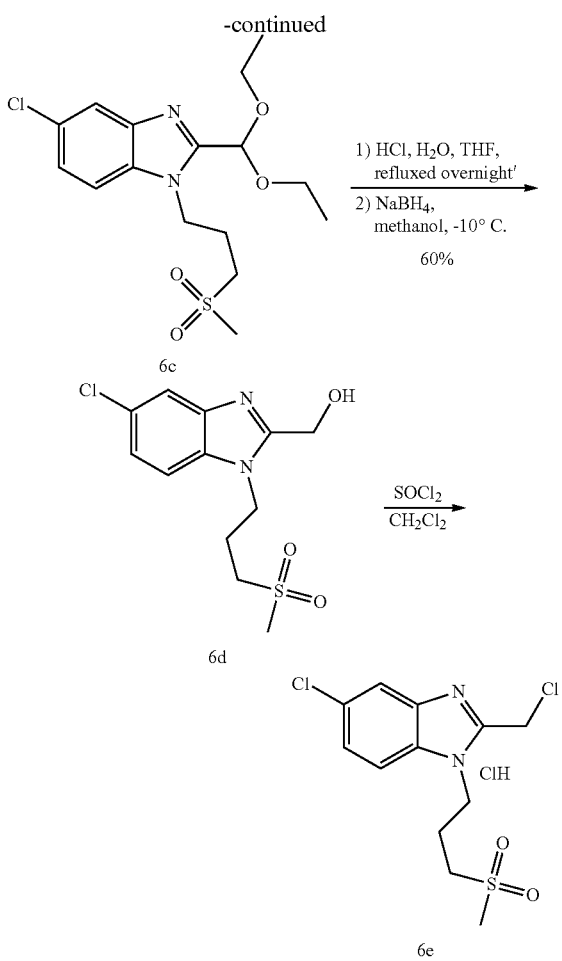

Step 1: Synthesis of 4-chloro-N-(3-(methylsulfonyl)propyl)-2-nitroaniline (6a)

A solution of 1-chloro-4-chloro-3-nitrobenzene (7.6 g, 35 mmol), 3-(methylsulfonyl)-propan-1-amine hydrochloride (3d) (6 g, 35 mmol) and diisopropylethylamine (DIEA) (13.5 g, 105 mmol) in ethanol (70 mL) was refluxed for 14 h. The mixture was then cooled to 20° C. and the resulting precipitate was filtered and washed with ethanol. 11 g (94%) of intermediate (6a) was obtained as an orange powder.

Step 2: Synthesis of 4-chloro-N1-(3-(methylsulfonyl)propyl)benzene-1,2-diamine (6b)

Intermediate (6a) (10 g, 29.7 mmol) in methanol (200 mL), EtOAc (200 mL) and THF (200 mL) was hydrogenated with Raney Ni (10 g) as a catalyst at 20° C. (1 atm) for 3 h. After uptake of hydrogen (3 eq.), the catalyst was filtered off and the filtrate was evaporated. 10 g (90%) of intermediate (6b) was obtained as a black solid.

Step 3: Synthesis of 5-chloro-2-(diethoxymethyl)-1-(3-(methylsulfonyl)propyl)-1H-benzo[d]imidazole (6c)

Intermediate (6b) (10 g, 29.7 mmol) and methyl dimethoxyacetate (9.2 g, 68.31 mmol) in 24 wt % KOEt in ethanol (13.5 g, 38.5 mmol) were stirred and refluxed overnight. The mixture was evaporated under vacuum. Water (200 mL) was then added, followed by acetic acid to neutralize the mixture. The mixture was extracted with ethyl acetate (2×100 mL). The combined organic layers were washed with saturated NaHCO$_3$, brine and dried over Na$_2$SO$_4$. The solvent was removed under vacuum to yield 12.3 g (90%) of intermediate (6c) as a dark oil.

Step 4: Synthesis of (5-chloro-1-(3-(methylsulfonyl)propyl)-1H-benzo[d]imidazol-2-yl)methanol (6d)

Intermediate (6c) (12.3 g, 29.3 mmol) in THF (100 mL) was stirred for 0.5 h at 20° C. until complete dissolution. Conc. HCl (21 mL) and H$_2$O (42 mL) were then added. The mixture was refluxed for 6 h and then cooled to −10° C. CH$_3$OH (50 mL) was added, followed by careful addition of NaBH$_4$ (24 g, 629 mmol). The mixture was stirred for 0.5 hours at 10° C. and concentrated under vacuum. Water (200 mL) was added. The mixture was extracted with ethyl acetate (2×100 mL). The combined organic layers were washed with brine and dried over Na$_2$SO$_4$. The solvent was removed under vacuum. The resulting solid was washed with ethyl acetate (2×5 mL) and dried under vacuum. 6.8 g (60%) of intermediate (6d) was obtained as an off-white solid.

$^1$H NMR (400 MHz, DMSO-d$_6$) δ ppm 2.20 (dq, J=7.8, 7.5 Hz, 2H), 2.98 (s, 3H), 3.16-3.24 (m, 2H), 4.42 (t, J=7.4 Hz, 2H), 4.73 (d, J=6.0 Hz, 2H), 5.73 (t, J=5.8 Hz, 1H), 7.42 (dd, J=8.7, 1.9 Hz, 1H), 7.63 (d, J=8.5 Hz, 1H), 7.79-7.83 (m, 1H).

Step 5: Synthesis of 5-chloro-2-(chloromethyl)-1-(3-methylsulfonylpropyl)benzimidazole hydrochloride (6e)

To a solution of alcohol 6d (363 mg, 1.414 mmole) in 30 mL of dichloromethane was added drop wise a solution of thionyl chloride (336 mg, 2 eq) in 10 mL of dichloromethane. The reaction mixture was stirred for one hour at 45° C. It was then concentrated under vacuum to give the desired intermediate 6e (440 mg, 99%) as an HCl salt, which was used as such in the next step.

Intermediate 7c Synthesis of 4-(5-chloro-2-(chloromethyl)-1H-benzo[d]imidazol-1-yl)butanenitrile hydrochloride

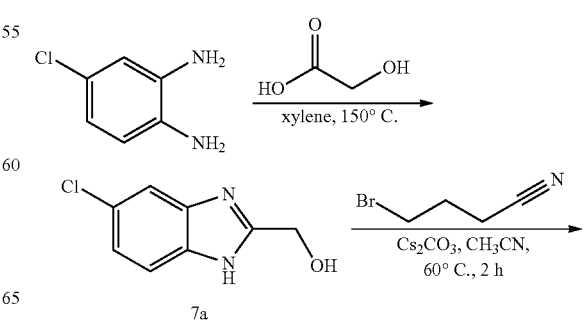

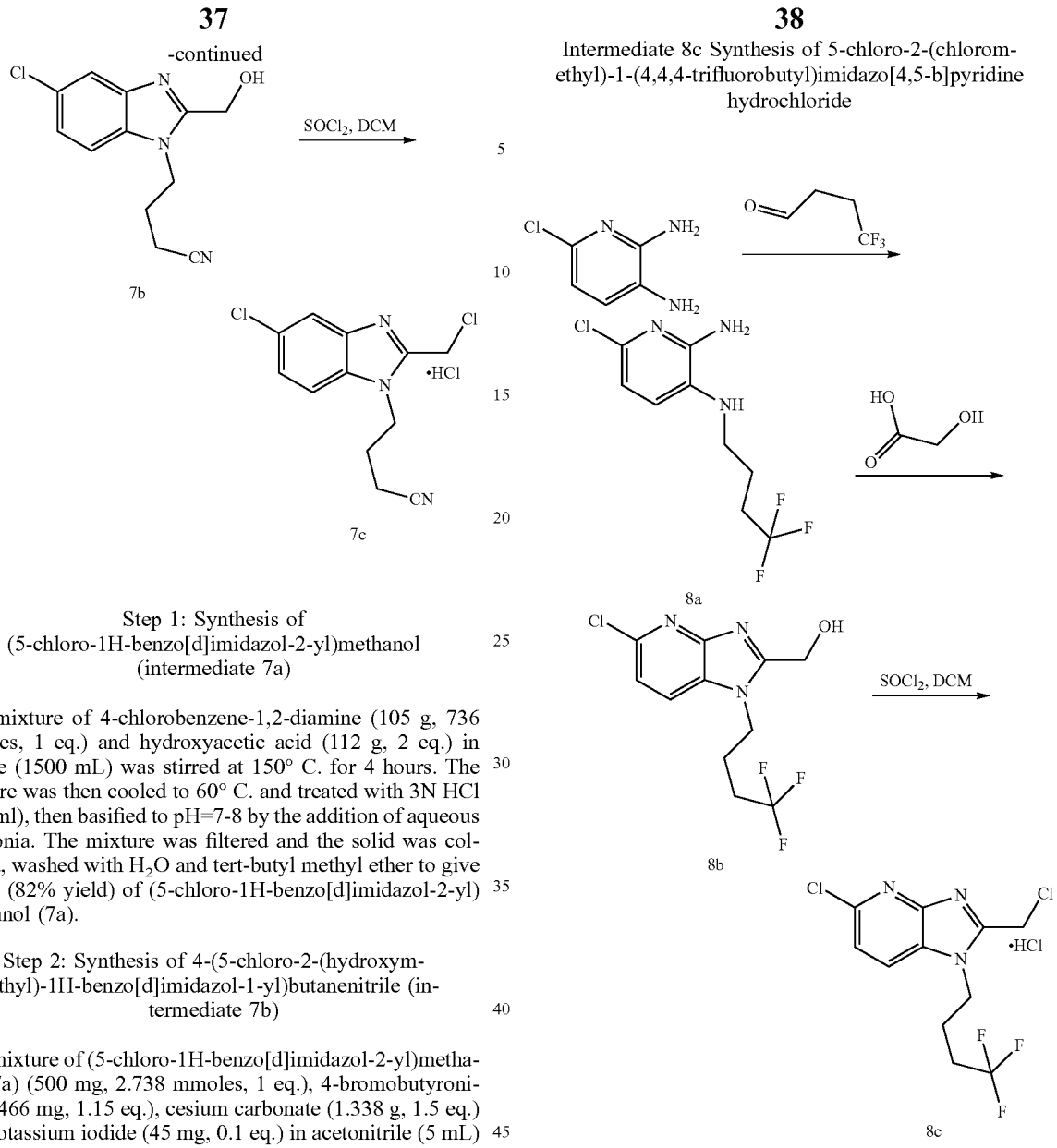

Step 1: Synthesis of (5-chloro-1H-benzo[d]imidazol-2-yl)methanol (intermediate 7a)

A mixture of 4-chlorobenzene-1,2-diamine (105 g, 736 mmoles, 1 eq.) and hydroxyacetic acid (112 g, 2 eq.) in xylene (1500 mL) was stirred at 150° C. for 4 hours. The mixture was then cooled to 60° C. and treated with 3N HCl (480 ml), then basified to pH=7-8 by the addition of aqueous ammonia. The mixture was filtered and the solid was collected, washed with $H_2O$ and tert-butyl methyl ether to give 123 g (82% yield) of (5-chloro-1H-benzo[d]imidazol-2-yl)methanol (7a).

Step 2: Synthesis of 4-(5-chloro-2-(hydroxymethyl)-1H-benzo[d]imidazol-1-yl)butanenitrile (intermediate 7b)

A mixture of (5-chloro-1H-benzo[d]imidazol-2-yl)methanol (7a) (500 mg, 2.738 mmoles, 1 eq.), 4-bromobutyronitrile (466 mg, 1.15 eq.), cesium carbonate (1.338 g, 1.5 eq.) and potassium iodide (45 mg, 0.1 eq.) in acetonitrile (5 mL) was refluxed overnight. The mixture was then cooled and filtered. The filtrate was evaporated under vacuum and the residue was treated with ethyl acetate (30 ml) and brine (20 ml). The separated organic layer was dried ($Na_2SO_4$), filtered and the solvent was evaporated under vacuum. The residue was purified by column chromatography (eluent: $CH_2Cl_2$:methanol from 1:0 to 15:1) to yield 732 mg (54%) of a mixture containing two regio-isomers (5- and 6-chloro derivatives) in a 1/1 ratio. This mixture was further separated by SFC to provide the pure regio-isomer (7b).

Step 3: Synthesis of 4-(5-chloro-2-(chloromethyl)-1H-benzo[d]imidazol-1-yl)butanenitrile hydrochloride (7c)

To a solution of alcohol (7b) (1 g, 4.005 mmole) in 50 mL of dichloromethane was added drop wise a solution of thionyl chloride (631 µL, 2 eq.) in 10 mL of dichloromethane. The reaction mixture was stirred for one hour at 45° C. It was then concentrated under vacuum to give the desired intermediate (7c) (1.2 g, 99% yield) as an HCl salt, which was used as such in the next step.

Intermediate 8c Synthesis of 5-chloro-2-(chloromethyl)-1-(4,4,4-trifluorobutyl)imidazo[4,5-b]pyridine hydrochloride

Step 1: 6-chloro-$N^3$-(4,4,4-trifluorobutyl)-pyridine-2,3-diamine (intermediate 8a)

6-chloropyridine-2,3-diamine (5 g, 34.82 mmol) was dissolved in dichloromethane (200 mL), acetic acid (20 drops) and 4,4,4-trifluorobutanal (4.38 g, 34.8 mmol) were added. The resulting mixture was stirred for 30 minutes and then sodium triacetoxyhydroborate (22.14 g, 104.5 mmol) was added. The reaction mixture was stirred at room temperature overnight and a solution of 50% $Na_2CO_3$ was added dropwise until gas evolution stopped. The organic layer was separated, dried on $MgSO_4$, filtrated and evaporated to dryness. The residue was purified by column chromatography using heptane/EtOAc 7/3 to pure EtOAc. Intermediate 6-chloro-$N^3$-(4,4,4-trifluorobutyl)-pyridine-2,3-diamine (8a) was recovered as a white solid and dried in vacuo overnight (6.16 g, 70%).

m/z=254 $(M+H)^+$.

Step 2: Synthesis of (5-chloro-1-(4,4,4-trifluorobutyl)-1H-imidazo[4,5-b]pyridin-2-yl)methanol (intermediate 8b)

A mixture of intermediate (8a) (5.68 g, 22.46 mmol) and 2-hydroxyacetic acid (4.27 g, 56.2 mmol) was stirred at 150° C. for 4 hours. The mixture was allowed to cool down to room temperature and treated carefully with 3N hydrochloric acid. The resulting mixture was made basic with aqueous ammonia and extracted with $CH_2Cl_2$ (300 mL). The organic layer was dried over $MgSO_4$ and evaporated to dryness. The residue was purified by column chromatography on silica using $CH_2Cl_2$ to EtOAc to give 4.27 g (65%) of (5-chloro-1-(4,4,4-trifluorobutyl)-1H-imidazo[4,5-b]pyridin-2-yl)methanol (8b) as a brown solid.

m/z=294 (M+H)$^+$. $^1$H NMR (400 MHz, chloroform-d) δ ppm 1.00 (s, 2H), 1.12-1.23 (m, 2H), 1.83-1.99 (m, 2H), 2.12-2.31 (m, 2H), 2.91 (spt, J=3.50 Hz, 1H), 4.38-4.54 (m, 2H), 5.38 (s, 2H), 7.13 (dd, J=5.27, 0.50 Hz, 1H), 7.27 (d, J=8.28 Hz, 1H), 7.61 (d, J=8.53 Hz, 1H), 8.36 (d, J=5.27 Hz, 1H), 8.77 (s, 1H).

Step 3: Synthesis of 5-chloro-2-(chloromethyl)-1-(4,4,4-trifluorobutyl)imidazo[4,5-b]pyridine hydrochloride (8c)

To a solution of alcohol (8b) (2.88 g, 9.807 mmole) in 50 mL of dichloromethane was added dropwise a solution of thionyl chloride (1.573 mL, 2.2 eq.) in 10 mL of dichloromethane. The reaction mixture was stirred for one hour at 45° C. It was then concentrated under vacuum to give the desired intermediate (8c) (3.42 g, 100% yield) as an HCl salt, which was used as such in the next step.

Intermediate 9b Synthesis of [5-chloro-1-(4-fluorobutyl)imidazo[4,5-b]pyridin-2-yl]methanol

Step 1: Synthesis of (5-chloro-1H-imidazo[4,5-b]pyridin-2-yl)methanol (intermediate 9a)

A mixture of 2-hydroxyacetic acid (69.221 g, 910 mmoles) and 6-chloropyridine-2,3-diamine (65.34 g, 455 mmoles) in xylene (950 mL) was stirred at 150° C. for 4 hours. The mixture was then cooled to about 60° C. and treated with 3N HCl (290 ml), then basified to pH=7-8 by the addition of aqueous ammonia. The resulting solid was filtered off and washed with $H_2O$ and methyl t-butyl-methyl ether to give 80.88 g (86% yield) of the desired intermediate (9a).

Step 2: Synthesis of [5-chloro-1-(4-fluorobutyl)imidazo[4,5-b]pyridin-2-yl]methanol (intermediate 9b)

A mixture of intermediate (9a) (72.8 g, 396.5 mmoles), 1-bromo-4-fluoro-butane (71.3 g, 459.97 mmoles, 1.16 eq.) and potassium carbonate (164.4 g, 1189.6 mmoles, 3 eq.) in acetonitrile (1.5 L) was stirred at 60° C. for 12 hours. The mixture was then filtered and the filtrate was poured into ice-water. The mixture was extracted with ethyl acetate (1000 ml×3). The combined organics were washed brine, dried over $Na_2SO_4$, filtered and evaporated under vacuum. The residue was purified by column chromatography over silica gel (eluent: $CH_2Cl_2/CH_3OH$ from 100/1 to 15/1) followed by a purification by preparative high-performance liquid chromatography (column C18, eluent: $CH_3CN$, $H_2O$ from 15/85 to 40/60, 0.05% TFA), to give the desired intermediate (9b) (11.6 g).

Intermediate 10b: Synthesis of 1'-[[5-chloro-1-(3-methylsulfonylpropyl)indol-2-yl]methyl]spiro[azetidine-3,3'-indoline]-2'-one hydrochloride

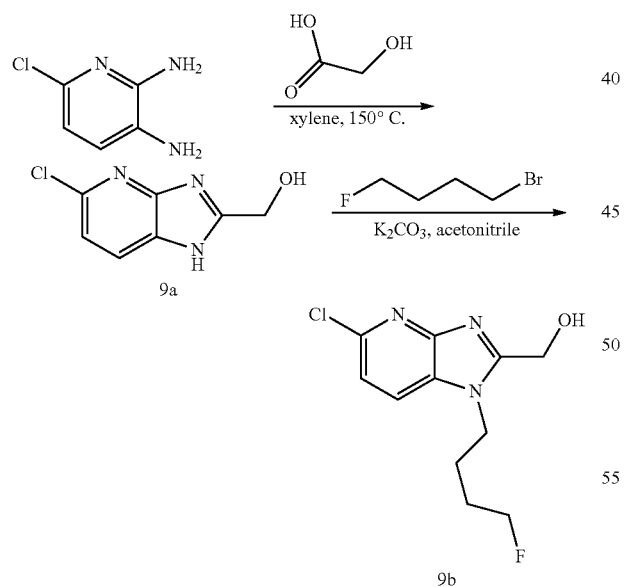

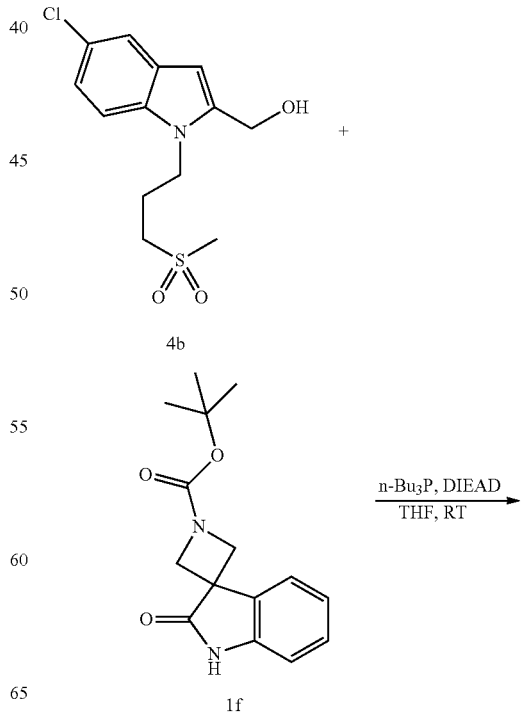

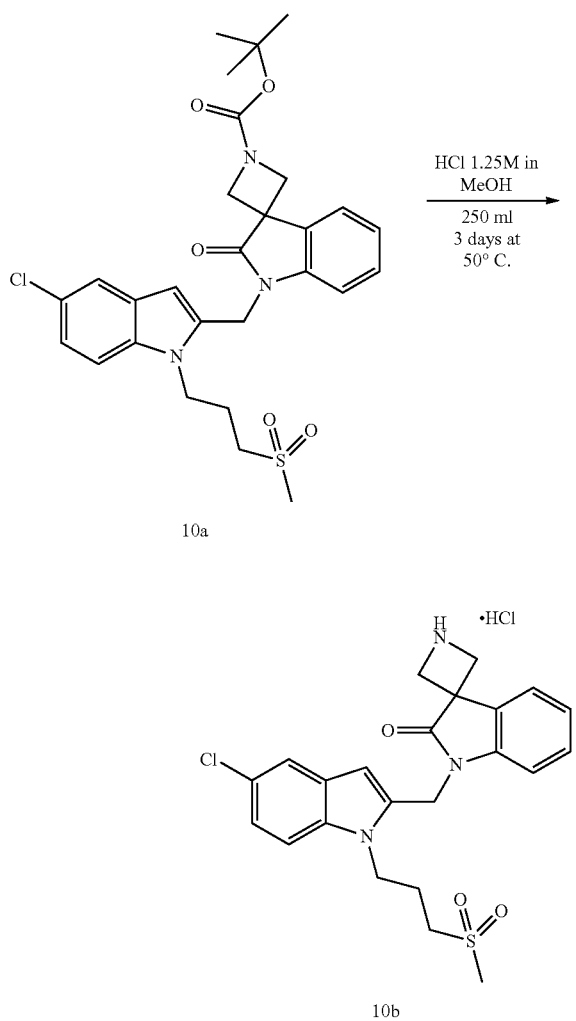

10a

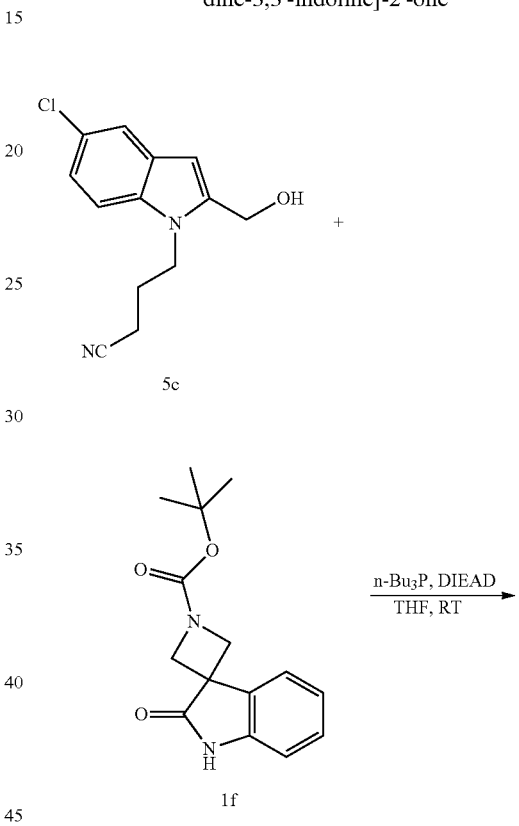

10b

Step 1: Synthesis of tert-butyl 1'-[[5-chloro-1-(3-methylsulfonylpropyl)indol-2-yl]methyl]-2'-oxo-spiro[azetidine-3,3'-indoline]-1-carboxylate (10a)

To a solution of intermediate (4b) (10 g, 33.13 mmol) and intermediate (10 (9.01, 33.13 mmol) in dry THF (200 ml) was added tri-n-butylphosphine (16.55 ml, 66.27 mmol) and DIEAD (12.9 ml, 66.27 mmol) at room temperature. The reaction mixture was stirred at room temperature for 30 min. The reaction mixture was then evaporated and the crude was dissolved in diethyl ether (500 ml) and stirred overnight at room temperature. The resulting solid was filtered off to yield (12 g, 61%) of the desired intermediate (10a) as a white powder. This was used as such in the next step.

m/z=558 (M+H)⁺.

Step 2: Synthesis of 1'-[[5-chloro-1-(3-methylsulfonylpropyl)indol-2-yl]methyl]spiro[azetidine-3,3'-indoline]-2'-one hydrochloride (10b)

Intermediate (10a) (12 g, 21.5 mmol) was dissolved in methanol HCl solution 1.25 M (250 ml). The reaction mixture was heated at 50° C. for three days. The reaction mixture was then allowed to cool down to room temperature and filtered off. The resulting white solid was washed with methanol and dried in the oven to give the desired intermediate (10b) (7.8 g). The organic layer was evaporated and the solid was triturated in methanol then filtered off to get a second crop of the desired intermediate (10b) (1.3 g). The two batches were mixed together (9.1 g, 88% yield in total) and used as such in the next step.

m/z=458 (M+H)⁺

Intermediate 11b: Synthesis of 1'-[[5-chloro-1-(3-methylsulfonylpropyl)indol-2-yl]methyl]spiro[azetidine-3,3'-indoline]-2'-one

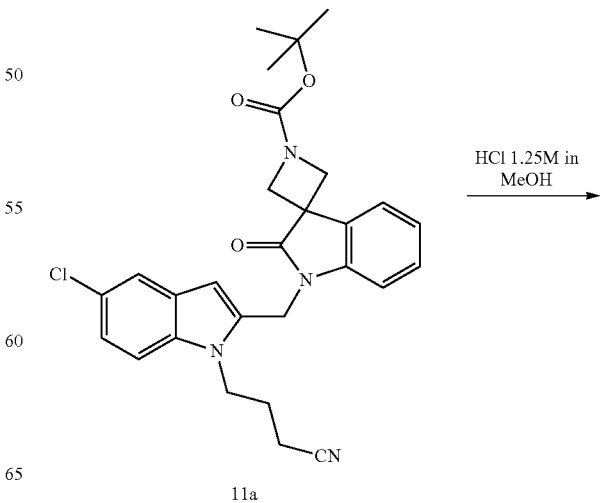

11a

-continued

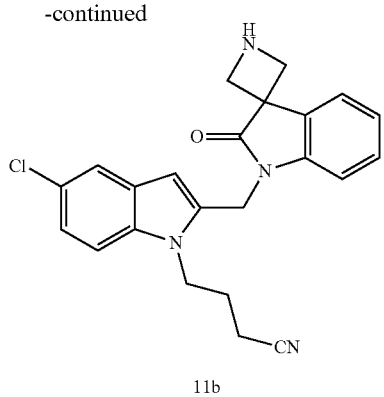

11b

Step 1: Synthesis of tert-butyl 1'-[[5-chloro-1-(3-cyanopropyl)indol-2-yl]methyl]-2'-oxo-spiro[azetidine-3,3'-indoline]-1-carboxylate 11a This intermediate was synthetized following the procedure reported for the synthesis of intermediate (10a), using intermediate (5c) instead of (4b).

Step 2: Synthesis of 1'-[[5-chloro-1-(3-methylsulfonylpropyl)indol-2-yl]methyl]spiro (11b)

A mixture of intermediate (11a) (9.205 g, 18.227 mmoles) in HCl 1.25M in MeOH (320 mL) was stirred at 40° C. for 3 hours. The reaction mixture was then diluted with water (800 mL) and extracted with DCM (2×). The organic layers were combined and basified with MeOH/NH$_3$ 7M until pH>9, filtered and concentrated in vacuo. The residue was triturated in DIPE and the resulting solid was filtered off and dried in the vacuum oven to give the desired intermediate (11b) (4.26 g, 52% yield).

$^1$H NMR (400 MHz, DMSO-d6) δ ppm 1.96 (dt, J=14.91, 7.40 Hz, 2H) 2.58 (t, J=7.37 Hz, 2H) 3.89-4.22 (m, 4H) 4.27-4.36 (m, 2H) 5.12 (s, 2H) 6.36 (s, 1H) 7.07 (d, J=7.70 Hz, 1H) 7.12-7.20 (m, 2H) 7.26-7.32 (m, 1H) 7.48-7.55 (m, 2H) 7.89 (dd, J=7.37, 0.77 Hz, 1H); m/z=404.99 (M+H)$^+$.

Intermediate 12b Synthesis of 1'-({5-chloro-1-[3-(methylsulfonyl)propyl]-1H-benzimidazol-2-yl}methyl)spiro[azetidine-3,3'-indol]-2'(1'H)-one

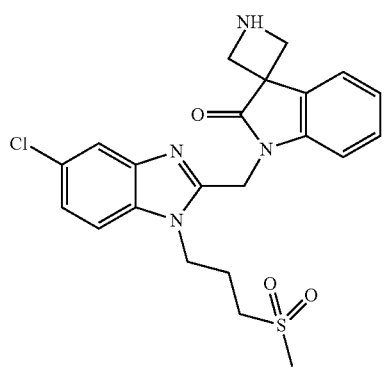 [SMILES: CS(=O)(=O)CCCn1c(CN2C(=O)C3(CNC3)c3ccccc32)nc2cc(Cl)ccc21]

Step 1: Synthesis of tert-butyl 1'-({5-chloro-1-[3-(methylsulfonyl)propyl]-1H-benzimidazol-2-yl}methyl)-2'-oxo-1',2'-dihydro-1H-spiro[azetidine-3,3'-indole]-1-carboxylate (12a)

Tert-butyl 2'-oxo-1',2'-dihydro-1H-spiro[azetidine-3,3'-indole]-1-carboxylate (1f) (1000 mg, 3.65 mmols) was dissolved in dry DMF (23 ml), then 5-chloro-2-(chloromethyl)-1-[3-(methylsulfonyl)propyl]-1H-benzimidazole hydrochloric acid (6e) (1304 mg, 3.64 mmols) and cesium carbonate (3563 mg, 3.56 mmols) were added. The reaction mixture was stirred at room temperature overnight. Iced water was added and the mixture was stirred overnight. The formed solid was filtered off and washed with water and a little ether. After drying in the vacuum oven the desired product (12a) was obtained as a pink solid (1695 mg, yield=81.5%).

$^1$H NMR (400 MHz, DMSO-d$_6$) δ ppm 1.44 (s, 9H) 2.10-2.21 (m, 2H) 3.00 (s, 3H) 3.19-3.25 (m, 2H) 4.03-4.19 (m, 4H) 4.47 (t, J=7.48 Hz, 2H) 5.22 (s, 2H) 7.13 (td, J=7.48, 0.88 Hz, 1H) 7.19 (d, J=7.70 Hz, 1H) 7.27-7.34 (m, 2H) 7.65-7.69 (m, 3H); m/z=559.21 (M+H)$^+$.

Step 2: Synthesis of 1'-({5-chloro-1-[3-(methylsulfonyl)propyl]-1H-benzimidazol-2-yl}methyl)spiro[azetidine-3,3'-indol]-2'(1'H)-one (12b)

To a solution of tert-butyl 1'-({5-chloro-1-[3-(methylsulfonyl)propyl]-1H-benzimidazol-2-yl}methyl)-2'-oxo-1',2'-dihydro-1H-spiro[azetidine-3,3'-indole]-1-carboxylate (12a) (1.5 g, 2.63 mmoles) in DCM (20 mL) was added TFA (1 mL, 5 eq.) at room temperature. After 12 hours, more TFA (2 mL) was added and the mixture was stirred for 24 hours. The reaction was then neutralized by an aqueous Na$_2$CO$_3$ solution. DCM was evaporated and the formed solid was filtered off and washed with water and ether to give the TFA salt of the desired product (12b) as a grey powder (1.303 g, yield=86.5%).

$^1$H NMR (400 MHz, DMSO-d$_6$) δ ppm 2.11-2.26 (m, 2H) 3.01 (s, 3H) 3.19-3.28 (m, 2H) 4.16-4.35 (m, 4H) 4.48 (t, J=7.48 Hz, 2H) 5.22 (s, 2H) 7.18-7.28 (m, 2H) 7.32 (dd, J=8.80, 1.98 Hz, 1H) 7.36 (td, J=7.90, 0.88 Hz, 1H) 7.66 (d, J=1.98 Hz, 1H) 7.69 (d, J=8.80 Hz, 1H) 7.85 (d, J=6.82 Hz, 1H) 9.27 (br. s., 2H); m/z=459.18 (M+H)$^+$.

Intermediate 13b: synthesis of 4-[5-chloro-2-[(2'-oxospiro[azetidine-3,3'-indoline]-1'-yl)methyl]benzimidazol-1-yl]butanenitrile

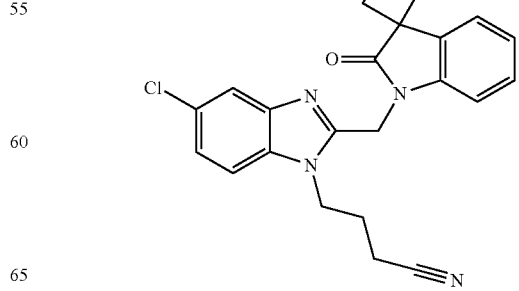

This intermediate was synthetized following the 2-step procedure reported for the synthesis of intermediate (12b), using intermediate (7d) instead of (6e) in the first step and was obtained as a white solid.

$^1$H NMR (400 MHz, DMSO-d$_6$) δ ppm 2.02 (quin, J=7.5 Hz, 2H), 2.60 (t, J=7.4 Hz, 2H), 3.62-4.02 (m, 4H), 4.38 (t, J=7.6 Hz, 2H), 5.22 (s, 2H), 7.08-7.16 (m, 2H), 7.20-7.27 (m, 1H), 7.29 (dd, J=8.7, 1.9 Hz, 1H), 7.47-7.54 (m, 1H), 7.64 (d, J=8.6 Hz, 1H), 7.67 (d, J=2.0 Hz, 1H); m/z=406 (M+H)$^+$ Intermediate 14b: synthesis of 1'-[[5-chloro-1-(4-fluorobutyl)imidazo[4,5-b]pyridin-2-yl]methyl]spiro[azetidine-3,3'-indoline]-2'-one

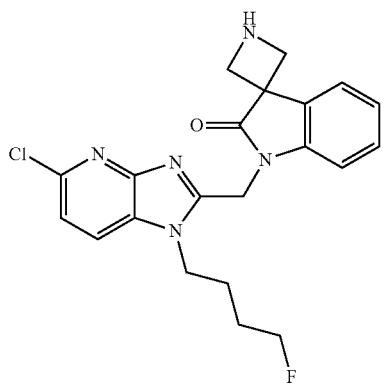 [SMILES: O=C1N(Cc2nc3nc(Cl)ccc3n2CCCCF)c2ccccc2C12CNC2]

This intermediate was synthetized following the 2-step procedure reported for the synthesis of intermediate (11b), using intermediate (9b) instead of (5c), and triphenylphosphine instead of n-tributylphosphine in the first step and was obtained as a white solid.

m/z=414 (M+H)$^+$

Intermediate 15b: synthesis of 1'-[[5-chloro-1-(4,4,4-trifluorobuty)pimidazo[4,5-b]pyridin-2-yl]methyl]spiro[azetidine-3,3'-indoline]-2'-one

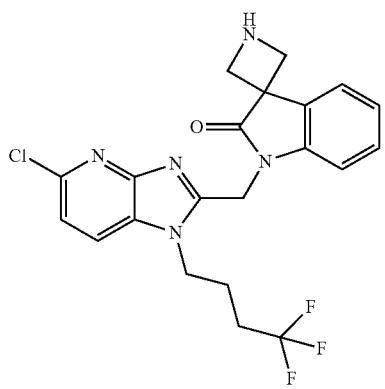 [SMILES: O=C1N(Cc2nc3nc(Cl)ccc3n2CCCC(F)(F)F)c2ccccc2C12CNC2]

This intermediate was synthetized following the 2-step procedure reported for the synthesis of intermediate (12b), using intermediate (8c) instead of (6e), and sodium hydride (60% in mineral oil) instead of cesium carbonate in the first step and was obtained as a slightly yellow solid; m/z=450 (M+H)$^+$.

Intermediate 16b Synthesis of 1'-({5-chloro-1-[3-(methylsulfonyl)propyl]-1H-indol-2-yl}methyl)spiro[piperidine-4,3'-pyrrolo[2,3-c]pyridin-2'(1'H)-one

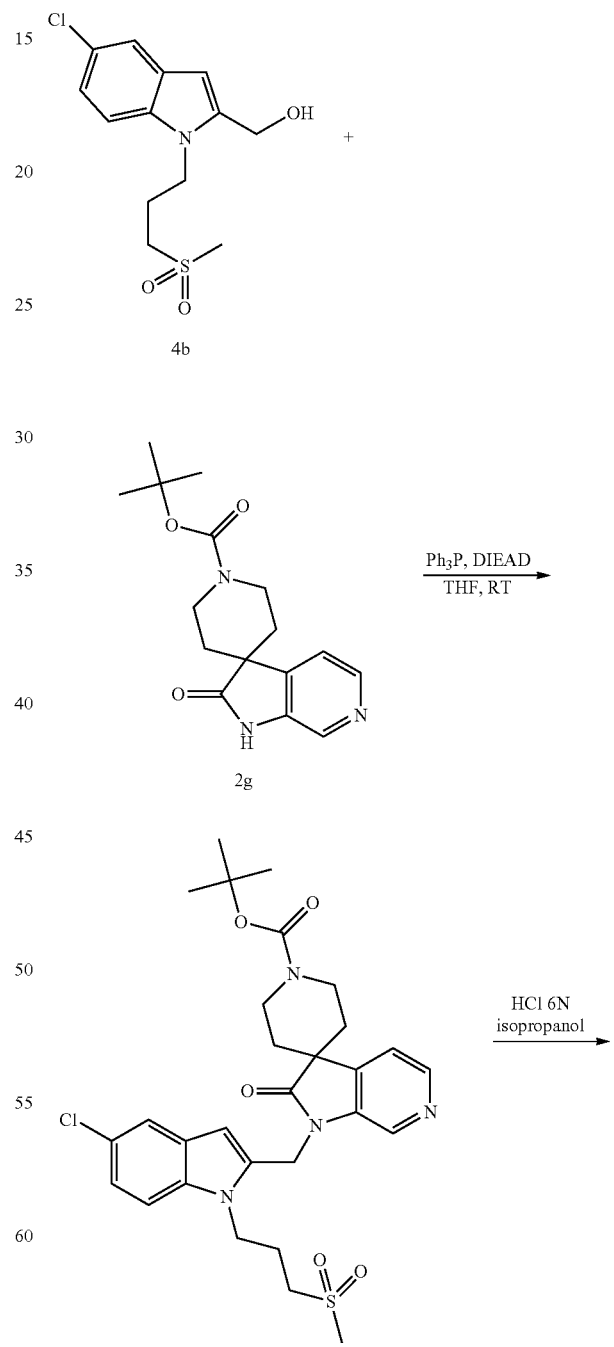

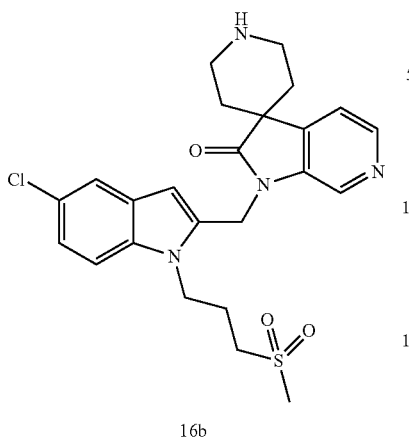

16b

Step 1: Synthesis of tert-butyl 1'-({5-chloro-1-[3-(methylsulfonyl)propyl]-1H-indol-2-yl}methyl)-2'-oxo-1',2'-dihydro-1H-spiro[piperidine-4,3'-pyrrolo[2,3-c]-pyridine]-1-carboxylate (16a)

To a suspension of {5-chloro-1-[3-(methylsulfonyl)propyl]-1H-indol-2-yl}methanol (4b) (4000 mg, 13.25 mmols), tert-butyl 2'-oxo-1',2'-dihydro-1H-spiro[piperidine-4,3'-pyrrolo[2,3-c]pyridine]-1-carboxylate (2g) (4423 mg, 14.58 mmols) and TPP (4172 mg, 15.91 mmols) in dry THF (92 ml) was added DIEAD (3.869 ml, 19.88 mmols) at room temperature and the reaction mixture was stirred overnight. THF was evaporated and the crude was purified by column chromatography. After evaporation of the relevant fractions, the residue was recrystallized in water. The formed crystals were filtered off and washed with some water and heptane to get the title product (16a) as a beige powder (1231 mg, yield=15.8%).

$^1$H NMR (400 MHz, DMSO-d$_6$) δ ppm 1.45 (s, 9H) 1.80 (t, J=5.50 Hz, 4H) 2.03-2.16 (m, 2H) 3.01 (s, 3H) 3.14-3.25 (m, 2H) 3.60-3.83 (m, 4H) 4.37 (t, J=7.48 Hz, 2H) 5.20 (s, 2H) 6.37 (s, 1H) 7.16 (dd, J=8.69, 2.09 Hz, 1H) 7.53 (d, J=1.98 Hz, 1H) 7.55 (d, J=8.80 Hz, 1H) 7.69 (d, J=4.62 Hz, 1H) 8.33 (d, J=4.84 Hz, 1H) 8.39 (s, 1H); m/z=587.23 (M+H)$^+$.

Step 2: Synthesis of 1'-({5-chloro-1-[3-(methylsulfonyl)propyl]-1H-indol-2-yl}-methyl)spiro[piperidine-4,3'-pyrrolo[2,3-c]pyridin]-2'(1'H)-one (16b)

To a solution of tert-butyl 1'-({5-chloro-1-[3-(methylsulfonyl)propyl]-1H-indol-2-yl}-methyl)2'-oxo-1',2'-dihydro-1H-spiro[piperidine-4,3'-pyrrolo[2,3-c]pyridine]-1-carboxylate (16a) (3.39 g, 3.75 mmols) in DCM (20 ml) was added TFA (2.872 ml, 37.53 mmols) and the mixture was stirred overnight at room temperature. Then water was added and the reaction mixture was basified with an aqueous Na$_2$CO$_3$ solution. DCM was evaporated and the remaining aqueous suspension was stirred for 3 hours. The solid was filtered off, washed with water and then purified by column chromatography to obtain a pink glassy oil. The product was triturated in diethyl ether to give the desired product (16b) as a pink powder which was dried in the vacuum oven (466 mg, 23.7%).

$^1$H NMR (400 MHz, DMSO-d$_6$) δ ppm 1.62-1.88 (m, 4H) 2.02-2.18 (m, 2H) 2.93-3.07 (m, 5H) 3.11-3.24 (m, 4H) 4.38 (t, J=7.48 Hz, 2H) 5.19 (s, 2H) 6.33 (s, 1H) 7.16 (dd, J=8.69, 2.09 Hz, 1H) 7.50-7.58 (m, 2H) 7.64 (d, J=4.84 Hz, 1H) 8.29-8.42 (m, 2H); m/z=487.27 (M+H)$^+$.

Intermediate 17b: synthesis of 4-[5-chloro-2-[(2'-oxospiro[piperidine-4,3'-pyrrolo[2,3-c]pyridine]-1'-yl)methyl]indol-1-yl]butanenitrile

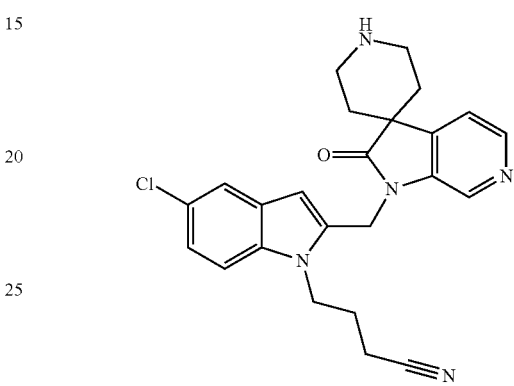

This intermediate was synthetized following the 2-step procedure reported for the synthesis of intermediate (11b), using intermediate (2g) instead of (10 in the first step and was obtained as a white solid.

$^1$H NMR (400 MHz, DMSO-d6) δ ppm 1.61-1.86 (m, 4H) 1.99 (quin, J=7.59 Hz, 2H) 2.58 (t, J=7.37 Hz, 2H) 2.91-3.21 (m, 4H) 4.23-4.36 (m, 2H) 5.19 (s, 2H) 6.33 (s, 1H) 7.12-7.17 (m, 1H) 7.50-7.56 (m, 2H) 7.64 (d, J=4.62 Hz, 1H) 8.34 (d, J=4.84 Hz, 1H) 8.38 (s, 1H); m/z=434.08 (M+H)$^+$.

Intermediate 18b: synthesis of 4-[5-chloro-2-[(2'-oxospiro[piperidine-4,3'-pyrrolo[2,3-c]pyridine]-1'-yl)methyl]benzimidazol-1-yl]butanenitrile bis hydrochloride

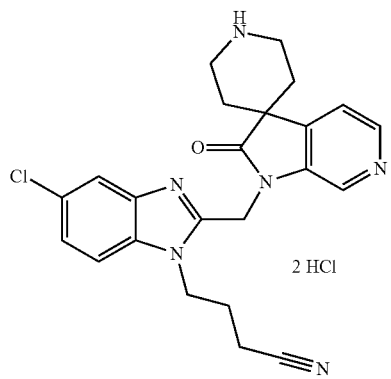 [SMILES: N#CCCCn1c(CN2C(=O)C3(CCNCC3)c3ccncc32)nc2cc(Cl)ccc21]

Step 1: Synthesis of tert-butyl 1'-[[5-chloro-1-(3-cyanopropyl)benzimidazol-2-yl]methyl]-2'-oxo-spiro[piperidine-4,3'-pyrrolo[2,3-c]pyridine]-1-carboxylate (18a)

This intermediate was synthetized following the procedure reported for the synthesis of intermediate (13a), using intermediate (2g) instead of (10 in the first step and was obtained as a white solid.

$^1$H NMR (400 MHz, DMSO-d6) δ ppm 1.45 (s, 9H), 1.66-1.85 (m, 4H), 1.98-2.15 (m, 2H), 2.55-2.68 (m, 2H), 3.57-3.82 (m, 4H) 4.25-4.51 (m, 2H) 5.22 (s, 2H) 7.29 (dd, J=8.58, 2.64 Hz, 1H) 7.62-7.69 (m, 3H) 8.31 (d, J=4.62 Hz, 1H) 8.46 (s, 1H); m/z=535 (M+H)$^+$

Step 2: synthesis of 4-[5-chloro-2-[(2'-oxospiro[piperidine-4,3'-pyrrolo[2,3-c]pyridine]-1'-yl)methyl]benzimidazol-1-yl]butanenitrile bis hydrochloride (18b)

Intermediate (18a) (6 g, 11.214 mmoles) was stirred in HCl 6M in isopropanol (100 mL) at 40° C. for 2 hours, then at room temperature overnight. The resulting white precipitate was filtered off, washed with ether and dried in the vacuum oven to give the desired intermediate (18b) (5.6 g, quant. yield) as a bis hydrochloride salt.

m/z=435 (M+H)$^+$.

Synthesis of Final Compounds

Synthesis of compound 1: 1'-[[5-chloro-1-(3-methylsulfonylpropyl)indol-2-yl]methyl]-N-isopropyl-2'-oxo-spiro[azetidine-3,3'-indoline]-1-carboxamide

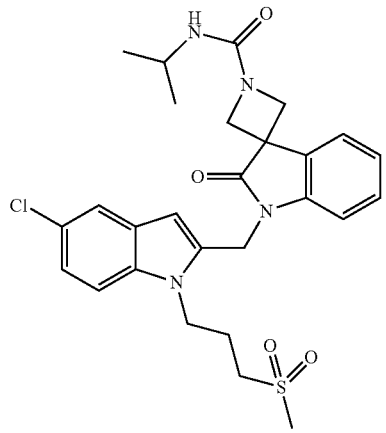 [SMILES: CC(C)NC(=O)N1CC2(C1)C(=O)N(Cc1cc3cc(Cl)ccc3n1CCCS(C)(=O)=O)c1ccccc12]

Intermediate (10b) (9.2 g, 18.6 mmol) was suspended in dioxane and Hunig's base (6.4 ml, 37.2 mmol) was added and the resulting mixture was stirred for 10 minutes. 2-Isocyanatopropane (2.2 ml, 22.3 mmol) was then added at room temperature. The mixture was stirred overnight at room temperature. To the solution was added an excess of MeOH (5 ml) and the mixture was stirred overnight. The solvent was evaporated. The residue was dissolved in dichloromethane (200 ml) and the resulting solution was washed with water three times (50 ml), dried over MgSO4, filtered and concentrated in vacuo. The residue was triturated in diisopropyl ether and stirred overnight in this solvent. The resulting white powder was filtered and dried in the oven at 50° C. to give the desired compound (1) (9.3 g, 92%) of a white powder.

$^1$H NMR (400 MHz, DMSO-d6) δ ppm 1.09 (d, J=6.6 Hz, 6H), 2.08 (t, J=7.4 Hz, 2H), 2.99 (s, 3H), 3.14-3.22 (m, 2H), 3.77 (dd, J=14.3, 6.6 Hz, 1H), 3.98 (d, J=7.9 Hz, 2H), 4.13 (d, J=8.1 Hz, 2H), 4.39 (t, J=7.4 Hz, 2H), 5.13 (s, 2H), 6.33-6.41 (m, 2H), 7.08 (d, J=7.9 Hz, 1H), 7.11-7.18 (m, 2H), 7.25-7.32 (m, 1H), 7.52 (d, J=2.0 Hz, 1H), 7.55 (d, J=8.8 Hz, 1H), 7.59-7.64 (m, 1H); m/z=543 (M+H)$^+$

Synthesis of compound 2: tert-butyl 4-[[1'-[[5-chloro-1-(3-cyanopropyl)indol-2-yl]methyl]-2'-oxo-spiro[azetidine-3,3'-indoline]-1-carbonyl]amino]piperidine-1-carboxylate

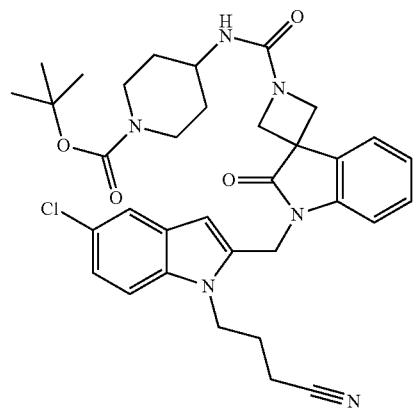 [SMILES: CC(C)(C)OC(=O)N1CCC(NC(=O)N2CC3(C2)C(=O)N(Cc2cc4cc(Cl)ccc4n2CCCC#N)c2ccccc23)CC1]

To a mixture of intermediate (11b) (1000 mg, 2.47 mmol) and pyridine (0.597 mL, 0.982 g/mL, 7.409 mmol) in DCM was added triphosgene (732.893 mg, 2.47 mmol) at room temperature. The mixture turned yellow immediately. After 1 hour, the reaction mixture was diluted with DCM (20 mL), and water (50 mL) and HCl 1N (10 mL) were added. The organic layer was separated, dried over MgSO$_4$, filtered and concentrated in vacuo. The resulting white foam (600 mg, 1.284 mmol) was then redissolved in DCM and tert-butyl 4-aminopiperidine-1-carboxylate (911.804 mg, 3.851 mmol, 3 eq.) and DIPEA (0.885 mL, 0.75 g/mL, 5.135 mmol) were added at room temperature. After 2 hours, the reaction mixture was diluted with DCM, washed with a 5% HCl solution, then brine, dried over MgSO$_4$, filtered and concentrated in vacuo. The crude product was purified by column chromatography (gradient of MeOH to 5% in DCM) to give 525 mg (62% yield) of the desired compound (2), as a white solid after trituration with DIPE.

$^1$H NMR (400 MHz, DMSO-d6) δ ppm 1.20-1.34 (m, 2H) 1.40 (s, 9H) 1.68-1.82 (m, 2H) 1.89-2.05 (m, 2H) 2.57 (t, J=7.37 Hz, 2H) 2.68-2.93 (m, 2H) 3.61-3.64 (m, 1H) 3.83-3.95 (m, 2H) 3.99 (d, J=7.92 Hz, 2H) 4.14 (d, J=8.14 Hz, 2H) 4.31 (t, J=7.30 Hz, 2H) 5.13 (s, 2H) 6.33 (s, 1H) 6.48 (d, J=7.92 Hz, 1H) 7.08 (d, J=7.92 Hz, 1H) 7.11-7.19 (m, 2H) 7.23-7.34 (m, 1H) 7.48-7.56 (m, 2H) 7.63 (d, J=6.60 Hz, 1H); m/z=631 [M+H]$^+$.

Synthesis of compound 3: 1'-[[5-chloro-1-(3-cyanopropyl)indol-2-yl]methyl]-2'-oxo-N-(4-piperidyl)spiro[azetidine-3,3'-indoline]-1-carboxamide

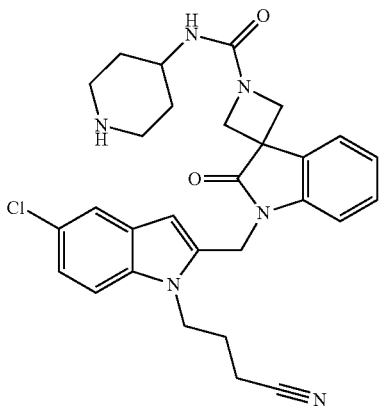 [SMILES: N#CCCCn1c(CN2C(=O)C3(CN(C(=O)NC4CCNCC4)C3)c3ccccc32)cc2cc(Cl)ccc21]

To a solution of compound (2) (430 mg, 0.681 mmol) in DCM was added TFA (0.521 mL, 1.49 g/mL, 6.813 mmol) at room temperature and the reaction mixture was stirred overnight. The reaction mixture was then concentrated under vacuum, redissolved in DCM, washed with an aqueous Na$_2$CO$_3$ solution, then brine, dried over MgSO$_4$, filtered and concentrated to give 260 mg (70% yield) of the desired compound (3) as a slightly orange foam.

$^1$H NMR (400 MHz, DMSO-d6) δ ppm 1.28-1.45 (m, 2H) 1.70-1.80 (m, 2H) 1.92-2.02 (m, 2H) 2.53-2.63 (m, 4H) 2.89-3.06 (m, 2H) 3.53-3.57 (m, 1H) 3.99 (d, J=8.14 Hz, 2H) 4.14 (d, J=7.92 Hz, 2H) 4.27-4.34 (m, 2H) 5.13 (s, 2H) 6.33 (s, 1H) 6.49 (d, J=7.92 Hz, 1H) 7.08 (d, J=7.92 Hz, 1H) 7.11-7.18 (m, 2H) 7.25-7.32 (m, 1H) 7.49-7.55 (m, 2H) 7.62 (d, J=7.48 Hz, 1H); m/z=531 [M+H]$^+$.

Synthesis of compound 4: 1'-[[5-chloro-1-(3-cyanopropyl)indol-2-yl]methyl]-2'-oxo-N-[1-(2,2,2-trifluoroethyl)-4-piperidyl]spiro[azetidine-3,3'-indoline]-1-carboxamide

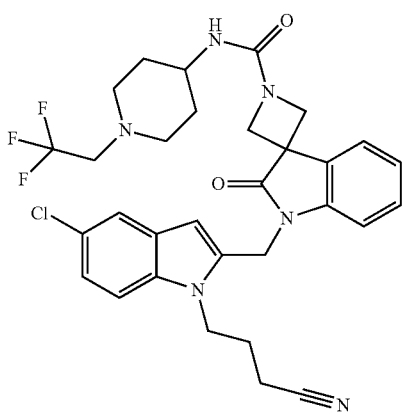 [SMILES: N#CCCCn1c(CN2C(=O)C3(CN(C(=O)NC4CCN(CC(F)(F)F)CC4)C3)c3ccccc32)cc2cc(Cl)ccc21]

To a solution of compound 3 (190 mg, 0.358 mmol) in dioxane were added DIPEA (0.185 mL, 0.75 g/mL, 1.073 mmol) and 2,2,2-trifluoroethyl 1,1,2,2,3,3,4,4,4-nonafluorobutane-1-sulfonate (136.716 mg, 0.358 mmol) at room temperature. After night, the reaction mixture was concentrated in vacuo, redissolved in DCM, washed with an aqueous Na$_2$CO$_3$ solution, then brine, dried over MgSO$_4$, filtered and concentrated. Purification by column chromatography (gradient of MeOH 5% in DCM) and recrystallization from DCM/DIPE gave the desired product (4) as a slightly pink solid (75 mg, 32% yield).

$^1$H NMR (400 MHz, DMSO-d6) δ ppm 1.36-1.54 (m, 2H) 1.67-1.80 (m, 2H) 1.90-2.03 (m, 2H) 2.31-2.44 (m, 2H) 2.54-2.62 (m, 2H) 2.83-2.96 (m, 2H) 3.14 (q, J=10.34 Hz, 2H) 3.29-3.31 (m, 1H) 3.99 (d, J=7.92 Hz, 2H) 4.14 (d, J=7.92 Hz, 2H) 4.26-4.35 (m, 2H) 5.13 (s, 2H) 6.33 (s, 1H) 6.44 (d, J=7.70 Hz, 1H) 7.08 (d, J=7.92 Hz, 1H) 7.11-7.19 (m, 2H) 7.24-7.33 (m, 1H) 7.49-7.56 (m, 2H) 7.62 (d, J=7.26 Hz, 1H); m/z=613 [M+H]$^+$.

Compounds (5) to (9) were synthetized following the reaction reported for the synthesis of compound (2), by using the appropriate amine instead of tert-butyl 4-aminopiperidine-1-carboxylate.

Compound 5: 1'-[[5-chloro-1-(3-cyanopropyl)indol-2-yl]methyl]-N-(1-methyl-4-piperidyl)-2'-oxo-spiro[azetidine-3,3'-indoline]-1-carboxamide

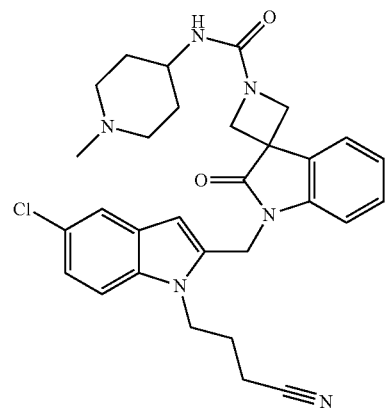 [SMILES: CN1CCC(NC(=O)N2CC3(C2)C(=O)N(Cc2cc4cc(Cl)ccc4n2CCCC#N)c2ccccc23)CC1]

$^1$H NMR (400 MHz, DMSO-d6) δ ppm 1.43-1.60 (m, 2H) 1.70-1.83 (m, 2H) 1.90-2.03 (m, 2H) 2.08-2.22 (m, 2H) 2.27 (s, 3H) 2.56 (t, J=7.37 Hz, 2H) 2.80-2.94 (m, 2H) 3.50-3.56 (m, 1H) 3.99 (d, J=7.92 Hz, 2H) 4.14 (d, J=7.92 Hz, 2H) 4.30 (t, J=7.48 Hz, 2H) 5.13 (s, 2H) 6.33 (s, 1H) 6.49 (d, J=7.70 Hz, 1H) 7.08 (d, J=7.92 Hz, 1H) 7.11-7.18 (m, 2H) 7.28 (td, J=7.70, 1.10 Hz, 1H) 7.49-7.54 (m, 2H) 7.62 (d, J=7.48 Hz, 1H); m/z=545 [M+H]$^+$.

Compound 6: 1'-[[5-chloro-1-(3-cyanopropyl)indol-2-yl]methyl]-2'-oxo-N-tetrahydropyran-4-yl-spiro[azetidine-3,3'-indoline]-1-carboxamide

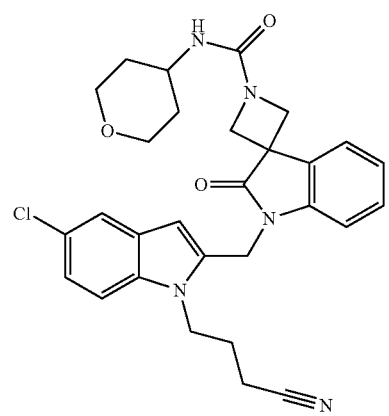 [SMILES: N#CCCCn1c(CN2C(=O)C3(CN(C(=O)NC4CCOCC4)C3)c3ccccc32)cc2cc(Cl)ccc21]

¹H NMR (400 MHz, DMSO-d6) δ ppm 1.38-1.55 (m, 2H) 1.68-1.80 (m, 2H) 1.90-2.07 (m, 2H) 2.58 (t, J=7.37 Hz, 2H) 3.28-3.35 (m, 2H) 3.62-3.72 (m, 1H) 3.80-3.91 (m, 2H) 4.01 (d, J=7.92 Hz, 2H) 4.16 (d, J=7.92 Hz, 2H) 4.26-4.38 (m, 2H) 5.14 (s, 2H) 6.35 (s, 1H) 6.52 (d, J=7.70 Hz, 1H) 7.09 (d, J=7.92 Hz, 1H) 7.12-7.19 (m, 2H) 7.24-7.35 (m, 1H) 7.50-7.57 (m, 2H) 7.64 (d, J=6.82 Hz, 1H); m/z=532 [M+H]⁺.

Compound 7: 1'-[[5-chloro-1-(3-cyanopropyl)indol-2-yl]methyl]-N-(3-hydroxycyclobutyl)-2'-oxo-spiro[azetidine-3,3'-indoline]-1-carboxamide

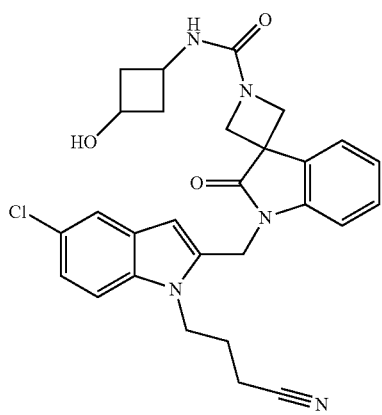 [SMILES: N#CCCCn1c(CN2C(=O)C3(CN(C(=O)NC4CC(O)C4)C3)c3ccccc32)cc2cc(Cl)ccc21]

m/z=518 [M+H]⁺.

Compound 8: 1'-[[5-chloro-1-(3-cyanopropyl)indol-2-yl]methyl]-N-(cis-3-hydroxycyclobutyl)-2'-oxo-spiro[azetidine-3,3'-indoline]-1-carboxamide

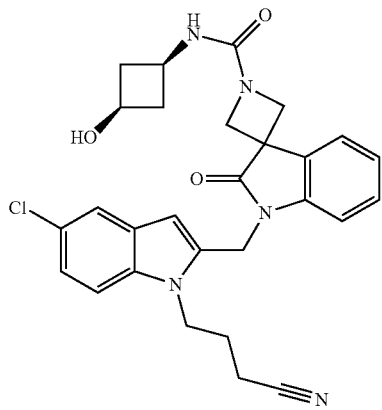 [SMILES: N#CCCCn1c(CN2C(=O)C3(CN(C(=O)N[C@H]4C[C@@H](O)C4)C3)c3ccccc32)cc2cc(Cl)ccc21]

¹H NMR (400 MHz, DMSO-d6) δ ppm 1.72-1.86 (m, 2H) 1.90-2.06 (m, 2H) 2.41-2.50 (m, 2H) 2.57 (t, J=7.15 Hz, 2H) 3.55-3.70 (m, 1H) 3.72-3.86 (m, 1H) 4.00 (d, J=7.92 Hz, 2H) 4.14 (d, J=7.92 Hz, 2H) 4.31 (t, J=7.26 Hz, 2H) 5.04 (d, J=5.50 Hz, 1H) 5.14 (s, 2H) 6.34 (s, 1H) 6.76 (d, J=7.70 Hz, 1H) 7.08 (d, J=7.92 Hz, 1H) 7.15 (m, J=7.30 Hz, 2H) 7.23-7.36 (m, 1H) 7.47-7.57 (m, 2H) 7.63 (d, J=7.26 Hz, 1H); m/z=518 [M+H]⁺.

Compound 9: 1'-[[5-chloro-1-(3-cyanopropyl)indol-2-yl]methyl]-N-(trans-3-hydroxycyclobutyl)-2'-oxo-spiro[azetidine-3,3'-indoline]-1-carboxamide

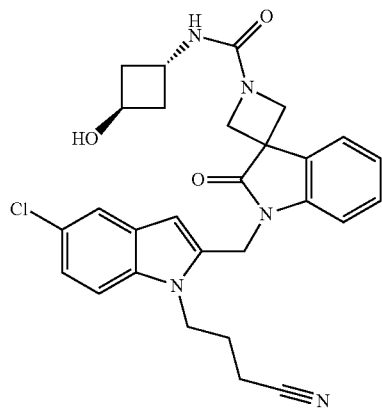 [SMILES: N#CCCCn1c(CN2C(=O)C3(CN(C(=O)N[C@H]4C[C@H](O)C4)C3)c3ccccc32)cc2cc(Cl)ccc21]

¹H NMR (400 MHz, DMSO-d6) δ ppm 1.89-2.03 (m, 2H) 2.03-2.22 (m, 4H) 2.53-2.63 (m, 2H) 4.00 (d, J=7.92 Hz, 2H) 4.14 (d, J=7.70 Hz, 2H) 4.17-4.36 (m, 4H) 4.87 (br. s, 1H) 5.13 (s, 2H) 6.34 (s, 1H) 6.78 (d, J=7.04 Hz, 1H) 7.08 (d, J=7.92 Hz, 1H) 7.11-7.20 (m, 2H) 7.23-7.34 (m, 1H) 7.47-7.57 (m, 2H) 7.63 (d, J=7.26 Hz, 1H); m/z=518 [M+H]⁺.

Compounds (10) to (17) were synthetized following the reaction reported for the synthesis of compound 2, by using the intermediate (10b) instead of (11b) with the appropriate amine instead of tert-butyl 4-aminopiperidine-1-carboxylate.

Compound 10: 1'-[[5-chloro-1-(3-methylsulfonylpropyl)indol-2-yl]methyl]-N-(cis-3-hydroxycyclobutyl)-2'-oxo-spiro[azetidine-3,3'-indoline]-1-carboxamide

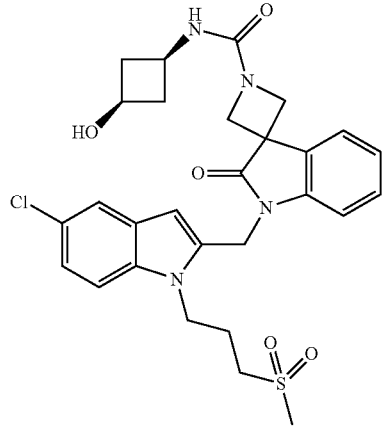 [SMILES: CS(=O)(=O)CCCn1c(CN2C(=O)C3(CN(C(=O)N[C@H]4C[C@@H](O)C4)C3)c3ccccc32)cc2cc(Cl)ccc21]

m/z=571 [M+H]⁺.

¹H NMR (400 MHz, DMSO-d6) δ ppm 1.70-1.87 (m, 2H) 2.01-2.16 (m, 2H) 2.40-2.50 (m, 2H) 3.00 (s, 3H) 3.15-3.25 (m, 2H) 3.56-3.69 (m, 1H) 3.72-3.86 (m, 1H) 4.00 (d, J=7.92 Hz, 2H) 4.14 (d, J=7.92 Hz, 2H) 4.33-4.47 (m, 2H) 5.04 (d, J=5.28 Hz, 1H) 5.14 (s, 2H) 6.37 (s, 1H) 6.76 (d, J=7.70 Hz, 1H) 7.14 (s, 3H) 7.24-7.35 (m, 1H) 7.53 (s, 2H) 7.63 (d, J=7.26 Hz, 1H)

Compound 11: 1'-[[5-chloro-1-(3-methylsulfonyl-propyl)indol-2-yl]methyl]-N-(trans-3-hydroxycyclobutyl)-2'-oxo-spiro[azetidine-3,3'-indoline]-1-carboxamide

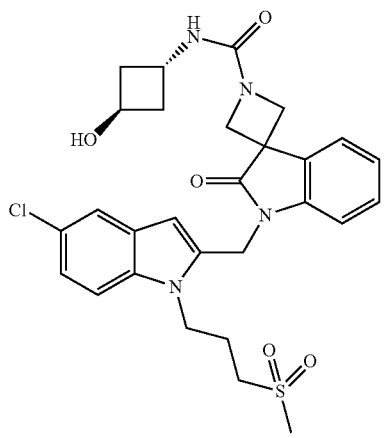 [SMILES: CS(=O)(=O)CCCn1c(CN2C(=O)C3(CN(C(=O)N[C@H]4C[C@H](O)C4)C3)c3ccccc32)cc2cc(Cl)ccc21]

m/z=571 [M+H]⁺

¹H NMR (400 MHz, DMSO-d6) δ ppm 1.96-2.26 (m, 6H) 3.00 (s, 3H) 3.11-3.24 (m, 2H) 4.00 (d, J=7.92 Hz, 2H) 4.08-4.32 (m, 4H) 4.34-4.48 (m, 2H) 4.96 (d, J=4.84 Hz, 1H) 5.14 (br. s., 2H) 6.37 (s, 1H) 6.78 (d, J=7.04 Hz, 1H) 7.14 (br. s., 3H) 7.23-7.37 (m, 1H) 7.47-7.59 (m, 2H) 7.63 (d, J=7.04 Hz, 1H)

Compound 12: 1'-[[5-chloro-1-(3-methylsulfonyl-propyl)indol-2-yl]methyl]-2'-oxo-N-(2,2,2-trifluoro-ethyl)spiro[azetidine-3,3'-indoline]-1-carboxamide

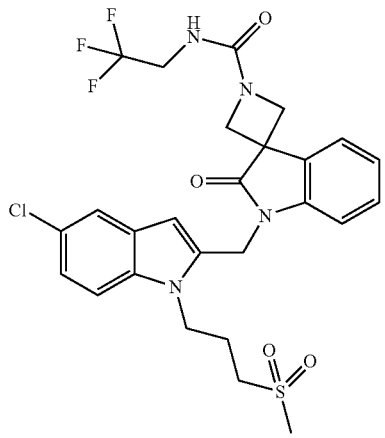 [SMILES: CS(=O)(=O)CCCn1c(CN2C(=O)C3(CN(C(=O)NCC(F)(F)F)C3)c3ccccc32)cc2cc(Cl)ccc21]

¹H NMR (400 MHz, chloroform-d) δ ppm 2.18 (quin, J=7.65 Hz, 2H) 2.91 (s, 3H) 3.09 (t, J=7.59 Hz, 2H) 3.81-4.02 (m, 2H) 4.17 (d, J=7.70 Hz, 2H) 4.36-4.42 (m, 2H) 4.44 (d, J=7.70 Hz, 2H) 4.90 (t, J=6.49 Hz, 1H) 5.06 (s, 2H) 6.52 (s, 1H) 7.09 (d, J=7.92 Hz, 1H) 7.13-7.19 (m, 2H) 7.20-7.25 (m, 1H) 7.27-7.37 (m, 1H) 7.52 (d, J=1.76 Hz, 1H) 7.55 (d, J=7.26 Hz, 1H); m/z=583 [M+H]⁺

Compound 13: 1'-[[5-chloro-1-(3-methylsulfonyl-propyl)indol-2-yl]methyl]-N-(2-hydroxy-1,1-dimethyl-ethyl)-2'-oxo-spiro[azetidine-3,3'-indoline]-1-carboxamide

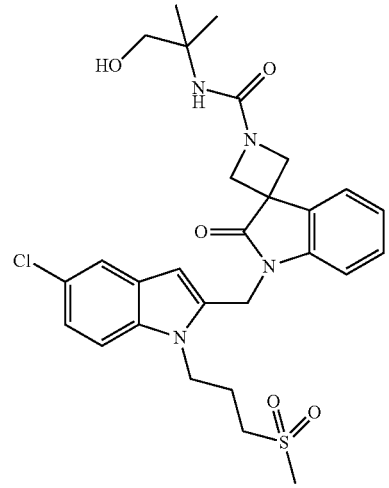 [SMILES: CC(C)(CO)NC(=O)N1CC2(C1)C(=O)N(Cc1cc3cc(Cl)ccc3n1CCCS(C)(=O)=O)c1ccccc12]

¹H NMR (400 MHz, chloroform-d) δ ppm 1.33 (s, 6H) 2.20 (qt, J=7.60 Hz, 2H) 2.94 (s, 3H) 3.10 (t, J=7.59 Hz, 2H) 3.63 (d, J=4.84 Hz, 2H) 4.10 (d, J=7.48 Hz, 2H) 4.34-4.45 (m, 5H) 4.81 (t, J=5.39 Hz, 1H) 5.07 (s, 2H) 6.53 (s, 1H) 7.09 (d, J=7.92 Hz, 1H) 7.14-7.20 (m, 2H) 7.24 (d, J=8.60 Hz, 1H) 7.30 (td, J=7.80, 1.20 Hz, 1H) 7.53 (d, J=1.76 Hz, 1H) 7.57 (dd, J=7.37, 0.77 Hz, 1H); m/z=573 (M+H)⁺

Compound 14: 1'-[[5-chloro-1-(3-methylsulfonyl-propyl)indol-2-yl]methyl]-N-(2-hydroxy-1-methyl-ethyl)-2'-oxo-spiro[azetidine-3,3'-indoline]-1-carboxamide

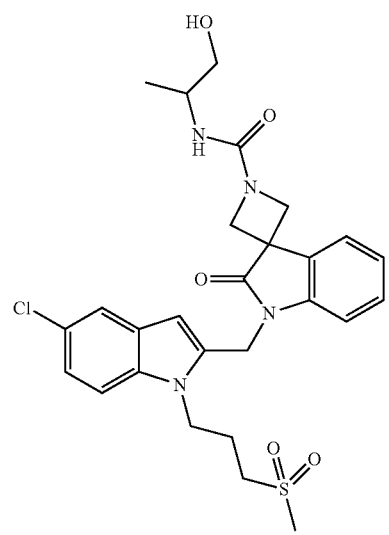 [SMILES: CC(CO)NC(=O)N1CC2(C1)C(=O)N(Cc1cc3cc(Cl)ccc3n1CCCS(C)(=O)=O)c1ccccc12]

¹H NMR (400 MHz, chloroform-d) δ ppm 1.20 (d, J=6.82 Hz, 3H) 2.19 (dt, J=14.63, 7.21 Hz, 2H) 2.94 (s, 3H) 3.03-3.21 (m, 3H) 3.48-3.58 (m, 1H) 3.68-3.79 (m, 1H) 4.00 (dd, J=6.82, 3.30 Hz, 1H) 4.12 (dd, J=9.68, 7.70 Hz, 2H)

4.34-4.45 (m, 4H) 4.48 (d, J=7.04 Hz, 1H) 4.99-5.15 (m, 2H) 6.53 (s, 1H) 7.10 (d, J=7.92 Hz, 1H) 7.13-7.20 (m, 2H) 7.21-7.25 (m, 1H) 7.28-7.36 (m, 1H) 7.53 (d, J=1.76 Hz, 1H) 7.57 (d, J=7.48 Hz, 1H); m/z=559 (M+H)⁺

Compound 15: 1'-[[5-chloro-1-(3-methylsulfonyl-propyl)indol-2-yl]methyl]-N-[2-(dimethylamino)ethyl]-N-methyl-2'-oxo-spiro[azetidine-3,3'-indoline]-1-carboxamide

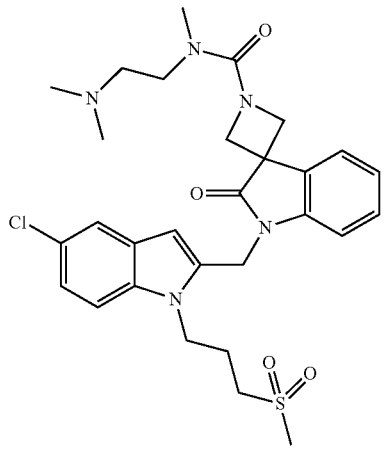 [SMILES: CN(C)CCN(C)C(=O)N1CC2(C1)C(=O)N(Cc1cc3cc(Cl)ccc3n1CCCS(C)(=O)=O)c1ccccc12]

¹H NMR (400 MHz, chloroform-d) δ ppm 2.15-2.26 (m, 2H) 2.40 (s, 6H) 2.63 (t, J=6.93 Hz, 2H) 2.93 (s, 3H) 2.95 (s, 3H) 3.05-3.13 (m, 2H) 3.49 (t, J=7.04 Hz, 2H) 4.19 (d, J=7.92 Hz, 2H) 4.37-4.42 (m, 2H) 4.45 (d, J=7.92 Hz, 2H) 5.06 (s, 2H) 6.50 (s, 1H) 7.05 (d, J=7.70 Hz, 1H) 7.12-7.19 (m, 2H) 7.22-7.31 (m, 2H) 7.51 (d, J=1.98 Hz, 1H) 7.61 (dd, J=7.26, 0.66 Hz, 1H); m/z=586 [M+H]⁺

Compound 16: 1'-[[5-chloro-1-(3-methylsulfonyl-propyl)indol-2-yl]methyl]-N-(2-morpholinoethyl)-2'-oxo-spiro[azetidine-3,3'-indoline]-1-carboxamide

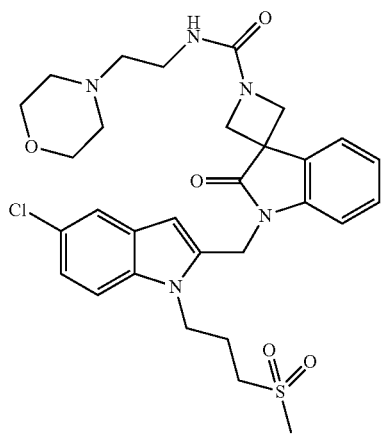 [SMILES: CS(=O)(=O)CCCn1c(CN2C(=O)C3(CN(C(=O)NCCN4CCOCC4)C3)c3ccccc32)cc2cc(Cl)ccc21]

m/z=614 [M+H]⁺
¹H NMR (400 MHz, chloroform-d) δ ppm 2.22 (qt, J=7.50 Hz, 2H) 2.45-2.52 (m, 4H) 2.54 (t, J=5.94 Hz, 2H) 2.92 (s, 3H) 3.07 (t, J=7.37 Hz, 2H) 3.38 (q, J=5.58 Hz, 2H) 3.71 (t, J=4.40 Hz, 4H) 4.13 (d, J=7.48 Hz, 2H) 4.37-4.46 (m, 4H) 4.97 (br. s, 1 H) 5.07 (s, 2H) 6.51 (s, 1H) 7.07 (d, J=7.92 Hz, 1H) 7.13-7.20 (m, 2H) 7.22-7.25 (m, 1H) 7.28-7.33 (m, 1H) 7.52 (d, J=1.76 Hz, 1H) 7.57 (d, J=8.14 Hz, 1H)

Compound 17: 1'-[[5-chloro-1-(3-methylsulfonyl-propyl)indol-2-yl]methyl]-N-[2-(dimethylamino)ethyl]-2'-oxo-spiro[azetidine-3,3'-indoline]-1-carboxamide

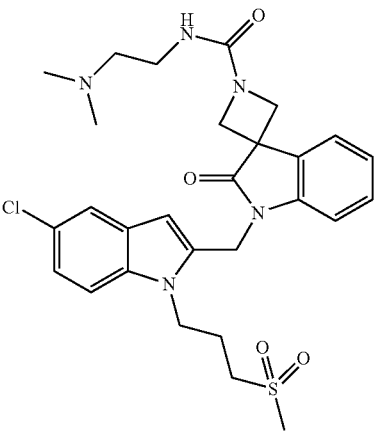 [SMILES: CN(C)CCNC(=O)N1CC2(C1)C(=O)N(Cc1cc3cc(Cl)ccc3n1CCCS(C)(=O)=O)c1ccccc12]

m/z=572 [M+H]⁺
¹H NMR (400 MHz, chloroform-d) δ ppm 2.16-2.26 (m, 2H) 2.36 (s, 6H) 2.57-2.70 (m, 2H) 2.94 (s, 3H) 3.09 (t, J=7.37 Hz, 2H) 3.37-3.49 (m, 2H) 4.15 (d, J=7.48 Hz, 2H) 4.38 (m, 2H) 4.42 (d, J=7.48 Hz, 2H) 5.07 (s, 2H) 5.37 (m, 1H) 6.51 (s, 1H) 7.06 (d, J=7.70 Hz, 1H) 7.10-7.22 (m, 2H) 7.22-7.34 (m, 2H) 7.52 (d, J=1.98 Hz, 1H) 7.54-7.62 (m, 1H)

Compound 18: 1'-[[5-chloro-1-(3-methylsulfonyl-propyl)benzimidazol-2-yl]methyl]-N-isopropyl-2'-oxo-spiro[azetidine-3,3'-indoline]-1-carboxamide

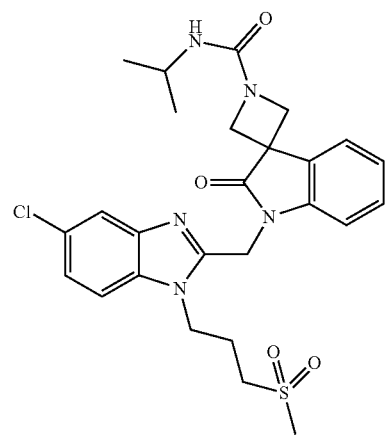 [SMILES: CC(C)NC(=O)N1CC2(C1)C(=O)N(Cc1nc3cc(Cl)ccc3n1CCCS(C)(=O)=O)c1ccccc12]

¹H NMR (400 MHz, DMSO-d6) δ ppm 1.09 (d, J=6.60 Hz, 6H) 2.17 (quin, J=7.48 Hz, 2H) 3.00 (s, 3H) 3.19-3.26 (m, 2H) 3.76 (sxt, J=6.40 Hz, 1H) 3.91-4.15 (m, 4H) 4.47 (t, J=7.37 Hz, 2H) 5.23 (s, 2H) 6.34 (d, J=7.92 Hz, 1H) 7.09-7.20 (m, 2H) 7.25-7.36 (m, 2H) 7.61 (d, J=7.04 Hz, 1H) 7.64-7.72 (m, 2H); m/z=544.20 (M+H)⁺.

Compound 19: 1'-[[5-chloro-1-(3-cyanopropyl)benzimidazol-2-yl]methyl]-N-isopropyl-2'-oxo-spiro[azetidine-3,3'-indoline]-1-carboxamide

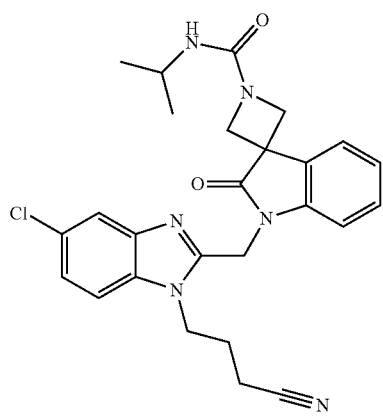 [SMILES: CC(C)NC(=O)N1CC2(C1)C(=O)N(Cc1nc3cc(Cl)ccc3n1CCCC#N)c1ccccc12]

$^1$H NMR (400 MHz, DMSO-d6) δ ppm 1.09 (d, J=6.60 Hz, 6H) 2.08 (quin, J=7.48 Hz, 2H) 2.62 (t, J=7.37 Hz, 2H) 3.76 (dq, J=13.81, 6.62 Hz, 1H) 3.90-4.16 (m, 4H) 4.39 (t, J=7.37 Hz, 2H) 5.22 (s, 2H) 6.36 (d, J=7.92 Hz, 1H) 7.08-7.21 (m, 2H) 7.24-7.37 (m, 2H) 7.56-7.73 (m, 3H); m/z=491.13 (M+H)$^+$; MP=210.38° C.

Compound 20: 1'-[[5-chloro-1-(4-fluorobutyl)imidazo[4,5-b]pyridin-2-yl]methyl]-N-isopropyl-2'-oxo-spiro[azetidine-3,3'-indoline]-1-carboxamide

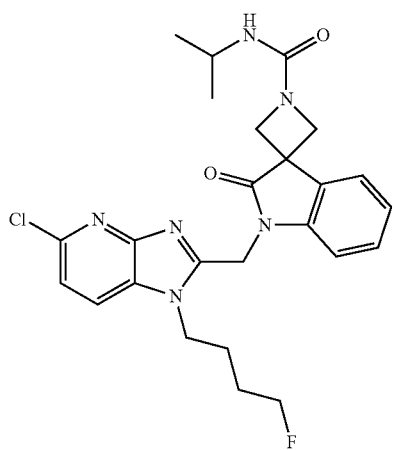 [SMILES: CC(C)NC(=O)N1CC2(C1)C(=O)N(Cc1nc3nc(Cl)ccc3n1CCCCF)c1ccccc12]

$^1$H NMR (400 MHz, chloroform-d) δ ppm 1.20 (d, J=6.20 Hz, 6H) 1.74-1.80 (m, 1H) 1.82-1.92 (m, 3H) 3.95-4.04 (m, 2H) 4.06 (d, J=7.26 Hz, 2H) 4.34 (d, J=7.26 Hz, 2H) 4.40 (t, J=7.30 Hz, 2H) 4.44 (t, J=5.39 Hz, 1H) 4.56 (t, J=5.17 Hz, 1H) 5.24 (s, 2H) 7.12-7.18 (m, 1H) 7.24 (d, J=8.36 Hz, 1H) 7.31 (td, J=7.81, 1.32 Hz, 1H) 7.53 (d, J=7.92 Hz, 1H) 7.59 (d, J=7.70 Hz, 1H) 7.64 (d, J=8.58 Hz, 1H); m/z=499.5 [M+H]$^+$ Compound 21: 1'-[[5-chloro-1-(4-fluorobutyl)imidazo[4,5-b]pyridin-2-yl]methyl]-N-(3-hydroxycyclobutyl)-2'-oxo-spiro[azetidine-3,3'-indoline]-1-carboxamide

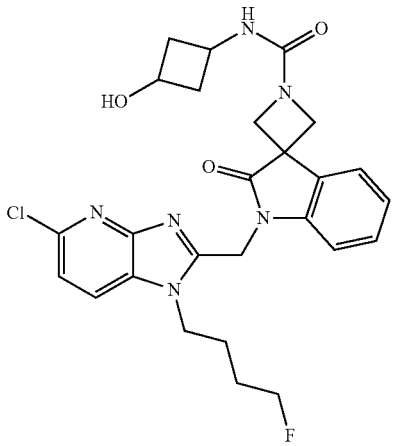 [SMILES: O=C(NC1CC(O)C1)N1CC2(C1)C(=O)N(Cc1nc3nc(Cl)ccc3n1CCCCF)c1ccccc12]

$^1$H NMR (400 MHz, chloroform-d) δ (some protons show cis-trans isomerism) ppm 1.69-1.94 (m, 5H) 2.19-2.30 (m, 1H) 2.30-2.41 (m, 1H) 2.71-2.84+3.12 (m, 2H) 3.79-3.92+3.96-4.05 (m, 1H) 4.08 (d, J=7.48 Hz, 2H) 4.32-4.50 (m, 6H) 4.54 (t, J=5.28 Hz, 1H) 4.86+4.95 (d, J=6.60 Hz and J=7.92 Hz, 1H) 5.22 (s, 2H) 7.09-7.16 (m, 1H) 7.22 (d, J=8.58 Hz, 1H) 7.25-7.31 (m, 1H) 7.44-7.55 (m, 2H) 7.66 (d, J=8.36 Hz, 1H); m/z=527.2 [M+H]$^+$ Compound 22: 1'-[[5-chloro-1-(4,4,4-trifluorobutyl)imidazo[4,5-b]pyridin-2-yl]methyl]-N-isopropyl-2'-oxo-spiro[azetidine-3,3'-indoline]-1-carboxamide

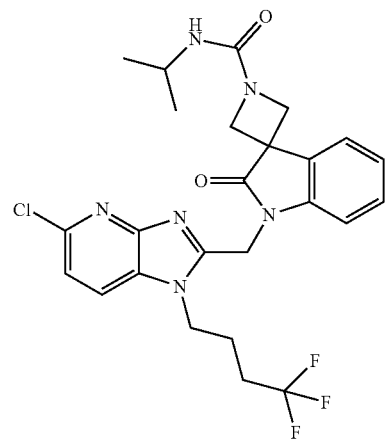 [SMILES: CC(C)NC(=O)N1CC2(C1)C(=O)N(Cc1nc3nc(Cl)ccc3n1CCCC(F)(F)F)c1ccccc12]

$^1$H NMR (400 MHz, DMSO-d6) δ ppm 1.09 (d, J=6.60 Hz, 5H) 1.89-2.06 (m, 2H) 2.29-2.47 (m, 2H) 3.67-3.84 (m, 1H) 3.97 (d, J=7.92 Hz, 2H) 4.11 (d, J=7.92 Hz, 2H) 4.46 (t, J=7.48 Hz, 2H) 5.28 (s, 2H) 6.39 (d, J=7.92 Hz, 1H) 7.10-7.23 (m, 2H) 7.30 (t, J=6.80 Hz, 1H) 7.38 (d, J=8.36 Hz, 1H) 7.63 (d, J=6.82 Hz, 1H) 8.21 (d, J=8.58 Hz, 1H); m/z=535.2 [M+H]$^+$ Compound 23: 1'-[[5-chloro-1-(4,4,4-trifluorobutyl)imidazo[4,5-b]pyridin-2-yl]methyl]-2'-oxo-N-tetrahydropyran-4-yl-spiro[azetidine-3,3'-indoline]-1-carboxamide

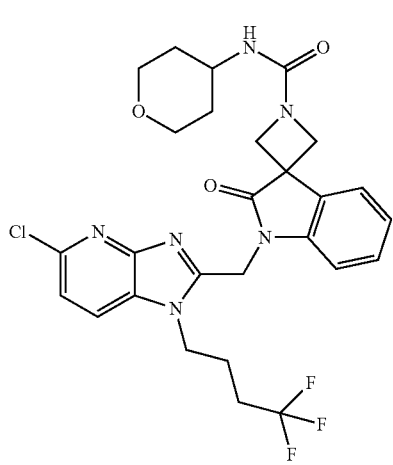 [SMILES: O=C(NC1CCOCC1)N1CC2(C1)C(=O)N(Cc1nc3nc(Cl)ccc3n1CCCC(F)(F)F)c1ccccc12]

¹H NMR (400 MHz, DMSO-d6) δ ppm 1.36-1.52 (m, 2H) 1.67-1.77 (m, 2H) 1.92-2.06 (m, 2H) 2.29-2.45 (m, 2H) 3.35 (m, 2H under water peak) 3.59-3.70 (m, 1H) 3.79-3.90 (m, 2H) 3.99 (d, J=7.92 Hz, 2H) 4.12 (d, J=8.14 Hz, 2H) 4.39-4.53 (m, 2H) 5.28 (s, 2H) 6.51 (d, J=7.70 Hz, 1H) 7.10-7.22 (m, 2H) 7.26-7.35 (m, 1H) 7.37 (d, J=8.36 Hz, 1H) 7.63 (d, J=7.04 Hz, 1H) 8.21 (d, J=8.58 Hz, 1H); m/z=577.2 [M+H]⁺

Compound 24: 1'[[5-chloro-1-(4,4,4-trifluorobutyl)imidazo[4,5-b]pyridin-2-yl]methyl]-N-(3-hydroxycyclobutyl)-2'-oxo-spiro[azetidine-3,3'-indoline]-1-carboxamide

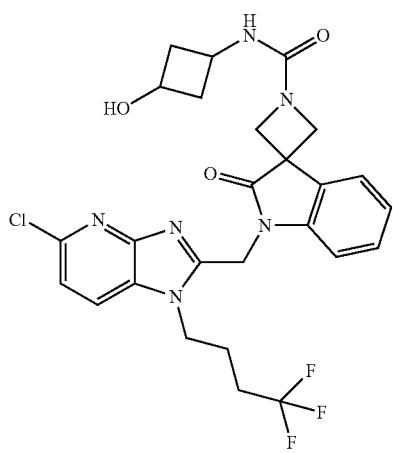 [SMILES: O=C(NC1CC(O)C1)N1CC2(C1)C(=O)N(Cc1nc3nc(Cl)ccc3n1CCCC(F)(F)F)c1ccccc12]

¹H NMR (400 MHz, DMSO-d6) δ (some protons show cis/trans isomerism) ppm 1.71-1.86 (m, 2H major) 1.91-2.04 (m, 2H) 2.04-2.22 (m, 4H minor) 2.28-2.49 (m, 2H+2H major) 3.55-3.67 (m, 1H major) 3.73-3.86 (m, 1H major) 3.93-4.05 (m, 2H) 4.07-4.15 (m, 2H) 4.17-4.31 (m, 2H minor) 4.46 (t, J=7.59 Hz, 2H) 4.96 (d, J=5.28 Hz, 1H minor) 5.04 (d, J=5.50 Hz, 1H major) 5.29 (s, 2H) 6.72-6.85 (m, 1H) 7.10-7.23 (m, 2H) 7.27-7.35 (m, 1H) 7.38 (d, J=8.36 Hz, 1H) 7.64 (d, J=7.26 Hz, 1H) 8.22 (d, J=8.36 Hz, 1H); m/z=563.2 [M+H]⁺

Compound 25: 1'-[[5-chloro-1-(3-cyanopropyl)indol-2-yl]methyl]-N-methyl-2'-oxo-spiro[piperidine-4,3'-pyrrolo[2,3-c]pyridine]-1-carboxamide

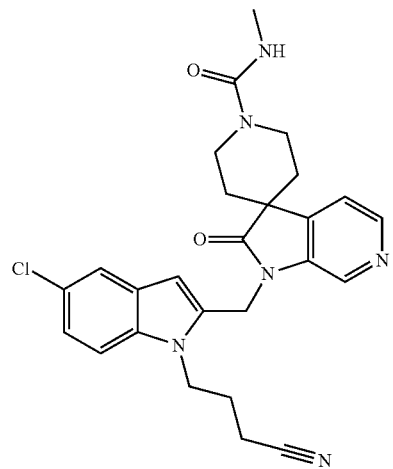 [SMILES: CNC(=O)N1CCC2(CC1)C(=O)N(Cc1cc3cc(Cl)ccc3n1CCCC#N)c1cnccc12]

To a solution of (17b) (232 mg, 0.535 mmole) in DCM (5 mL) were added methylaminoformyl chloride (50 mg, 1 eq) and triethylamine (0.223 mL, 3 eq.) at room temperature. After 30 minutes, iced water was added and the mixture was stirred for 1 hour. The product was extracted with DCM (2×). The organic layers were combined, dried over Na₂SO₄, filtered and evaporated to get an off-white foam, which was triturated in DIPE. The resulting yellow solid was collected by filtration to provide compound (25) (217 mg, 80% yield).
¹H NMR (400 MHz, DMSO-d6) δ ppm 1.66-1.85 (m, 4H) 1.99 (quin, J=7.48 Hz, 2H) 2.58 (t, J=7.37 Hz, 2H) 2.62 (d, J=4.40 Hz, 3H) 3.54-3.81 (m, 4H) 4.23-4.36 (m, 2H) 5.19 (s, 2H) 6.35 (s, 1H) 6.53 (q, J=4.00 Hz, 1H) 7.15 (dd, J=8.80, 1.98 Hz, 1H) 7.49-7.56 (m, 2H) 7.68 (d, J=4.62 Hz, 1H) 8.32 (d, J=4.84 Hz, 1H) 8.38 (s, 1H); m/z=491.14 (M+H)⁺

Compound 26: 1'-[[5-chloro-1-(3-cyanopropyl)benzimidazol-2-yl]methyl]-N-methyl-2'-oxo-spiro[piperidine-4,3'-pyrrolo[2,3-c]pyridine]-1-carboxamide

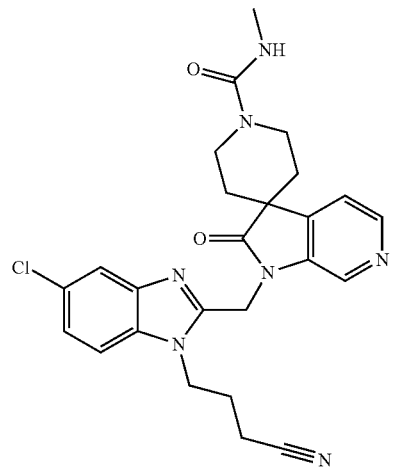 [SMILES: CNC(=O)N1CCC2(CC1)C(=O)N(Cc1nc3cc(Cl)ccc3n1CCCC#N)c1cnccc12]

Compound (26) was synthesized following the procedure reported for compound (25), using intermediate (18b) instead of (17b), and was obtained as a slightly pink solid in 79% yield.

$^1$H NMR (400 MHz, DMSO-d6) δ ppm 1.67-1.84 (m, 4H) 2.09 (quin, J=7.43 Hz, 2H) 2.57-2.71 (m, 5H) 3.56-3.77 (m, 4H) 4.39 (t, J=7.48 Hz, 2H) 5.30 (s, 2H) 6.46-6.60 (m, 1H) 7.30 (dd, J=8.69, 1.87 Hz, 1H) 7.60-7.72 (m, 3H) 8.32 (d, J=4.62 Hz, 1H) 8.47 (s, 1H); m/z=492.18 (M+H)+; MP=99.81° C.

Compound 27: 1'-[[5-chloro-1-(3-methylsulfonyl-propyl)indol-2-yl]methyl]-N-isopropyl-2'-oxo-spiro[piperidine-4,3'-pyrrolo[2,3-c]pyridine]-1-carboxamide

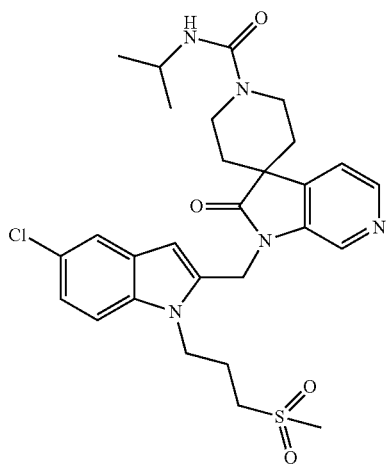 [SMILES: CC(C)NC(=O)N1CCC2(CC1)C(=O)N(Cc1cc3cc(Cl)ccc3n1CCCS(C)(=O)=O)c1cnccc12]

Compound (27) was synthesized following the procedure reported for compound (1), using intermediate (16b) instead of (10b), and was obtained as a white foam (quantitative yield).

$^1$H NMR (400 MHz, DMSO-d6) δ ppm 1.09 (d, J=6.60 Hz, 6H) 1.64-1.87 (m, 4H) 2.10 (quin, J=7.65 Hz, 2H) 3.01 (s, 3H) 3.14-3.25 (m, 2H) 3.55-3.91 (m, 5H) 4.27-4.48 (m, 2H) 5.20 (s, 2H) 6.27 (d, J=7.48 Hz, 1H) 6.36 (s, 1H) 7.16 (dd, J=8.69, 2.09 Hz, 1H) 7.53 (d, J=1.98 Hz, 1H) 7.55 (d, J=8.80 Hz, 1H) 7.65-7.72 (m, 1H) 8.33 (d, J=4.84 Hz, 1H) 8.38 (s, 1H); m/z=572.11 (M+H)+

Compound 28: 1'-[[5-chloro-1-(3-cyanopropyl)indol-2-yl]methyl]-N-isopropyl-2'-oxo-spiro[piperidine-4,3'-pyrrolo[2,3-c]pyridine]-1-carboxamide

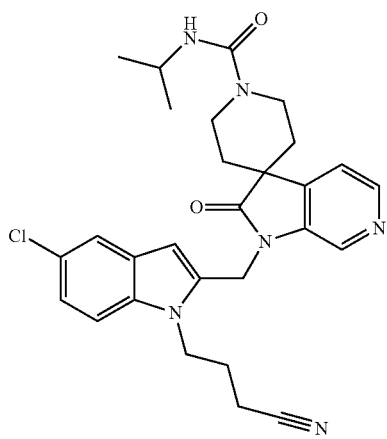 [SMILES: CC(C)NC(=O)N1CCC2(CC1)C(=O)N(Cc1cc3cc(Cl)ccc3n1CCCC#N)c1cnccc12]

Compound (28) was synthesized following the procedure reported for compound (1), using intermediate (17b) instead of (10b), and was obtained as a white foam (78% yield).

$^1$H NMR (400 MHz, DMSO-d6) δ ppm 1.02-1.17 (m, 6H) 1.66-1.85 (m, 4H) 1.99 (quin, J=7.48 Hz, 2H) 2.58 (t, J=7.37 Hz, 2H) 3.55-3.87 (m, 5H) 4.24-4.34 (m, 2H) 5.19 (s, 2H) 6.27 (d, J=7.70 Hz, 1H) 6.35 (s, 1H) 7.12-7.18 (m, 1H) 7.50-7.56 (m, 2H) 7.66-7.72 (m, 1H) 8.33 (d, J=4.84 Hz, 1H) 8.38 (s, 1H); m/z=519.12 (M+H)+

Compound 29: 1'-[[5-chloro-1-(3-cyanopropyl)benzimidazol-2-yl]methyl]-N-isopropyl-2'-oxo-spiro[piperidine-4,3'-pyrrolo[2,3-c]pyridine]-1-carboxamide

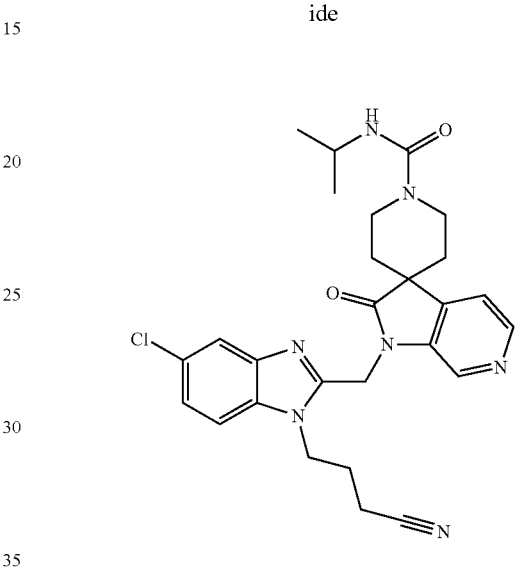

Compound (29) was synthesized following the procedure reported for compound (1), using intermediate (18b) instead of (10b), and was obtained as a white solid (47% yield).

$^1$H NMR (400 MHz, DMSO-d6) δ ppm 1.08 (d, J=6.60 Hz, 6H) 1.63-1.84 (m, 4H) 1.9-2.19 (m, 2H) 2.62 (t, J=7.37 Hz, 2H) 3.50-3.66 (m, 2H) 3.66-3.77 (m, 2H) 3.77-3.86 (m, 1H) 4.39 (t, J=7.00 Hz, 2H) 5.29 (s, 2H) 6.18 (d, J=7.48 Hz, 1H) 7.29 (dd, J=8.58, 1.98 Hz, 1H) 7.55-7.71 (m, 3H) 8.32 (d, J=4.62 Hz, 1H) 8.47 (s, 1H); m/z=520.25 (M+H)+.

Table F-1 and Table F-2 list the compounds that were prepared in accordance with the above Examples.

TABLE F-1

| Co. No. 1 |
|---|
| 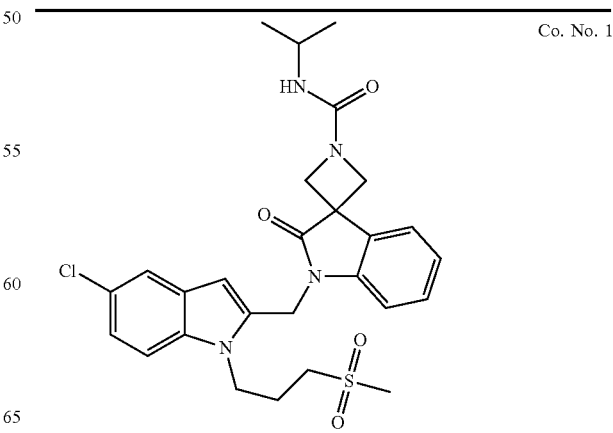 |

TABLE F-1-continued
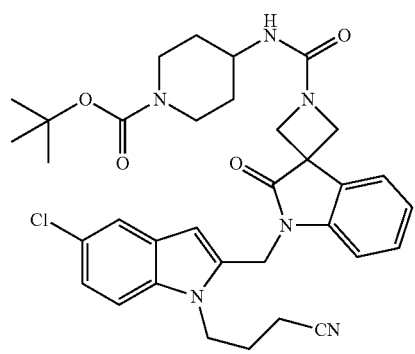 [SMILES: CC(C)(C)OC(=O)N1CCC(NC(=O)N2CC3(C2)C(=O)N(Cc2cc4cc(Cl)ccc4n2CCCC#N)c2ccccc23)CC1]
Co. No. 2
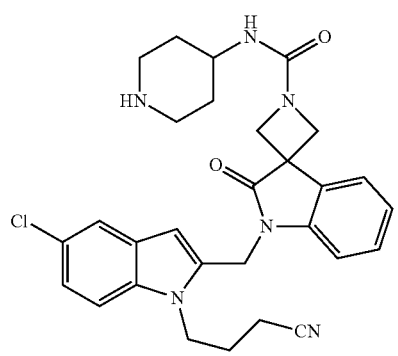 [SMILES: N#CCCCn1c(CN2C(=O)C3(CN(C(=O)NC4CCNCC4)C3)c3ccccc32)cc2cc(Cl)ccc21]
Co. No. 3
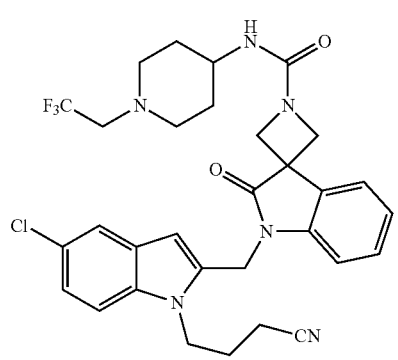 [SMILES: N#CCCCn1c(CN2C(=O)C3(CN(C(=O)NC4CCN(CC(F)(F)F)CC4)C3)c3ccccc32)cc2cc(Cl)ccc21]
Co. No. 4
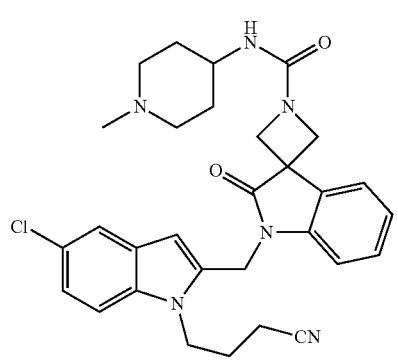 [SMILES: CN1CCC(NC(=O)N2CC3(C2)C(=O)N(Cc2cc4cc(Cl)ccc4n2CCCC#N)c2ccccc23)CC1]
Co. No. 5
TABLE F-1-continued
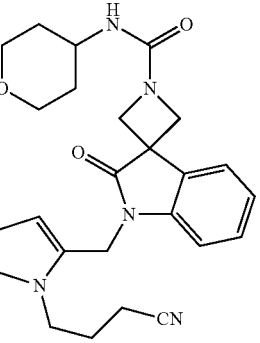
Co. No. 6
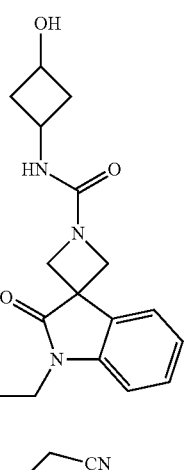
Co. No. 7
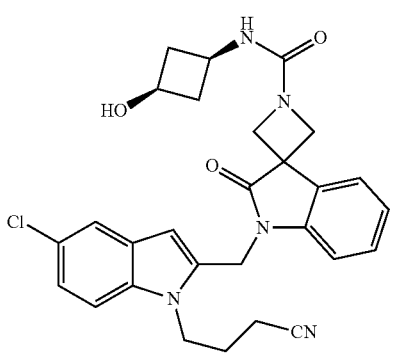 [SMILES: N#CCCCn1c(CN2C(=O)C3(CN(C(=O)N[C@H]4C[C@@H](O)C4)C3)c3ccccc32)cc2cc(Cl)ccc21]
Co. No. 8; (cis)
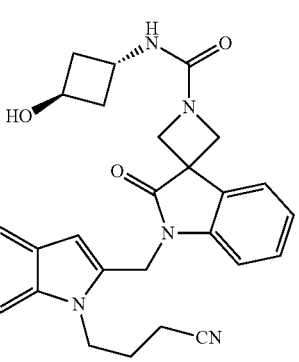
Co. No. 9; (trans)

TABLE F-1-continued
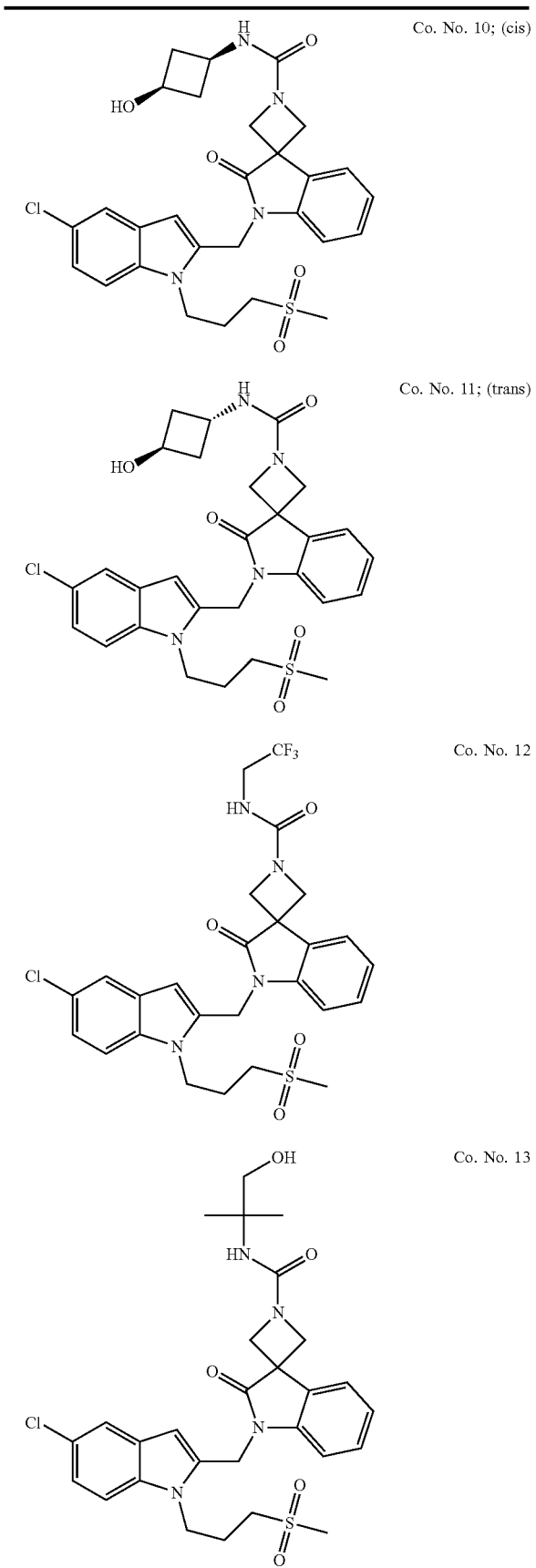
Co. No. 10; (cis)
Co. No. 11; (trans)
Co. No. 12
Co. No. 13
TABLE F-1-continued
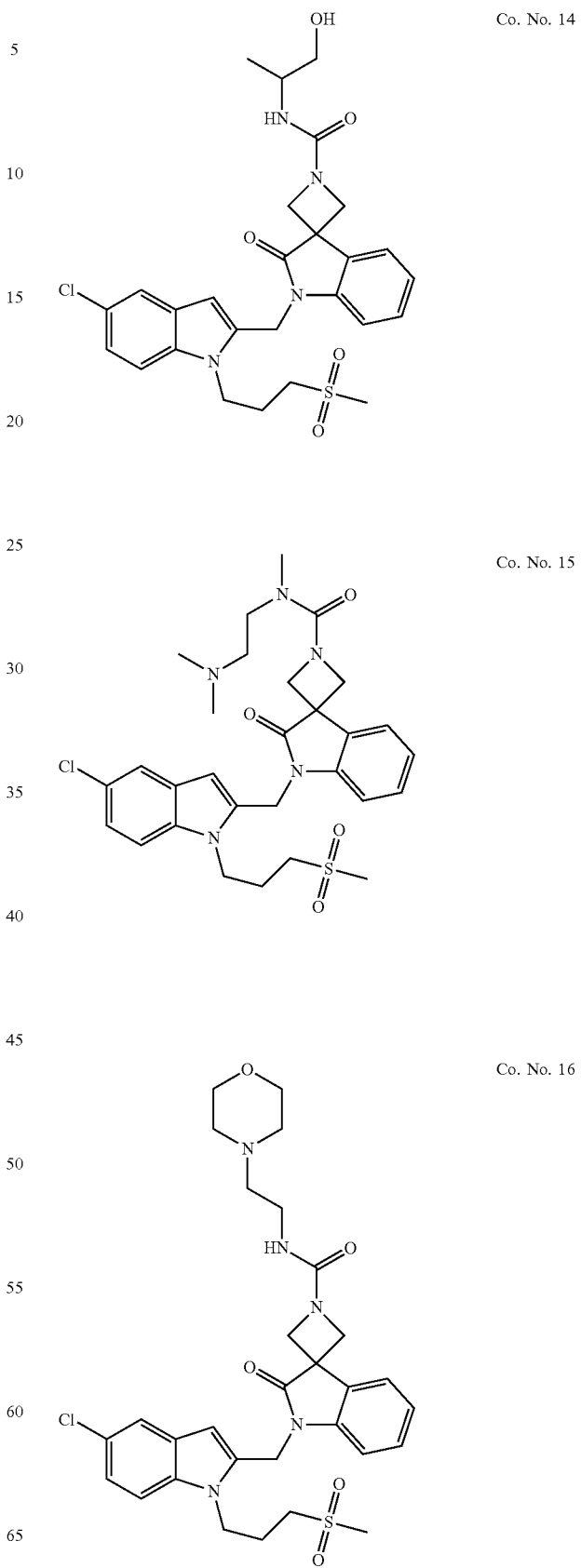
Co. No. 14
Co. No. 15
Co. No. 16

TABLE F-1-continued
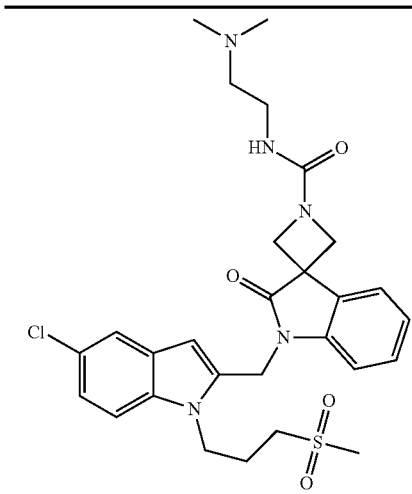
Co. No. 17
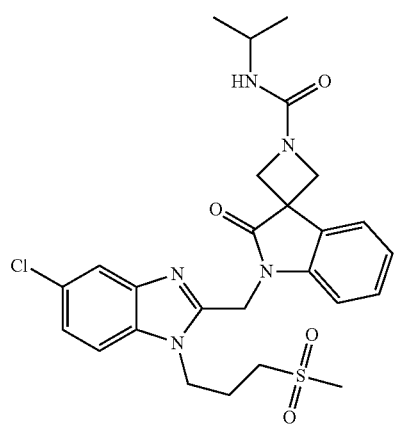 [SMILES: CC(C)NC(=O)N1CC2(C1)C(=O)N(Cc1nc3cc(Cl)ccc3n1CCCS(C)(=O)=O)c1ccccc12]
Co. No. 18
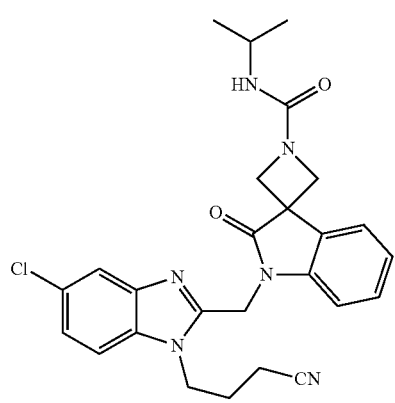 [SMILES: CC(C)NC(=O)N1CC2(C1)C(=O)N(Cc1nc3cc(Cl)ccc3n1CCCC#N)c1ccccc12]
Co. No. 19
TABLE F-1-continued
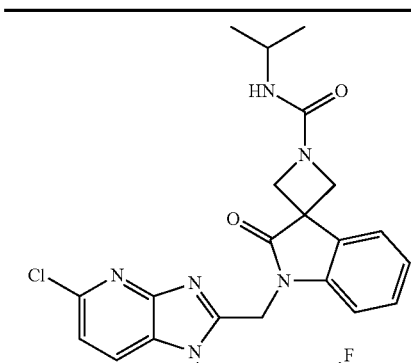
Co. No. 20
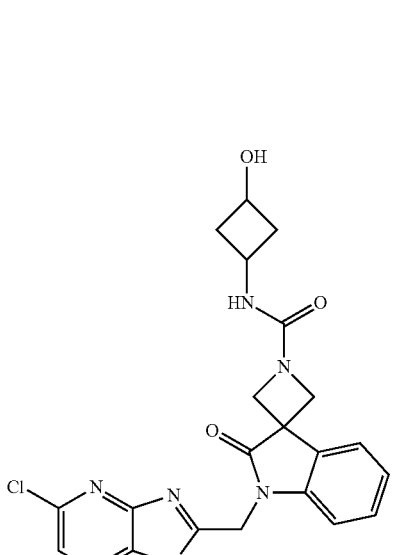
Co. No. 21
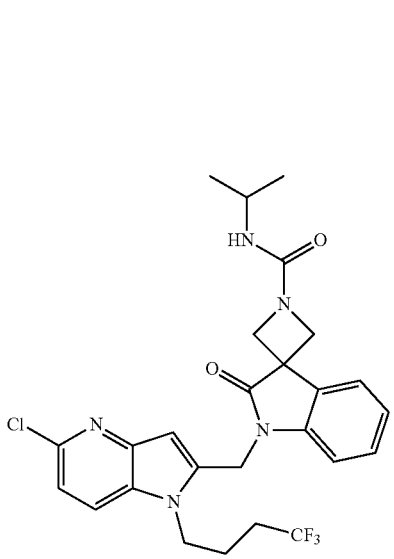 [SMILES: CC(C)NC(=O)N1CC2(C1)C(=O)N(Cc1cc3nc(Cl)ccc3n1CCCC(F)(F)F)c1ccccc12]
Co. No. 22

TABLE F-1-continued
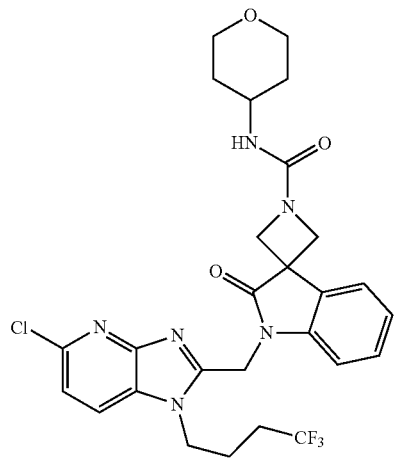 [SMILES: O=C(NC1CCOCC1)N1CC2(C1)C(=O)N(Cc1nc3nc(Cl)ccc3n1CCCC(F)(F)F)c1ccccc12]
Co. No. 23
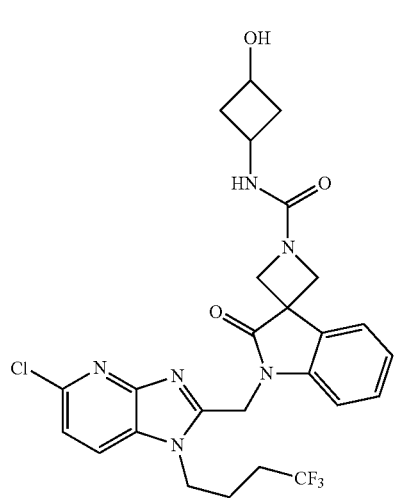 [SMILES: O=C(NC1CC(O)C1)N1CC2(C1)C(=O)N(Cc1nc3nc(Cl)ccc3n1CCCC(F)(F)F)c1ccccc12]
Co. No. 24
TABLE F-2
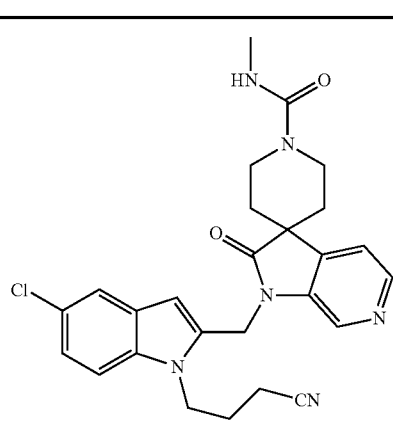
Co. No. 25
TABLE F-2-continued
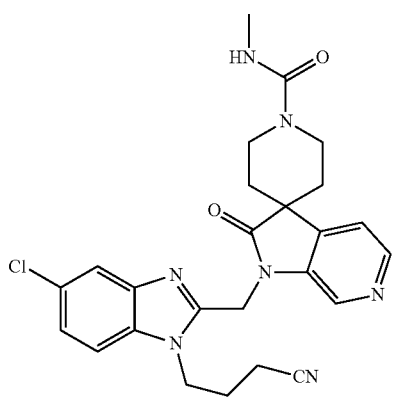 [SMILES: CNC(=O)N1CCC2(CC1)C(=O)N(Cc1nc3cc(Cl)ccc3n1CCCC#N)c1cnccc12]
Co. No. 26
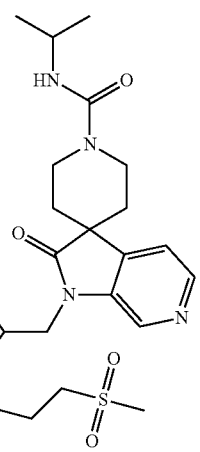
Co. No. 27
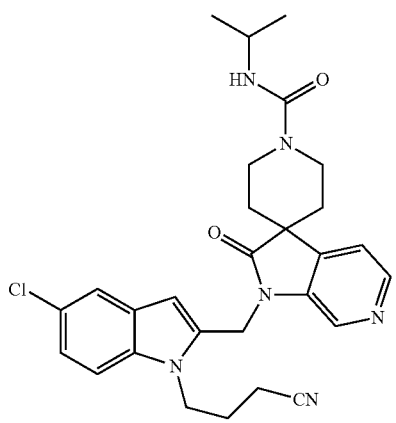 [SMILES: CC(C)NC(=O)N1CCC2(CC1)C(=O)N(Cc1cc3cc(Cl)ccc3n1CCCC#N)c1cnccc12]
Co. No. 28

TABLE F-2-continued

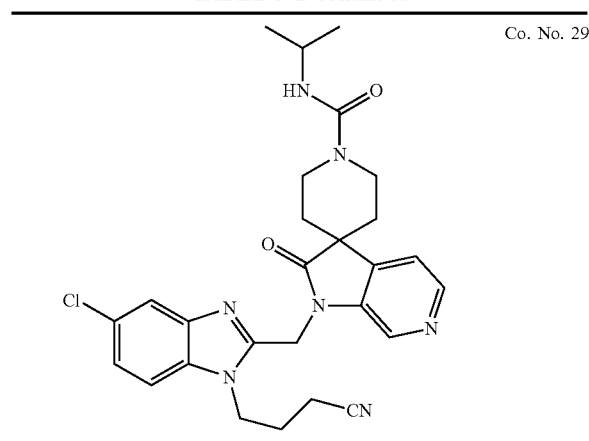

Co. No. 29

B. Pharmacological Examples

C.1 Antiviral Activity

Black 384-well clear-bottom microtiter plates (Corning, Amsterdam, The Netherlands) were filled via acoustic drop ejection using the echo liquid handler (Labcyte, Sunnyvale, Calif.). 200 nL of compound stock solutions (100% DMSO) were transferred to the assay plates. 9 serial 4-fold dilutions of compound were made, creating per quadrant the same compound concentration. The assay was initiated by adding 10 μL of culture medium to each well (RPMI medium without phenol red, 10% FBS-heat inactivated, 0.04% gentamycin (50 mg/mL). All addition steps are done by using a multidrop dispenser (Thermo Scientific, Erembodegem, Belgium). Next, rgRSV224 virus (MOI=1) diluted in culture medium was added to the plates. rgRSV224 virus is an engineered virus that includes an additional GFP gene (Hallak L K, Spillmann D, Collins P L, Peeples M E. Glycosaminoglycan sulfation requirements for respiratory syncytial virus infection; Journal of virology (2000), 74(22), 10508-13) and was in-licensed from the NIH (Bethesda, Md., USA). Finally, 20 μL of a HeLa cell suspension (3,000 cells/well) were plated. Medium, virus- and mock-infected controls were included in each test. The wells contain 0.05% DMSO per volume. Cells were incubated at 37° C. in a 5% CO2 atmosphere. Three days post-virus exposure, viral replication was quantified by measuring GFP expression in the cells by an in house developed MSM laser microscope (Tibotec, Beerse, Belgium). The EC50 was defined as the 50% inhibitory concentration for GFP expression. In parallel, compounds were incubated for three days in a set of white 384-well microtiter plates (Corning) and the cytotoxicity of compounds in HeLa cells was determined by measuring the ATP content of the cells using the ATPlite kit (Perkin Elmer, Zaventem, Belgium) according to the manufacturer's instructions. The $CC_{50}$ was defined as the 50% concentration for cytotoxicity.

TABLE B-1 antiviral data and selectivity index

| Co. No. | RSV HELA $pEC_{50}$ | SI TOX HELA |
|---|---|---|
| 1 | 10.05 | 356993.25 |
| 2 | 8.7 | >50000 |
| 3 | 9.2 | 158489 |
| 4 | 9 | 100000 |

TABLE B-1-continued antiviral data and selectivity index

| Co. No. | RSV HELA $pEC_{50}$ | SI TOX HELA |
|---|---|---|
| 5 | 8.5 | 10000 |
| 6 | 9.5 | 100000 |
| 7 | 9.39 | 102820.56 |
| 8 | >9.81652 | >232209 |
| 9 | >9.81652 | >253746 |
| 10 | >9.77061 | >504917 |
| 11 | 9.61 | 299785.09 |
| 12 | 9.57 | 86916.05 |
| 13 | 9.00 | 43414.02 |
| 14 | 9.24 | 98192.88 |
| 15 | 8.12 | 2574.19 |
| 16 | 9.47 | 158971.77 |
| 17 | 8.90 | 39320.59 |
| 18 | 10.69 | >4.93378e+006 |
| 19 | 10.04 | >1.109e+006 |
| 20 | 8.90 | >80225.1 |
| 21 | 8.85 | >71359.2 |
| 23 | 8.79 | >61793.1 |
| 24 | 8.88 | >75425.8 |
| 25 | 9.75 | >564664 |
| 26 | 10.26 | >1.81593e+006 |
| 27 | 9.59 | 299785.06 |
| 28 | 8.67 | 25403.88 |
| 29 | 10.61 | >4.10525e+006 |

C. Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

C.1. Tablets

| Active ingredient | 5 to 50 mg |
|---|---|
| Di calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

C.2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

C.3. Injectable

A parenteral composition is prepared by stirring 1.5% by weight of active ingredient of the invention in 10% by volume propylene glycol in water.

C.4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of formula (I)

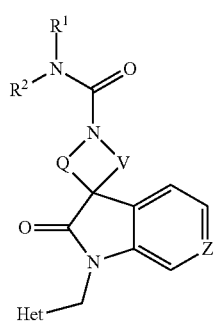

(I)

including any stereochemically isomeric form thereof, wherein

Het is a heterocyclic moiety selected from the group consisting of: (a), (b) and (c):

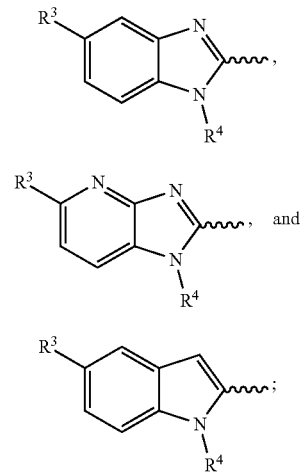

Q is $CH_2$ or $CH_2CH_2$;
V is $CH_2$ or $CH_2CH_2$;
Z is CH or N;
$R^1$ is selected from the group consisting of: $C_{1-6}$alkyl; $C_{3-6}$cycloalkyl; $C_{3-6}$cycloalkyl substituted with hydroxy; $Het^1$; and $C_{1-6}$alkyl substituted with one substituent selected from the group consisting of: halo, hydroxy, polyhalo$C_{1-4}$alkyl, $NR^5R^6$, $Het^2$, $C_{3-6}$cycloalkyl, and $C_{3-6}$cycloalkyl substituted with hydroxy; wherein $R^5$ is hydrogen or $C_{1-4}$alkyl; and $R^6$ is hydrogen or $C_{1-4}$alkyl;
$R^2$ is hydrogen or $C_{1-6}$alkyl;
$R^3$ is halo;
$R^4$ is —$(CH_2)_m$—$R^7$;
m is an integer from 2 to 4;
$R^7$ is selected from the group consisting of: halogen, CN, $CF_3$, and $SO_2CH_3$;
$Het^1$ is selected from the group consisting of: azetidinyl, pyrrolidinyl, piperidinyl, and tetrahydropyranyl; wherein Het' is optionally substituted with $C_{1-4}$alkyl, polyhalo$C_{1-4}$alkyl or $C_{1-4}$alkyloxycarbonyl; and
$Het^2$ is selected from the group consisting of: azetidinyl, pyrrolidinyl, piperidinyl, piperazinyl, morpholinyl and tetrahydropyranyl; wherein $Het^2$ is optionally substituted with $C_{1-4}$alkyl or polyhalo$C_{1-4}$alkyl;
or a pharmaceutically acceptable acid addition salt thereof.

2. The compound as claimed in claim 1 wherein Het is of formula (a).

3. The compound as claimed in claim 1 wherein Het is of formula (b).

4. The compound as claimed in claim 1 wherein Het is of formula (c).

5. The compound as claimed in claim 1 wherein Q is $CH_2$ and V is $CH_2$.

6. The compound as claimed in claim 1 wherein Q is $CH_2CH_2$ and V is $CH_2CH_2$.

7. The compound as claimed in claim 1 wherein Q is $CH_2$, V is $CH_2$, and Z is CH.

8. The compound as claimed in claim 1 wherein Q is $CH_2CH_2$, V is $CH_2CH_2$, and Z is CH.

9. The compound as claimed in claim 1 wherein Q is $CH_2$, V is $CH_2$, and Z is N.

10. The compound as claimed in claim 1 wherein Q is $CH_2CH_2$, V is $CH_2CH_2$, and Z is N.

11. A pharmaceutical composition comprising a pharmaceutically acceptable carrier and a therapeutically active amount of a compound as claimed in claim 1 or a pharmaceutically acceptable salt thereof.

12. A method of treating a respiratory syncytial virus infection in a patient comprising administering the compound as claimed in claim 1 or pharmaceutically acceptable salt thereof to said patient.

13. A method of treating a respiratory syncytial virus infection in a patient comprising administering the pharmaceutical composition as claimed in claim 11 to said patient.

14. A compound selected from the group consisting of:
1'-[[5-Chloro-1-(3-methylsulfonylpropyl)indol-2-yl]methyl]-N-isopropyl-2'-oxo-spiro[azetidine-3,3'-indoline]-1-carboxamide;
tert-Butyl 4-[[1'-[[5-chloro-1-(3-cyanopropyl)indol-2-yl]methyl]-2'-oxo-spiro[azetidine-3,3'-indoline]-1-carbonyl]amino]piperidine-1-carboxylate;
1'-[[5-Chloro-1-(3-cyanopropyl)indol-2-yl]methyl]-2'-oxo-N-(4-piperidyl)spiro[azetidine-3,3'-indoline]-1-carboxamide;
1'-[[5-Chloro-1-(3-cyanopropyl)indol-2-yl]methyl]-2'-oxo-N-[1-(2,2,2-trifluoroethyl)-4-piperidyl]spiro[azetidine-3,3'-indoline]-1-carboxamide;
1'-[[5-Chloro-1-(3-cyanopropyl)indol-2-yl]methyl]-N-(1-methyl-4-piperidyl)-2'-oxo-spiro[azetidine-3,3'-indoline]-1-carboxamide;
1'-[[5-Chloro-1-(3-cyanopropyl)indol-2-yl]methyl]-2'-oxo-N-tetrahydropyran-4-yl-spiro[azetidine-3,3'-indoline]-1-carboxamide;
1'-[[5-Chloro-1-(3-cyanopropyl)indol-2-yl]methyl]-N-(3-hydroxycyclobutyl)-2'-oxo-spiro[azetidine-3,3'-indoline]-1-carboxamide;
1'-[[5-Chloro-1-(3-cyanopropyl)indol-2-yl]methyl]-N-(cis-3-hydroxycyclobutyl)-2'-oxo-spiro[azetidine-3,3'-indoline]-1-carboxamide;

1'-[[5-Chloro-1-(3-cyanopropyl)indol-2-yl]methyl]-N-(trans-3-hydroxycyclobutyl)-2'-oxo-spiro[azetidine-3,3'-indoline]-1-carboxamide;

1'-[[5-Chloro-1-(3-methylsulfonylpropyl)indol-2-yl]methyl]-N-(cis-3-hydroxycyclobutyl)-2'-oxo-spiro[azetidine-3,3'-indoline]-1-carboxamide;

1'-[[5-Chloro-1-(3-methylsulfonylpropyl)indol-2-yl]methyl]-N-(trans-3-hydroxycyclobutyl)-2'-oxo-spiro[azetidine-3,3'-indoline]-1-carboxamide;

1'-[[5-Chloro-1-(3-methylsulfonylpropyl)indol-2-yl]methyl]-2'-oxo-N-(2,2,2-trifluoroethyl)spiro[azetidine-3,3'-indoline]-1-carboxamide;

1'-[[5-Chloro-1-(3-methylsulfonylpropyl)indol-2-yl]methyl]-N-(2-hydroxy-1,1-dimethyl-ethyl)-2'-oxo-spiro[azetidine-3,3'-indoline]-1-carboxamide;

1'-[[5-Chloro-1-(3-methylsulfonylpropyl)indol-2-yl]methyl]-N-(2-hydroxy-1-methyl-ethyl)-2'-oxo-spiro[azetidine-3,3'-indoline]-1-carboxamide;

1'-[[5-Chloro-1-(3-methylsulfonylpropyl)indol-2-yl]methyl]-N-[2-(dimethylamino)ethyl]-N-methyl-2'-oxo-spiro[azetidine-3,3'-indoline]-1-carboxamide;

1'-[[5-Chloro-1-(3-methylsulfonylpropyl)indol-2-yl]methyl]-N-(2-morpholinoethyl)-2'-oxo-spiro[azetidine-3,3'-indoline]-1-carboxamide;

1'-[[5-Chloro-1-(3-methylsulfonylpropyl)indol-2-yl]methyl]-N-[2-(dimethylamino)ethyl]-2'-oxo-spiro[azetidine-3,3'-indoline]-1-carboxamide;

1'-[[5-Chloro-1-(3-methylsulfonylpropyl)benzimidazol-2-yl]methyl]-N-isopropyl-2'-oxo-spiro[azetidine-3,3'-indoline]-1-carboxamide;

1'-[[5-Chloro-1-(3-cyanopropyl)benzimidazol-2-yl]methyl]-N-isopropyl-2'-oxo-spiro[azetidine-3,3'-indoline]-1-carboxamide;

1'-[[5-Chloro-1-(4-fluorobutyl)imidazo[4,5-b]pyridin-2-yl]methyl]-N-isopropyl-2'-oxo-spiro[azetidine-3,3'-indoline]-1-carboxamide;

1'-[[5-Chloro-1-(4-fluorobutyl)imidazo[4,5-b]pyridin-2-yl]methyl]-N-(3-hydroxycyclobutyl)-2'-oxo-spiro[azetidine-3,3'-indoline]-1-carboxamide;

1'-[[5-Chloro-1-(4,4,4-trifluorobutyl)imidazo[4,5-b]pyridin-2-yl]methyl]-N-isopropyl-2'-oxo-spiro[azetidine-3,3'-indoline]-1-carboxamide;

1'-[[5-Chloro-1-(4,4,4-trifluorobutyl)imidazo[4,5-b]pyridin-2-yl]methyl]-2'-oxo-N-tetrahydropyran-4-yl-spiro[azetidine-3,3'-indoline]-1-carboxamide;

1'-[[5-Chloro-1-(4,4,4-trifluorobutyl)imidazo[4,5-b]pyridin-2-yl]methyl]-N-(3-hydroxycyclobutyl)-2'-oxo-spiro[azetidine-3,3'-indoline]-1-carboxamide;

1'-[[5-Chloro-1-(3-cyanopropyl)indol-2-yl]methyl]-N-methyl-2'-oxo-spiro[piperidine-4,3'-pyrrolo[2,3-c]pyridine]-1-carboxamide;

1'-[[5-Chloro-1-(3-cyanopropyl)benzimidazol-2-yl]methyl]-N-methyl-2'-oxo-spiro[piperidine-4,3'-pyrrolo[2,3-c]pyridine]-1-carboxamide;

1'-[[5-Chloro-1-(3-methylsulfonylpropyl)indol-2-yl]methyl]-N-isopropyl-2'-oxo-spiro[piperidine-4,3'-pyrrolo[2,3-c]pyridine]-1-carboxamide;

1'-[[5-Chloro-1-(3-cyanopropyl)indol-2-yl]methyl]-N-isopropyl-2'-oxo-spiro[piperidine-4,3'-pyrrolo[2,3-c]pyridine]-1-carboxamide; and 1'-[[5-Chloro-1-(3-cyanopropyl)benzimidazol-2-yl]methyl]-N-isopropyl-2'-oxo-spiro[piperidine-4,3'-pyrrolo[2,3-c]pyridine]-1-carboxamide;

and pharmaceutically acceptable acid addition salts thereof.

15. A pharmaceutical composition comprising:

(a) an effective amount of at least one compound selected from compounds of claim 14 and pharmaceutically acceptable salts of compounds of claim 14; and (b) at least one pharmaceutically acceptable excipient.

\* \* \* \* \*